US009247746B2

(12) United States Patent
Dietz et al.

(10) Patent No.: US 9,247,746 B2
(45) Date of Patent: Feb. 2, 2016

(54) FUNGICIDAL SUBSTITUTED 1-{2-CYCLYLOXY-2-[2-HALO-4-(4-HALOGEN-PHENOXY)-PHENYL]-ETHYL}-1H-[1,2,4]TRIAZOLE COMPOUNDS

(75) Inventors: Jochen Dietz, Karlsruhe (DE); Richard Riggs, Mannheim (DE); Nadege Boudet, Hemsbach (DE); Jan Klaas Lohmann, Lambsheim (DE); Ian Robert Craig, Ludwigshafen (DE); Egon Haden, Speyer (DE); Erica May Wilson Lauterwasser, Mannheim (DE); Bernd Mueller, Frankenthal (DE); Wassilios Grammenos, Ludwigshafen (DE); Thomas Grote, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/237,040

(22) PCT Filed: Aug. 14, 2012

(86) PCT No.: PCT/EP2012/065850
§ 371 (c)(1),
(2), (4) Date: Feb. 4, 2014

(87) PCT Pub. No.: WO2013/024082
PCT Pub. Date: Feb. 21, 2013

(65) Prior Publication Data
US 2014/0235441 A1    Aug. 21, 2014

(30) Foreign Application Priority Data

Aug. 15, 2011   (EP) ..................................... 11177549

(51) Int. Cl.
*C07D 249/08*   (2006.01)
*A01N 43/653*   (2006.01)
(52) U.S. Cl.
CPC ............ *A01N 43/653* (2013.01); *C07D 249/08* (2013.01)
(58) Field of Classification Search
CPC .................................................... C07D 249/08
See application file for complete search history.

(56) References Cited

U.S. PATENT DOCUMENTS

| | | | |
|---|---|---|---|
| 4,242,121 | A | 12/1980 | Hawkins et al. |
| 4,599,362 | A | 7/1986 | Nakatani et al. |
| 4,940,720 | A | 7/1990 | Nevill et al. |
| 4,945,100 | A | 7/1990 | Nyfeler et al. |
| 4,992,458 | A | 2/1991 | Riebli et al. |
| 5,143,932 | A | 9/1992 | Jautelat et al. |
| 5,162,358 | A | 11/1992 | Jautelat et al. |
| 2008/0108686 | A1 | 5/2008 | Gewehr et al. |
| 2009/0036509 | A1 | 2/2009 | Gewehr et al. |
| 2009/0286768 | A1 | 11/2009 | Crew et al. |

FOREIGN PATENT DOCUMENTS

| | | |
|---|---|---|
| AU | 611315 | 6/1991 |
| CA | 1100976 | 5/1981 |
| CA | 1209152 | 8/1986 |
| CN | 101225074 | 7/2008 |
| CS | 247 200 | 12/1986 |
| DE | 2 325 878 | 12/1974 |
| DE | 3801233 | 8/1988 |
| DE | 4003180 | 8/1991 |
| EP | 0 000 017 | 12/1978 |
| EP | 0113640 | 7/1984 |
| EP | 0 126 430 | 11/1984 |
| EP | 0126430 | 11/1984 |
| EP | 0275955 | 7/1988 |
| EP | 0 354 183 | 2/1990 |
| EP | 0 440 950 | 8/1991 |
| EP | 0 470 466 | 2/1992 |
| EP | 1 431 275 | 6/2004 |
| FR | 2 491 924 | 4/1982 |
| GB | 2 132 195 | 7/1984 |
| WO | WO 96/41804 | 12/1996 |
| WO | WO 03 064572 | 8/2003 |
| WO | WO 2005/123689 | 12/2005 |
| WO | WO 2005/123690 | 12/2005 |
| WO | WO 2006/015866 | 2/2006 |
| WO | WO 2006/087373 | 8/2006 |
| WO | WO 2006/109933 | 10/2006 |
| WO | WO 2006/119876 | 11/2006 |
| WO | WO 2008/082198 | 7/2008 |
| WO | WO 2010/146114 | 12/2010 |
| WO | WO 2011/099804 | 8/2011 |
| WO | WO 2012/037782 | 3/2012 |
| WO | WO 2013/010862 | 1/2013 |
| WO | WO 2013/010885 | 1/2013 |
| WO | WO 2013/010894 | 1/2013 |

(Continued)

OTHER PUBLICATIONS

Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.

(Continued)

*Primary Examiner* — Shawquia Jackson
(74) *Attorney, Agent, or Firm* — Brinks Gilson & Lione

(57) ABSTRACT

The present invention relates to substituted 1-{2-cyclyloxy-2-[2-halo-4-(4-halogen-phenoxy)-phenyl]-ethyl}-1H-[1,2,4]triazole compounds of formula I as defined in the description, and the N-oxides, and salts thereof, processes and intermediates for preparing these compounds and also to compositions comprising at least one such compound. The invention also relates to the use of such compounds and compositions for combating harmful fungi and seed coated with at least one such compound.

20 Claims, No Drawings

(56) References Cited

FOREIGN PATENT DOCUMENTS

| WO | WO 2013/024076 | 1/2013 |
| WO | WO 2013/024077 | 1/2013 |
| WO | WO 2013007767 | 1/2013 |
| WO | WO 2013/024075 | 2/2013 |
| WO | WO 2013/024080 | 2/2013 |
| WO | WO 2013/024081 | 2/2013 |
| WO | WO 2013/024083 | 2/2013 |

OTHER PUBLICATIONS

Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.

International Preliminary Report on Patentability, issued in PCT/EP2012/065850, dated Aug. 23, 2013.

Internation Search Report, issued in PCT/EP2012/065850, dated Sep. 27, 2012.

European Search Report, issued in co-assigned Application No. 11177549.0, dated Nov. 8, 2011.

Office Action dated Dec. 10, 2014, issued in U.S. Appl. No. 14/237,463.

Office Action dated Dec. 1, 2014, issued in U.S. Appl. No. 14/232,434.

Office Action dated Dec. 8, 2014, issued in U.S. Appl. No. 14/232,462.

Office Action dated Dec. 8, 2014, issued in U.S. Appl. No. 14/237,048.

Lima, Lidia Moreira et al., "Bioisosterism: A useful strategy for molecular Modification and drug design", Current Medicinal Chemistry, 2005, p. 23-49, vol. 12.

FUNGICIDAL SUBSTITUTED 1-{2-CYCLYLOXY-2-[2-HALO-4-(4-HALOGEN-PHENOXY)-PHENYL]-ETHYL}-1H-[1,2,4]TRIAZOLE COMPOUNDS

This application is a National Stage application of International Application No. PCT/EP2012/065850, filed Aug. 14, 2012, the entire contents of which is hereby incorporated herein by reference. This application also claims priority under 35 U.S.C. §119 to European Patent Application No. 11177549.0, filed Aug. 15, 2011, the entire contents of which is hereby incorporated herein by reference.

The present invention relates to fungicidal 1-{2-cyclyloxy-2-[2-halo-4-(4-halogen-phenoxy)-phenyl]ethyl}1H-[1,2,4]triazole compounds and the N-oxides and the salts thereof for combating phytopathogenic fungi, and to the use and methods for combating phytopathogenic fungi and to seeds coated with at least one such compound. The invention also relates to processes for preparing these compounds and to compositions comprising at least one such compound.

EP 0 126 430 A2 concerns antifungal substituted 1H-[1,2,4]triazole compounds of formula

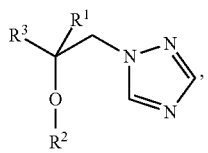

wherein $R^3$ can inter alia be phenyl optionally substituted by 1 to 3 halogen, $C_1$-$C_6$-haloalkyl, $C_1$-$C_6$-haloalkoxy, $C_1$-$C_6$-alkoxy, $C_1$-$C_6$-alkyl, phenoxy, halophenoxy, phenyl, benzyl, halobenzyl, nitro and/or cyano, and wherein $R^2$ can be unsubstituted $C_1$-$C_6$-alkyl, $C_1$-$C_6$-alkyl substituted by $C_1$-$C_6$-alkoxy, $C_3$-$C_4$-alkenyl, benzyl or halobenzyl.

The compounds according to the present invention differ from those described in the abovementioned publications the combination of the particular 2-[2-halo-4-(4-halogen-phenoxy)-phenyl] group and the specific $R^2$ group as defined herein. DE 3801233 A1 is directed to microbiocides of the formula I

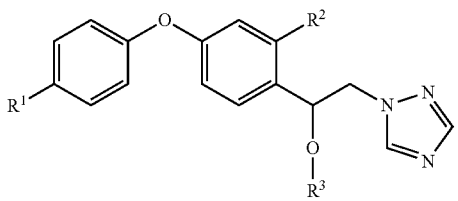

wherein $R^1$ is halogen and $R^2$ is halogen or methyl, $R^3$ is alkyl, haloalkyl, alkoxyalkyl, alkenyl, alkynyl or cyclopropyl. Guang-Ping Yu et al. (J. Agric. Food Chem., vol. 57, 5 Jul. 2009, pp 4854-4860) is directed to the synthesis and fungicidal evaluation of certain 2-arylphenyl ether-3-(1H-1,2,4-triazol-1-yl)propan-2-ol derivatives. EP 0113640 A2 is directed to certain 1-azolyl-2-aryl-3-fluoroalkane-2-oles and their use as microbiocides.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by substituted 1-{2-cycyloxy-2-[2-halo-4-(4-halogen-phenoxy)-phenyl]ethyl}1H-[1,2,4]triazole compounds having good fungicidal activity against phytopathogenic harmful fungi.

Accordingly, the present invention relates to the compounds of formula I:

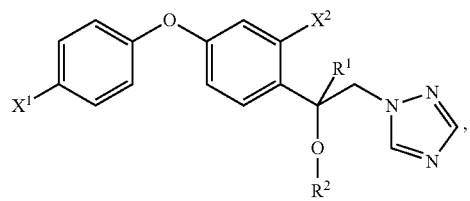

wherein:
$X^1$, $X^2$ independently of each other are selected from halogen;
$R^1$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;
$R^2$ is $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;
wherein the aliphatic moieties of $R^1$ and/or $R^2$ may carry 1, 2, 3 or up to the maximum possible number of identical or different groups $R^a$ which independently of one another are selected from:
$R^a$ halogen, CN, nitro, $C_1$-$C_4$-alkoxy and $C_1$-$C_4$-halogenalkoxy;
wherein the cycloalkyl and/or phenyl moieties of $R^1$ and/or $R^2$ may carry 1, 2, 3, 4, 5 or up to the maximum number of identical or different groups $R^b$ which independently of one another are selected from:
$R^b$ halogen, CN, nitro, $C_1$-$C_4$-alkyl, $C_1$-$C_4$-alkoxy, $C_1$-$C_4$-halogenalkyl and $C_1$-$C_4$-halogenalkoxy;
and the N-oxides and the agriculturally acceptable salts thereof.

The present invention furthermore relates to the use of these compounds for combating harmful fungi and seed coated with at least one such compound and also to compositions comprising at least one such compound of formula I.

The present invention furthermore relates to processes for preparing compounds of formula I and to intermediates such as compounds of formula Va, VI, VII, VIII, XI, XII and XIII.

The term "compounds I" refers to compounds of formula I. Likewise, this terminology applies to all sub-formulae, e.g. "compounds I.A" refers to compounds of formula I.A or "compounds XII" refers to compounds of formula XII, etc.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2) and by the synthesis routes shown in the following schemes and in the experimental part of this application.

In a first process, for example, halo-phenoles II wherein $X^1$ and $X^2$ as defined herein, are reacted, in a first step, with derivatives IIIa

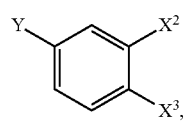

Y = F or Cl wherein $X^3$ stands for I or Br, in particular bromo derivatives III wherein Y is F or Cl, preferably in the presence of a base. Thereafter, the resulting compounds IVa, in particular IV (wherein $X^3$ is Br), are then transformed into Grignard

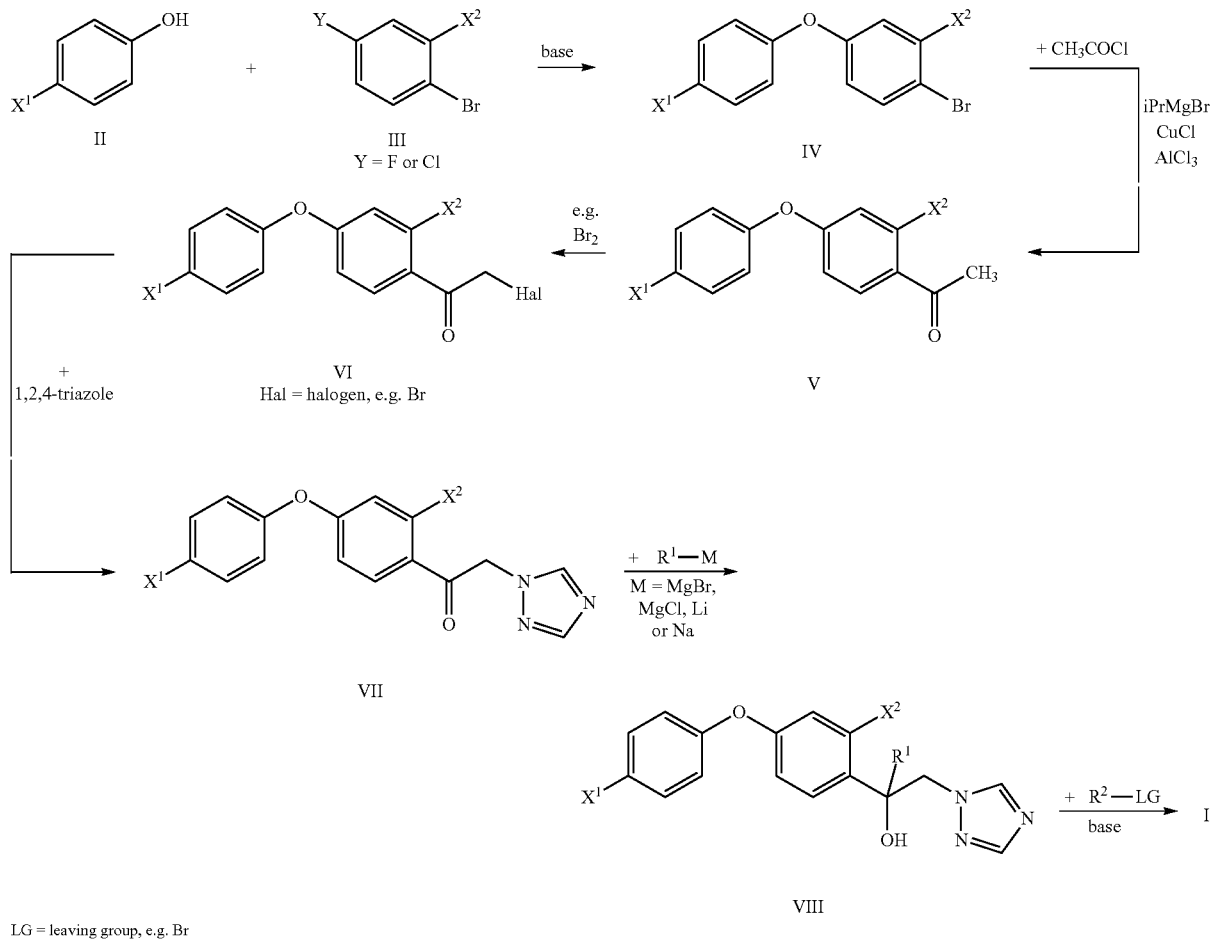

LG = leaving group, e.g. Br reagents by the reaction with trans-metallation reagents such as isopropylmagnesium halides and subsequently reacted with acetyl chloride preferably under anhydrous conditions and optionally in the presence of a catalyst such as CuCl, $AlC_{13}$, LiCl and mixtures thereof, to obtain acetophenones V. These compounds V can be halogenated e.g. with bromine or chlorine preferably in an organic solvent such as diethyl ether, methyl tert.-butyl ether (MTBE), methanol or acetic acid. The resulting compounds VI, wherein "Hal" stands for "halogen" such as e.g. Br or Cl, can subsequently reacted with 1H-1,2,4-triazole preferably in the presence of a solvent such as tetrahydrofuran (THF), dimethylormamide (DMF), toluene and in the presence of a base such as potassium carbonate, sodium hydroxide or sodium hydride to obtain compounds VII. These triazole compounds VII are reacted with a Grignard reagent $R^1$-M wherein $R^1$ is as defined herein and M is MgBr, MgCl, Li or Na (e.g. phenylalkyl-MgBr or an organolithium reagent phenylalkyl-Li), preferably under anhydrous conditions to obtain compounds VIII. Optionally, a Lewis acid such as $LaCl_3 \times 2 LiCl$ or $MgBr_2 \times OEt_2$ can be used. These compounds VIII are reacted with $R^2$-LG, wherein $R^1$ is as defined above and LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base, such as for example, NaH in a suitable solvent such as THF, to form compounds I. The preparation of compounds I can be illustrated by the following scheme:

In a second process to obtain compounds I, derivatives IIIa, in particular bromo derivatives III, in a first step, are reacted with e.g. isopropylmagnesium bromide followed by an acyl chloride agent IX wherein $R^1$ is as defined herein (e.g. acetyl chloride) preferably under anhydrous conditions and optionally in the presence of a catalyst such as CuCl, $AlC_{13}$, LiCl and mixtures thereof, to obtain compounds X. Alternatively, compounds IIIc

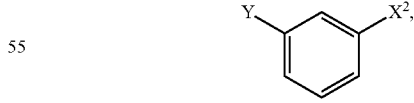

e.g. 1,3-dichlorobenzene of formula IIIb can be reacted with an acyl chloride agent IX wherein $R^1$ is as defined above (e.g. acetyl chloride) preferably in the presence of a catalyst such as $AlC_{13}$. Then, ketones X are reacted with phenoles II preferably in the presence of a base to obtain compounds Va. Compounds Va may also be obtained in analogy to the first process described for compounds V Thereafter, intermediates Va are reacted with trimethylsulf(ox)onium halides preferably iodide preferably in the presence of a base such as sodium hydroxide. Thereafter, the epoxides $X^1$ are reacted with 1H-1,2,4-triazole preferably in the presence of a base such as potassium carbonate and preferably in the presence of an organic solvent such as DMF to obtain compounds VIII. These compounds VIII are reacted with $R^2$-LG, wherein $R^2$ is as defined above and LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base to form compounds I., which can subsequently be alkylated as described above. The preparation of compounds I can be illustrated by the following scheme:

herein is cleaved by reaction with alcohols $R^2OH$ preferably under acidic conditions. Thereafter, the resulting compounds XII are reacted with halogenating agents or sulfonating agents such as $PBr_3$, $PCl_3$, mesyl chloride, tosyl chloride or thionyl chloride to obtain compounds XIII wherein LG is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds XIII are reacted with 1H-1,2,4-triazole to obtain compounds

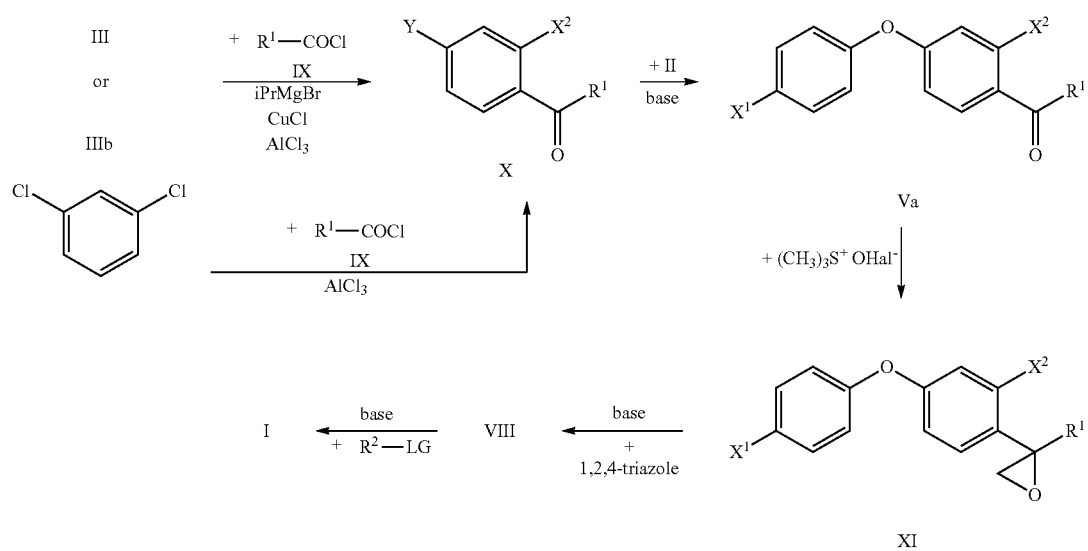

In a third process, the epoxide ring of intermediates $X^1$ which may be obtained according to the second process described I. The preparation of compounds I can be illustrated by the following scheme:

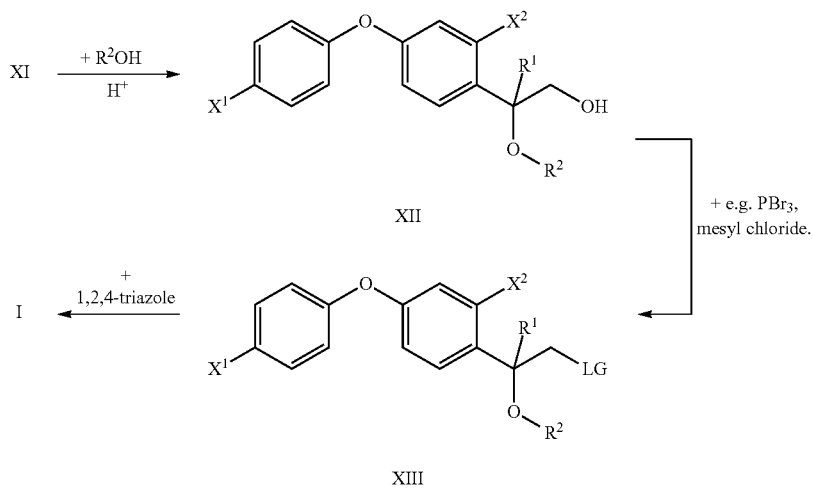

If individual compounds I cannot be obtained by the routes described above, they can be prepared by derivatization of other compounds I.

The N-oxides may be prepared from the compounds I according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during workup for use or during application (e.g. under the action of light, acids or bases). Such conversions may also take place after use, e.g. in the treatment of plants in the treated plant, or in the harmful fungus to be controlled.

In the following, the intermediate compounds are further described. A skilled person will readily understand that the preferences for the substituents given herein in connection with compounds I apply for the intermediates accordingly. Thereby, the substituents in each case have independently of each other or more preferably in combination the meanings as defined herein.

The present invention also relates to novel compounds of formula Va

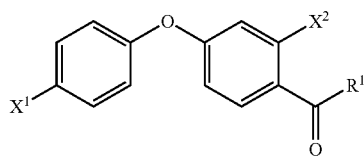

wherein the variables $R^1$, $X^1$, $X^2$ are as defined and preferably defined for formula I herein. In specific embodiments of compounds Va according to the present invention, the substituents $R^1$, $X^1$, $X^2$ are as defined in tables 1 to 84, tables 84a to 84x, tables 85 to 168, tables 168a to 168x, 169 to 252 and 252a to 252x for compounds I, wherein the substituents are specific embodiments independently of each other or in any combination.

A further embodiment of the present invention are novel compounds of formula VI:

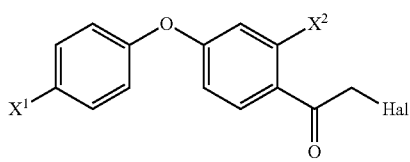

Wherein the variables $X^1$, $X^2$ are as defined and preferably defined for formula I herein, and wherein Hal stands for halogen, in particular Cl or Br. According to one preferred embodiment Hal in compounds VI stands for Br.

A further embodiment of the present invention are novel compounds of formula VII:

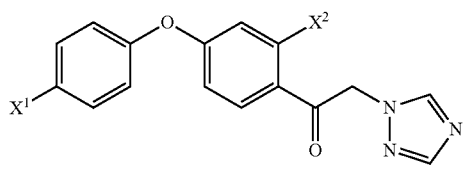

Wherein the variables $X^1$, $X^2$ are as defined and preferably defined for formula I herein. In specific embodiments of compounds VII according to the present invention, the substituents $X^1$, $X^2$ are as defined in tables 1 to 84, tables 84a to 84x, tables 85 to 168, tables 168a to 168x, 169 to 252 and 252a to 252x, wherein the substituents are specific embodiments independently of each other or in any combination.

A further embodiment of the present invention are novel compounds of formula VIII:

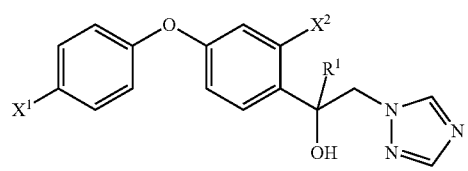

Wherein the variables $X^1$, $X^2$ and $R^1$ are as defined and preferably defined for formula I herein, with the exception 1) of compounds, wherein $X^1$ and $X^2$ are Cl and $R^1$ is $CH_2CH_3$, $CH_2CH_2CH_3$, $CH(CH_3)_2$, $CH_2CH_2CH_2CH_3$, $CH(CH_2CH_3)_2$, $C(CH_3)_3$, $CH_2CH(CH_3)_2$, $CH_2CH_2CH_2CH_2CH_3$, $CH_2CH_2CH_2CH_2CH_2CH_3$, $CH=CH_2$, $CH=CHCH_3$, $CH_2CH=CH_2$, $C(CH_3)=CH_2$, $CH=CHCH_2CH_3$, $CH_2CH=CHCH_3$, $CH_2CH_2CH=CH_2$, $CH(CH=CH_2)_2$, $CH=C(CH_3)_2$, $CH=CHCH_2CH_2CH_3$, $CH=CHCH_2CH_2CH_3$, $CH=CHC(CH_3)_3$, $C\equiv CH$, $C\equiv CCH_3$, $C\equiv CCH_2CH_3$, $CH_2C\equiv CCH_3$, $CH_2CH_2C\equiv CH$, $CH(C\equiv CH)_2$, $C\equiv CCH_2CH_2CH_3$, $C\equiv CCH(CH_3)_2$, $C\equiv CCH_2CH_2CH_2CH_3$, $C\equiv CC(CH_3)_3$, $C_3H_5$ (cyclopropyl), 1-Cl-cyclopropyl, 1-F-cyclopropyl, $C_4H_7$, $C_6H_{11}$ (cyclohexyl), $CH_2$—$C_3H_5$, $CH_2CN$, $CH_2CH_2CN$, $CH_2C(CH_3)=CH_2$, $C_5H_9$ (cyclopentyl), $CH(CH_3)CH_2CH_3$, $CH_2C\equiv CH$, $CH_2C\equiv CCH_2CH_3$, $CH(CH_3)C_3H_5$, 1-Methylcyclopropyl, 1-CN-cyclopropyl or $CH(CH_3)CN$; and 2) of compounds, wherein $X^1$ and $X^2$ are Cl and $R^1$ is a moiety $AR^1$

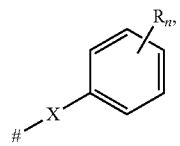

wherein:
 # denotes the attachment point to formula VIII,
 X is $C_1$-$C_4$-alkanediyl, $C_2$-$C_4$-alkynediyl or a bond;
 R is halogen, CN, nitro, $C_1$-$C_4$-alkyl, $C_1$-$C_4$-alkoxy, $C_1$-$C_4$-halogenalkyl or $C_1$-$C_4$-halogenalkoxy;
 n is an integer and is 0, 1, 2, 3, 4 or 5; and 3) of compounds, wherein $X^1$ is Cl or F and $X^2$ is Cl and $R^1$ is $CH_3$; and 4) of compounds, wherein $X^1$ is Cl or F and $X^2$ is Cl and $R^1$ is $CH_2OCH_3$; and 5) of compounds, wherein $X^1$ and $X^2$ are Cl and $R^1$ is $CH=CHC_6H_5$, $CH=CH(4\text{-}Cl-C_6H_4)$, $CH=CH(2,4\text{-}Cl_2-C_6H_3)$, $CH=CH(2,6\text{-}Cl_2-C_6H_3)$, $CH=CH(4\text{-}CH_3-C_6H_4)$, $CH=CH(4\text{-}OCH_3-C_6H_4)$, $CH=CH(3,4\text{-}Cl_2-C_6H_3)$, $CH=CH(2\text{-}F-C_6H_4)$, $CH=CH(4\text{-}NO_2-C_6H_4)$, $CH=CH(2\text{-}NO_2-C_6H_4)$, $CH=CH(2\text{-}Cl-C_6H_4)$, $CH=CH(4\text{-}F-C_6H_4)$ or $CH=CH(4\text{-}C_2H_5-C_6H_4)$; and 6) of compounds, wherein $X^1$ and $X^2$ are Cl and $R^1$ is $CH_2F$, $CH_2CCl_2CHCl_2$, $CH(OCH_3)_2$, $CH_2C\equiv CH$, $CH_2C(Br)=CHBr$, $CH_2CCl=CHCl$ or $CHF(CH_3)$.

According to one embodiment, the variables $X^1$, $X^2$ and $R^1$ are as defined and preferably defined for formula I herein, with the exception 1) of compounds, wherein $X^1$ and $X^2$ are Cl and $R^1$ is $C_2\text{-}C_6$-alkyl, $C_2\text{-}C_6$-alkenyl, $C_2\text{-}C_6$-alkynyl, $C_3\text{-}C_8$-cycloalkyl, $C_3\text{-}C_8$-cycloalkyl-$C_1\text{-}C_4$-alkyl; wherein the aliphatic groups $R^1$ are unsubstituted or carry 1, 2, 3 or 4 CN substituents; and wherein the cycloalkyl moieties of $R^1$ are unsubstituted or carry 1, 2, 3 or up to the maximum number of identical or different groups $R^b$ which independently of one another are selected from halogen, CN, nitro, $C_1\text{-}C_4$-alkyl, $C_1\text{-}C_4$-alkoxy, $C_1\text{-}C_4$-halogenalkyl and $C_1\text{-}C_4$-halogenalkoxy; and 2) of compounds, wherein $X^1$ and $X^2$ are Cl and $R^1$ is a moiety $AR^1$

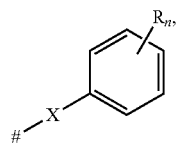

wherein:
# denotes the attachment point to formula VIII,
X is $C_1\text{-}C_4$-alkanediyl, $C_2\text{-}C_4$-alkynediyl or a bond;
R is halogen, CN, nitro, $C_1\text{-}C_4$-alkyl, $C_1\text{-}C_4$-alkoxy, $C_1\text{-}C_4$-halogenalkyl or $C_1\text{-}C_4$-halogenalkoxy;
n is an integer and is 0, 1, 2, 3, 4 or 5; and 3) of compounds, wherein $X^1$ is Cl or F and $X^2$ is Cl and $R^1$ is $CH_3$; and 4) of compounds, wherein $X^1$ is Cl or F and $X^2$ is Cl and $R^1$ is $CH_2OCH_3$; and 5) of compounds, wherein $X^1$ and $X^2$ are Cl and $R^1$ is $CH=CHC_6H_5$, $CH=CH(4\text{-}Cl-C_6H_4)$, $CH=CH(2,4\text{-}Cl_2-C_6H_3)$, $CH=CH(2,6\text{-}Cl_2-C_6H_3)$, $CH=CH(4\text{-}CH_3-C_6H_4)$, $CH=CH(4\text{-}OCH_3-C_6H_4)$, $CH=CH(3,4\text{-}Cl_2-C_6H_3)$, $CH=CH(2\text{-}F-C_6H_4)$, $CH=CH(4\text{-}NO_2-C_6H_4)$, $CH=CH(2\text{-}NO_2-C_6H_4)$, $CH=CH(2\text{-}Cl-C_6H_4)$, $CH=CH(4\text{-}F-C_6H_4)$ or $CH=CH(4\text{-}C_2H_5-C_6H_4)$; and 6) of compounds, wherein $X^1$ and $X^2$ are Cl and $R^1$ is $CH_2F$, $CH_2CCl_2CHCl_2$, $CH(OCH_3)_2$, $CH_2C\equiv CH$, $CH_2C(Br)=CHBr$, $CH_2CCl=CHCl$ or $CHF(CH_3)$.

According to one embodiment, in compounds VIII, $R^1$ is $C_1\text{-}C_6$-alkyl that is substituted by 1, 2 or 3 $C_1\text{-}C_4$-alkoxy taking into account the above proviso.

According to a further embodiment, in compounds VIII, $R^1$ is $C_1\text{-}C_6$-alkyl that is substituted by 1, 2, 3 or 4 halogen with the above proviso. According to a further embodiment, in compounds VIII, $R^1$ is $C_1\text{-}C_6$-alkyl that is substituted by at least 2 F, According to another embodiment, in compounds VIII $X^1$ and $X^2$ are not both Cl with the exception of compounds, wherein $X^1$ is F and $X^2$ is Cl and $R^1$ is $CH_3$ or $CH_2OCH_3$.

Compounds VIII are also suitable as fungicides as described herein for compounds of formula I. Specific preferred compounds VIII are the following C-1 to C-288, wherein each compound corresponds to one line of table C:

TABLE C

Compounds C-1 to C-288 of formula VIII:

| line | $X^1$ | $X^2$ | $R^1$ |
|---|---|---|---|
| C-1 | Cl | F | $CH_3$ |
| C-2 | F | F | $CH_3$ |
| C-3 | Cl | F | $CH_2CH_3$ |
| C-4 | F | Cl | $CH_2CH_3$ |
| C-5 | F | F | $CH_2CH_3$ |
| C-6 | Cl | F | $CH_2CH_2CH_3$ |
| C-7 | F | Cl | $CH_2CH_2CH_3$ |
| C-8 | F | F | $CH_2CH_2CH_3$ |
| C-9 | Cl | F | $CH(CH_3)_2$ |
| C-10 | F | Cl | $CH(CH_3)_2$ |
| C-11 | F | F | $CH(CH_3)_2$ |
| C-12 | Cl | F | $CH_2CH_2CH_2CH_3$ |
| C-13 | F | Cl | $CH_2CH_2CH_2CH_3$ |
| C-14 | F | F | $CH_2CH_2CH_2CH_3$ |
| C-15 | Cl | F | $C_3H_5$ (cyclopropyl) |
| C-16 | F | Cl | $C_3H_5$ (cyclopropyl) |
| C-17 | F | F | $C_3H_5$ (cyclopropyl) |
| C-18 | Cl | F | $C_5H_9$ (cyclopentyl) |
| C-19 | F | Cl | $C_5H_9$ (cyclopentyl) |
| C-20 | F | F | $C_5H_9$ (cyclopentyl) |
| C-21 | Cl | F | $C_6H_{11}$ (cyclohexyl) |
| C-22 | F | Cl | $C_6H_{11}$ (cyclohexyl) |
| C-23 | F | F | $C_6H_{11}$ (cyclohexyl) |
| C-24 | Cl | F | $C_6H_5$ |
| C-25 | F | Cl | $C_6H_5$ |
| C-26 | F | F | $C_6H_5$ |
| C-27 | Cl | F | $CH_2-C_6H_5$ |
| C-28 | F | Cl | $CH_2-C_6H_5$ |
| C-29 | F | F | $CH_2-C_6H_5$ |
| C-30 | Cl | F | $CH_2-C_3H_5$ |
| C-31 | F | Cl | $CH_2-C_3H_5$ |
| C-32 | F | F | $CH_2-C_3H_5$ |
| C-33 | Cl | Cl | $CF_3$ |
| C-34 | Cl | F | $CF_3$ |
| C-35 | F | Cl | $CF_3$ |
| C-36 | F | F | $CF_3$ |
| C-37 | Cl | Cl | $CHF_2$ |
| C-38 | Cl | F | $CHF_2$ |
| C-39 | F | Cl | $CHF_2$ |
| C-40 | F | F | $CHF_2$ |
| C-41 | Cl | F | $CH_2F$ |
| C-42 | F | Cl | $CH_2F$ |
| C-43 | F | F | $CH_2F$ |
| C-44 | Cl | F | $CH_2CN$ |
| C-45 | F | Cl | $CH_2CN$ |
| C-46 | F | F | $CH_2CN$ |
| C-47 | Cl | F | $CH_2CH_2CN$ |
| C-48 | F | Cl | $CH_2CH_2CN$ |
| C-49 | F | F | $CH_2CH_2-CN$ |
| C-50 | Cl | F | $C\equiv CH$ |
| C-51 | F | Cl | $C\equiv CH$ |
| C-52 | F | F | $C\equiv CH$ |
| C-53 | Cl | F | $C\equiv CCH_3$ |
| C-54 | F | Cl | $C\equiv CCH_3$ |
| C-55 | F | F | $C\equiv CCH_3$ |
| C-56 | Cl | F | $CH_2C\equiv CH$ |
| C-57 | F | Cl | $CH_2C\equiv CH$ |
| C-58 | F | F | $CH_2C\equiv CH$ |
| C-59 | Cl | F | 4-F—$C_6H_4$ |
| C-60 | F | Cl | 4-F—$C_6H_4$ |
| C-61 | F | F | 4-F—$C_6H_4$ |
| C-62 | Cl | F | 4-Cl—$C_6H_4$ |
| C-63 | F | Cl | 4-Cl—$C_6H_4$ |
| C-64 | F | F | 4-Cl—$C_6H_4$ |
| C-65 | Cl | F | 2,4-$Cl_2$—$C_6H_3$ |
| C-66 | F | Cl | 2,4-$Cl_2$—$C_6H_3$ |

TABLE C-continued

Compounds C-1 to C-288 of formula VIII:

| line | $X^1$ | $X^2$ | $R^1$ |
|---|---|---|---|
| C-67 | F | F | 2,4-$Cl_2$—$C_6H_3$ |
| C-68 | Cl | F | 2,4,6-$Cl_3$—$C_6H_2$ |
| C-69 | F | Cl | 2,4,6-$Cl_3$—$C_6H_2$ |
| C-70 | F | F | 2,4,6-$Cl_3$—$C_6H_2$ |
| C-71 | Cl | F | 2,4,6-$F_3$—$C_6H_2$ |
| C-72 | F | Cl | 2,4,6-$F_3$—$C_6H_2$ |
| C-73 | F | F | 2,4,6-$F_3$—$C_6H_2$ |
| C-74 | Cl | F | $CH_2$—$C_6H_5$ |
| C-75 | F | Cl | $CH_2$—$C_6H_5$ |
| C-76 | F | F | $CH_2$—$C_6H_5$ |
| C-77 | Cl | F | $CH_2$—(4-F—$C_6H_4$) |
| C-78 | F | Cl | $CH_2$—(4-F—$C_6H_4$) |
| C-79 | F | F | $CH_2$—(4-F—$C_6H_4$) |
| C-80 | Cl | F | $CH_2$—(4-Cl—$C_6H_4$) |
| C-81 | F | Cl | $CH_2$—(4-Cl—$C_6H_4$) |
| C-82 | F | F | $CH_2$—(4-Cl—$C_6H_4$) |
| C-83 | Cl | F | CH=CH—$C_6H_5$ |
| C-84 | F | Cl | CH=CH—$C_6H_5$ |
| C-85 | F | F | CH=CH—$C_6H_5$ |
| C-86 | Cl | F | CH=CH—(4-F—$C_6H_4$) |
| C-87 | F | Cl | CH=CH—(4-F—$C_6H_4$) |
| C-88 | F | F | CH=CH—(4-F—$C_6H_4$) |
| C-89 | Cl | F | CH=CH—(4-Cl—$C_6H_4$) |
| C-90 | F | Cl | CH=CH—(4-Cl—$C_6H_4$) |
| C-91 | F | F | CH=CH—(4-Cl—$C_6H_4$) |
| C-92 | Cl | F | $CH(CH_2CH_3)_2$ |
| C-93 | F | Cl | $CH(CH_2CH_3)_2$ |
| C-94 | F | F | $CH(CH_2CH_3)_2$ |
| C-95 | Cl | F | $C(CH_3)_2$ |
| C-96 | F | Cl | $C(CH_3)_2$ |
| C-97 | F | F | $C(CH_3)_2$ |
| C-98 | Cl | F | $CH_2CH(CH_3)_2$ |
| C-99 | F | Cl | $CH_2CH(CH_3)_2$ |
| C-100 | F | F | $CH_2CH(CH_3)_2$ |
| C-101 | Cl | F | $CH_2CH_2CH_2CH_2CH_3$ |
| C-102 | F | Cl | $CH_2CH_2CH_2CH_2CH_3$ |
| C-103 | F | F | $CH_2CH_2CH_2CH_2CH_3$ |
| C-104 | Cl | F | $CH_2CH_2CH_2CH_2CH_2CH_3$ |
| C-105 | F | Cl | $CH_2CH_2CH_2CH_2CH_2CH_3$ |
| C-106 | F | F | $CH_2CH_2CH_2CH_2CH_2CH_3$ |
| C-107 | Cl | F | CH=$CH_2$ |
| C-108 | F | Cl | CH=$CH_2$ |
| C-109 | F | F | CH=$CH_2$ |
| C-110 | Cl | F | CH=$CHCH_3$ |
| C-111 | F | Cl | CH=$CHCH_3$ |
| C-112 | F | F | CH=$CHCH_3$ |
| C-113 | Cl | F | $CH_2$CH=$CH_2$ |
| C-114 | F | Cl | $CH_2$CH=$CH_2$ |
| C-115 | F | F | $CH_2$CH=$CH_2$ |
| C-116 | Cl | F | $C(CH_3)$=$CH_2$ |
| C-117 | F | Cl | $C(CH_3)$=$CH_2$ |
| C-118 | F | F | $C(CH_3)$=$CH_2$ |
| C-119 | Cl | F | CH=$CHCH_2CH_3$ |
| C-120 | F | Cl | CH=$CHCH_2CH_3$ |
| C-121 | F | F | CH=$CHCH_2CH_3$ |
| C-122 | Cl | F | $CH_2$CH=$CHCH_3$ |
| C-123 | F | Cl | $CH_2$CH=$CHCH_3$ |
| C-124 | F | F | $CH_2$CH=$CHCH_3$ |
| C-125 | Cl | F | $CH_2CH_2$CH=$CH_2$ |
| C-126 | F | Cl | $CH_2CH_2$CH=$CH_2$ |
| C-127 | F | F | $CH_2CH_2$CH=$CH_2$ |
| C-128 | Cl | F | CH(CH=$CH_2)_2$ |
| C-129 | F | Cl | CH(CH=$CH_2)_2$ |
| C-130 | F | F | CH(CH=$CH_2)_2$ |
| C-131 | Cl | F | CH=$C(CH_3)_2$ |
| C-132 | F | Cl | CH=$C(CH3)_2$ |
| C-133 | F | F | CH=$C(CH_3)_2$ |
| C-134 | Cl | F | CH=$CHCH_2CH_2CH_3$ |
| C-135 | F | Cl | CH=$CHCH_2CH_2CH_3$ |
| C-136 | F | F | CH=$CHCH_2CH_2CH_3$ |
| C-137 | Cl | F | CH=$CHCH_2CH_2CH_2CH_3$ |
| C-138 | F | Cl | CH=$CHCH_2CH_2CH_2CH_3$ |
| C-139 | F | F | CH=$CHCH_2CH_2CH_2CH_3$ |
| C-140 | Cl | F | CH=$CHC(CH_3)_3$ |
| C-141 | F | Cl | CH=$CHC(CH_3)_3$ |
| C-142 | F | F | CH=$CHC(CH_3)_3$ |
| C-143 | Cl | F | C≡$CCH_2CH_3$ |
| C-144 | F | Cl | C≡$CCH_2CH_3$ |
| C-145 | F | F | C≡$CCH_2CH_3$ |
| C-146 | Cl | F | $CH_2$C≡$CCH3$ |
| C-147 | F | Cl | $CH_2$C≡$CCH3$ |
| C-148 | F | F | $CH_2$C≡$CCH3$ |
| C-149 | Cl | F | $CH_2CH_2$C≡CH |
| C-150 | F | Cl | $CH_2CH_2$C≡CH |
| C-151 | F | F | $CH_2CH_2$C≡CH |
| C-152 | Cl | F | CH(C≡CH)$_2$ |
| C-153 | F | Cl | CH(C≡CH)$_2$ |
| C-154 | F | F | CH(C≡CH)$_2$ |
| C-155 | Cl | F | C≡$CCH_2CH_2CH_3$ |
| C-156 | F | Cl | C≡$CCH_2CH_2CH_3$ |
| C-157 | F | F | C≡$CCH_2CH_2CH_3$ |
| C-158 | Cl | F | C≡$CCH(CH_3)_2$ |
| C-159 | F | Cl | C≡$CCH(CH_3)_2$ |
| C-160 | F | F | C≡$CCH(CH_3)_2$ |
| C-161 | Cl | F | C≡$CCH_2CH_2CH_2CH_3$ |
| C-162 | F | Cl | C≡$CCH_2CH_2CH_2CH_3$ |
| C-163 | F | F | C≡$CCH_2CH_2CH_2CH_3$ |
| C-164 | Cl | F | C≡$CC(CH_3)_3$ |
| C-165 | F | Cl | C≡$CC(CH_3)_3$ |
| C-166 | F | F | C≡$CC(CH_3)_3$ |
| C-167 | Cl | F | 1-Cl-cyclopropyl |
| C-168 | F | Cl | 1-Cl-cyclopropyl |
| C-169 | F | F | 1-Cl-cyclopropyl |
| C-170 | Cl | F | 1-F-cyclopropyl |
| C-171 | F | Cl | 1-F-cyclopropyl |
| C-172 | F | F | 1-F-cyclopropyl |
| C-173 | Cl | F | $CH_2C(CH_3)$=$CH_2$ |
| C-174 | F | Cl | $CH_2C(CH_3)$=$CH_2$ |
| C-175 | F | F | $CH_2C(CH_3)$=$CH_2$ |
| C-176 | Cl | F | $CH(CH_3)CH_2CH_3$ |
| C-177 | F | Cl | $CH(CH_3)CH_2CH_3$ |
| C-178 | F | F | $CH(CH_3)CH_2CH_3$ |
| C-179 | Cl | F | $CH_2$C≡$CCH_2CH_3$ |
| C-180 | F | Cl | $CH_2$C≡$CCH_2CH_3$ |
| C-181 | F | F | $CH_2$C≡$CCH_2CH_3$ |
| C-182 | Cl | F | $CH(CH_3)C_3H_5$ |
| C-183 | F | Cl | $CH(CH_3)C_3H_5$ |
| C-184 | F | F | $CH(CH_3)C_3H_5$ |
| C-185 | Cl | F | 1-$CH_3$-cyclopropyl |
| C-186 | F | Cl | 1-$CH_3$-cyclopropyl |
| C-187 | F | F | 1-$CH_3$-cyclopropyl |
| C-188 | Cl | F | 1-CN-cyclopropyl |
| C-189 | F | Cl | 1-CN-cyclopropyl |
| C-190 | F | F | 1-CN-cyclopropyl |
| C-191 | Cl | F | $CH(CH_3)$CN |
| C-192 | F | Cl | $CH(CH_3)$CN |
| C-193 | F | F | $CH(CH_3)$CN |
| C-194 | Cl | F | 4-$OCH_3$—$C_6H_4$ |
| C-195 | F | Cl | 4-$OCH_3$—$C_6H_4$ |
| C-196 | F | F | 4-$OCH_3$—$C_6H_4$ |
| C-197 | Cl | F | 4-$CH_3$—$C_6H_4$ |
| C-198 | F | Cl | 4-$CH_3$—$C_6H_4$ |
| C-199 | F | F | 4-$CH_3$—$C_6H_4$ |
| C-200 | Cl | F | $CH_2$—(4-$CH_3$—$C_6H_4$) |
| C-201 | F | Cl | $CH_2$—(4-$CH_3$—$C_6H_4$) |
| C-202 | F | F | $CH_2$—(4-$CH_3$—$C_6H_4$) |
| C-203 | Cl | F | $CH_2$—(4-$OCH_3$—$C_6H_4$) |
| C-204 | F | Cl | $CH_2$—(4-$OCH_3$—$C_6H_4$) |
| C-205 | F | F | $CH_2$—(4-$OCH_3$—$C_6H_4$) |
| C-206 | Cl | F | $CH_2$—(2,4-$Cl_2$—$C_6H_3$) |
| C-207 | F | Cl | $CH_2$—(2,4-$Cl_2$—$C_6H_3$) |
| C-208 | F | F | $CH_2$—(2,4-$Cl_2$—$C_6H_3$) |
| C-209 | Cl | F | $CH_2$—(2,4-$F_2$—$C_6H_3$) |
| C-210 | F | Cl | $CH_2$—(2,4-$F_2$—$C_6H_3$) |
| C-211 | F | F | $CH_2$—(2,4-$F_2$—$C_6H_3$) |
| C-212 | Cl | F | $CH_2OCH_3$ |
| C-213 | F | F | $CH_2OCH_3$ |
| C-214 | F | Cl | $CH_2OCH_2CH_3$ |
| C-215 | Cl | F | $CH_2OCH_2CH_3$ |
| C-216 | F | Cl | $CH_2OCH_2CH_3$ |
| C-217 | F | F | $CH_2OCH_2CH_3$ |
| C-218 | Cl | Cl | $CH(CH_3)OCH_3$ |

TABLE C-continued

Compounds C-1 to C-288 of formula VIII:

| line | $X^1$ | $X^2$ | $R^1$ |
|---|---|---|---|
| C-219 | Cl | F | $CH(CH_3)OCH_3$ |
| C-220 | F | Cl | $CH(CH_3)OCH_3$ |
| C-221 | F | F | $CH(CH_3)OCH_3$ |
| C-222 | Cl | Cl | $CH(CH_3)OCH_2CH_3$ |
| C-223 | Cl | F | $CH(CH_3)OCH_2CH_3$ |
| C-224 | F | Cl | $CH(CH_3)OCH_2CH_3$ |
| C-225 | F | F | $CH(CH_3)OCH_2CH_3$ |
| C-226 | Cl | Cl | $CH_2CH_2CF_3$ |
| C-227 | Cl | F | $CH_2CH_2CF_3$ |
| C-228 | F | Cl | $CH_2CH_2CF_3$ |
| C-229 | F | F | $CH_2CH_2CF_3$ |
| C-230 | Cl | Cl | $CH_2CH_2CH_2CF_3$ |
| C-231 | Cl | F | $CH_2CH_2CH_2CF_3$ |
| C-232 | F | Cl | $CH_2CH_2CH_2CF_3$ |
| C-233 | F | F | $CH_2CH_2CH_2CF_3$ |
| C-234 | Cl | Cl | $CH=CHCH_2OCH_3$ |
| C-235 | Cl | F | $CH=CHCH_2OCH_3$ |
| C-236 | F | Cl | $CH=CHCH_2OCH_3$ |
| C-237 | F | F | $CH=CHCH_2OCH_3$ |
| C-238 | Cl | Cl | $CH_2OCH_2CH_2CH_3$ |
| C-239 | Cl | F | $CH_2OCH_2CH_2CH_3$ |
| C-240 | F | Cl | $CH_2OCH_2CH_2CH_3$ |
| C-241 | F | F | $CH_2OCH_2CH_2CH_3$ |
| C-242 | Cl | Cl | $CH_2CH_2CH_2CN$ |
| C-243 | Cl | F | $CH_2CH_2CH_2CN$ |
| C-244 | F | Cl | $CH_2CH_2CH_2CN$ |
| C-245 | F | F | $CH_2CH_2CH_2CN$ |
| C-246 | Cl | Cl | $CH_2-C_6H_{11}$ |
| C-247 | Cl | F | $CH_2-C_6H_{11}$ |
| C-248 | F | Cl | $CH_2-C_6H_{11}$ |
| C-249 | F | F | $CH_2-C_6H_{11}$ |
| C-250 | Cl | Cl | $CH_2-C_5H_9$ |
| C-251 | Cl | F | $CH_2-C_5H_9$ |
| C-252 | F | Cl | $CH_2-C_5H_9$ |
| C-253 | F | F | $CH_2-C_5H_9$ |
| C-254 | Cl | Cl | $CH=CCl_2$ |
| C-255 | Cl | F | $CH=CCl_2$ |
| C-256 | F | Cl | $CH=CCl_2$ |
| C-257 | F | F | $CH=CCl_2$ |
| C-258 | Cl | F | $CH(CH_3)CN$ |
| C-259 | F | Cl | $CH(CH_3)CN$ |
| C-260 | F | F | $CH(CH_3)CN$ |
| C-261 | Cl | Cl | $CH=CHOCH_3$ |
| C-262 | Cl | F | $CH=CHOCH_3$ |
| C-263 | F | Cl | $CH=CHOCH_3$ |
| C-264 | F | F | $CH=CHOCH_3$ |
| C-265 | Cl | Cl | $C(CH_3)_2-C_3H_5$ |
| C-266 | Cl | F | $C(CH_3)_2-C_3H_5$ |
| C-267 | F | Cl | $C(CH_3)_2-C_3H_5$ |
| C-268 | F | F | $C(CH_3)_2-C_3H_5$ |
| C-269 | Cl | Cl | $CH_2C\equiv CCH(CH_3)_2$ |
| C-270 | Cl | F | $CH_2C\equiv CCH(CH_3)_2$ |
| C-271 | F | Cl | $CH_2C\equiv CCH(CH_3)_2$ |
| C-272 | F | F | $CH_2C\equiv CCH(CH_3)_2$ |
| C-273 | Cl | Cl | $CH_2C\equiv CC(CH_3)_3$ |
| C-274 | Cl | F | $CH_2C\equiv CC(CH_3)_3$ |
| C-275 | F | Cl | $CH_2C\equiv CC(CH_3)_3$ |
| C-276 | F | F | $CH_2C\equiv CC(CH_3)_3$ |
| C-277 | Cl | Cl | $CH_2C\equiv CCH_2OCH_3$ |
| C-278 | Cl | F | $CH_2C\equiv CCH_2OCH_3$ |
| C-279 | F | Cl | $CH_2C\equiv CCH_2OCH_3$ |
| C-280 | F | F | $CH_2C\equiv CCH_2OCH_3$ |
| C-281 | Cl | Cl | $CH_2CH_2OCH_3$ |
| C-282 | Cl | F | $CH_2CH_2OCH_3$ |
| C-283 | F | Cl | $CH_2CH_2OCH_3$ |
| C-284 | F | F | $CH_2CH_2OCH_3$ |
| C-285 | Cl | Cl | $CH_2CH(OCH_3)_2$ |
| C-286 | Cl | F | $CH_2CH(OCH_3)_2$ |
| C-287 | F | Cl | $CH_2CH(OCH_3)_2$ |
| C-288 | F | F | $CH_2CH(OCH_3)_2$ |

A further embodiment of the present invention are novel compounds of formula XI:

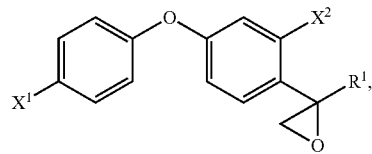

wherein the variables $X^1$, $X^2$ and $R^1$ are as defined and preferably defined for formula I herein, with the exception 1) of compounds, wherein $X^1$ and $X^2$ are Cl and $R^1$ is
—$CH_2CH_3$, —$CH_2CH_2CH_3$, $CH(CH_3)_2$, $CH_2CH_2CH_2CH_3$, $CH(CH_2CH_3)_2$, $C(CH_3)_3$, $CH_2CH(CH_3)_2$, $CH_2CH_2CH_2CH_2CH_3$, $CH_2CH_2CH_2CH_2CH_2CH_3$, $CH=CH_2$, $CH=CHCH_3$, $CH_2CH=CH_2$, $C(CH_3)=CH_2$, $CH=CHCH_2CH_3$, $CH_2CH=CHCH_3$, $CH_2CH_2CH=CH_2$, $CH(CH=CH_2)_2$, $CH=C(CH_3)_2$, $CH=CHCH_2CH_3$, $CH=CHCH_2CH_2CH_3$, $CH=CHC(CH_3)_3$, $C\equiv CH$, $C\equiv CCH_3$, $C\equiv CCH_2CH_3$, $CH_2C\equiv CCH_3$, $CH_2CH_2C\equiv CH$, $CH(C\equiv CH)_2$, $C\equiv CCH_2CH_3$, $C\equiv CCH(CH_3)_2$, $C\equiv CCH_2CH_2CH_2CH_3$, $C\equiv CC(CH_3)_3$, $C_3H_5$ (cyclopropyl), 1-Cl-cyclopropyl, 1-F-cyclopropyl, $C_4H_7$, $C_6H_{11}$ (cyclohexyl), $CH_2-C_3H_5$, $CH_2CN$, $CH_2CH_2CN$, $CH_2C(CH_3)=CH_2$, $C_5H_9$ (cyclopentyl), $CH(CH_3)CH_2CH_3$, $CH_2C\equiv CH$, $CH_2C\equiv CCH_2CH_3$, $CH(CH_3)C_3H_5$, 1-Methyl-cyclopropyl, 1-CN-cyclopropyl or $CH(CH_3)CN$; and 2) of compounds, wherein $X^1$ and $X^2$ are Cl and $R^1$ is a moiety $AR^1$

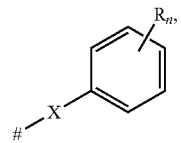

wherein:
# denotes the attachment point to formula VIII,
X is $C_1$-$C_4$-alkanediyl, $C_2$-$C_4$-alkynediyl or a bond;
R is halogen, CN, nitro, $C_1$-$C_4$-alkyl, $C_1$-$C_4$-alkoxy, $C_1$-$C_4$-halogenalkyl or $C_1$-$C_4$-halogenalkoxy;
n is an integer and is 0, 1, 2, 3, 4 or 5; and 3) of compounds, wherein $X^1$ is Cl or F and $X^2$ is Cl and $R^1$ is $CH_3$; and 4) of compounds, wherein $X^1$ is Cl or F and $X^2$ is Cl and $R^1$ is $CH_2OCH_3$; and 5) of compounds, wherein $X^1$ and $X^2$ are Cl and $R^1$ is $CH=CHC_6H_5$, $CH=CH(4$-$Cl$-$C_6H_4)$, $CH=CH(2,4$-$Cl_2$-$C_6H_3)$, $CH=CH(2,6$-$Cl_2$-$C_6H_3)$, $CH=CH(4$-$CH_3$-$C_6H_4)$, $CH=CH(4$-$OCH_3$-$C_6H_4)$, $CH=CH(3,4$-$Cl_2$-$C_6H_3)$, $CH=CH(2$-$F$-$C_6H_4)$, $CH=CH(4$-$NO_2$-$C_6H_4)$, $CH=CH(2$-$NO_2$-$C_6H_4)$, $CH=CH(2$-$Cl$-$C_6H_4)$, $CH=CH(4$-$F$-$C_6H_4)$ or $CH=CH(4$-$C_2H_5$-$C_6H_4)$; and 6) of compounds, wherein $X^1$ and $X^2$ are Cl and $R^1$ is $CH_2F$, $CH_2CCl_2CHCl_2$, $CH(OCH_3)_2$, $CH_2C\equiv CH$, $CH_2C(Br)=CHBr$, $CH_2CCl=CHCl$ or $CHF(CH_3)$.

According to one embodiment, the variables $X^1$, $X^2$ and $R^1$ are as defined and preferably defined for formula I herein, with the exception 1) of compounds, wherein $X^1$ and $X^2$ are Cl and $R^1$ is $C_2$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl; wherein the aliphatic groups $R^1$ are unsubstituted or carry 1, 2, 3 or 4 CN substituents; and wherein the cycloalkyl moieties of $R^1$ are unsubstituted or carry 1, 2, 3 or up to the maximum number of identical or different groups $R^b$ which independently of one another are selected from halogen, CN, nitro, $C_1$-$C_4$-alkyl, $C_1$-$C_4$-alkoxy, $C_1$-$C_4$-halogenalkyl and $C_1$-$C_4$-halogenalkoxy; and 2) of compounds, wherein $X^1$ and $X^2$ are Cl and $R^1$ is a moiety $AR^1$

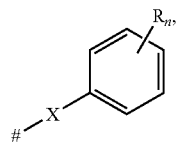

wherein:
# denotes the attachment point to formula VIII,
X is $C_1$-$C_4$-alkanediyl, $C_2$-$C_4$-alkynediyl or a bond;
R is halogen, CN, nitro, $C_1$-$C_4$-alkyl, $C_1$-$C_4$-alkoxy, $C_1$-$C_4$-halogenalkyl or $C_1$-$C_4$-halogenalkoxy;
n is an integer and is 0, 1, 2, 3, 4 or 5;
3) of compounds, wherein $X^1$ is Cl or F and $X^2$ is Cl and $R^1$ is $CH_3$; and
4) of compounds, wherein $X^1$ is Cl or F and $X^2$ is Cl and $R^1$ is $CH_2OCH_3$; and
5) of compounds, wherein $X^1$ and $X^2$ are Cl and $R^1$ is $CH=CHC_6H_5$, $CH=CH(4\text{-}Cl\text{---}C_6H_4)$, $CH=CH(2,4\text{-}Cl_2\text{---}C_6H_3)$, $CH=CH(2,6\text{-}Cl_2\text{---}C_6H_3)$, $CH=CH(4\text{-}CH_3\text{---}C_6H_4)$, $CH=CH(4\text{-}OCH_3\text{---}C_6H_4)$, $CH=CH(3,4\text{-}Cl_2\text{---}C_6H_3)$, $CH=CH(2\text{-}F\text{---}C_6H_4)$, $CH=CH(4\text{-}NO_2\text{---}C_6H_4)$, $CH=CH(2\text{-}NO_2\text{---}C_6H_4)$, $CH=CH(2\text{-}Cl\text{---}C_6H_4)$, $CH=CH(4\text{-}F\text{---}C_6H_4)$ or $CH=CH(4\text{-}C_2H_5\text{---}C_6H_4)$; and
6) of compounds, wherein $X^1$ and $X^2$ are Cl and $R^1$ is $CH_2F$, $CH_2CCl_2CHCl_2$, $CH(OCH_3)_2$, $CH_2C\equiv CH$, $CH_2C(Br)=CHBr$, $CH_2CCl=CHCl$ or $CHF(CH_3)$.

In particular embodiments, $R^1$ is defined as given for compounds VIII above.

In specific embodiments of compounds $X^1$ according to the present invention, the substituents $X^1$, $X^2$ and $R^1$ are as defined in tables 1 to 84, tables 84a to 84x, tables 85 to 168, tables 168a to 168x, 169 to 252 and 252a to 252x, wherein the substituents are specific embodiments independently of each other or in any combination.

Specific preferred compounds $X^1$ are the following D-1 to D-288, wherein each compound corresponds to one line of table D:

TABLE D

| Compounds D-1 to D-288 of formula XI: | | | |
|---|---|---|---|
| line | $X^1$ | $X^2$ | $R^1$ |
| D-1 | Cl | F | $CH_3$ |
| D-2 | F | F | $CH_3$ |
| D-3 | Cl | F | $CH_2CH_3$ |
| D-4 | F | Cl | $CH_2CH_3$ |
| D-5 | F | F | $CH_2CH_3$ |
| D-6 | Cl | F | $CH_2CH_2CH_3$ |
| D-7 | F | Cl | $CH_2CH_2CH_3$ |
| D-8 | F | F | $CH_2CH_2CH_3$ |
| D-9 | Cl | F | $CH(CH_3)_2$ |
| D-10 | F | Cl | $CH(CH_3)_2$ |
| D-11 | F | F | $CH(CH_3)_2$ |
| D-12 | Cl | F | $CH_2CH_2CH_2CH_3$ |
| D-13 | F | Cl | $CH_2CH_2CH_2CH_3$ |

TABLE D-continued

| Compounds D-1 to D-288 of formula XI: | | | |
|---|---|---|---|
| line | $X^1$ | $X^2$ | $R^1$ |
| D-14 | F | F | $CH_2CH_2CH_2CH_3$ |
| D-15 | Cl | F | $C_3H_5$ (cyclopropyl) |
| D-16 | F | Cl | $C_3H_5$ (cyclopropyl) |
| D-17 | F | F | $C_3H_5$ (cyclopropyl) |
| D-18 | Cl | F | $C_5H_9$ (cyclopentyl) |
| D-19 | F | Cl | $C_5H_9$ (cyclopentyl) |
| D-20 | F | F | $C_5H_9$ (cyclopentyl) |
| D-21 | Cl | F | $C_6H_{11}$ (cyclohexyl) |
| D-22 | F | Cl | $C_6H_{11}$ (cyclohexyl) |
| D-23 | F | F | $C_6H_{11}$ (cyclohexyl) |
| D-24 | Cl | F | $C_6H_5$ |
| D-25 | F | Cl | $C_6H_5$ |
| D-26 | F | F | $C_6H_5$ |
| D-27 | Cl | F | $CH_2\text{---}C_6H_5$ |
| D-28 | F | Cl | $CH_2\text{---}C_6H_5$ |
| D-29 | F | F | $CH_2\text{---}C_6H_5$ |
| D-30 | Cl | F | $CH_2\text{---}C_3H_5$ |
| D-31 | F | Cl | $CH_2\text{---}C_3H_5$ |
| D-32 | F | F | $CH_2\text{---}C_3H_5$ |
| D-33 | Cl | Cl | $CF_3$ |
| D-34 | Cl | F | $CF_3$ |
| D-35 | F | Cl | $CF_3$ |
| D-36 | F | F | $CF_3$ |
| D-37 | Cl | Cl | $CHF_2$ |
| D-38 | Cl | F | $CHF_2$ |
| D-39 | F | Cl | $CHF_2$ |
| D-40 | F | F | $CHF_2$ |
| D-41 | Cl | F | $CH_2F$ |
| D-42 | F | Cl | $CH_2F$ |
| D-43 | F | F | $CH_2F$ |
| D-44 | Cl | F | $CH_2CN$ |
| D-45 | F | Cl | $CH_2CN$ |
| D-46 | F | F | $CH_2CN$ |
| D-47 | Cl | F | $CH_2CH_2CN$ |
| D-48 | F | Cl | $CH_2CH_2CN$ |
| D-49 | F | F | $CH_2CH_2\text{---}CN$ |
| D-50 | Cl | F | $C\equiv CH$ |
| D-51 | F | Cl | $C\equiv CH$ |
| D-52 | F | F | $C\equiv CH$ |
| D-53 | Cl | F | $C\equiv CCH_3$ |
| D-54 | F | Cl | $C\equiv CCH_3$ |
| D-55 | F | F | $C\equiv CCH_3$ |
| D-56 | Cl | F | $CH_2C\equiv CH$ |
| D-57 | F | Cl | $CH_2C\equiv CH$ |
| D-58 | F | F | $CH_2C\equiv CH$ |
| D-59 | Cl | F | $4\text{-}F\text{---}C_6H_4$ |
| D-60 | F | Cl | $4\text{-}F\text{---}C_6H_4$ |
| D-61 | F | F | $4\text{-}F\text{---}C_6H_4$ |
| D-62 | Cl | F | $4\text{-}Cl\text{---}C_6H_4$ |
| D-63 | F | Cl | $4\text{-}Cl\text{---}C_6H_4$ |
| D-64 | F | F | $4\text{-}Cl\text{---}C_6H_4$ |
| D-65 | Cl | F | $2,4\text{-}Cl_2\text{---}C_6H_3$ |
| D-66 | F | Cl | $2,4\text{-}Cl_2\text{---}C_6H_3$ |
| D-67 | F | F | $2,4\text{-}Cl_2\text{---}C_6H_3$ |
| D-68 | Cl | F | $2,4,6\text{-}Cl_3\text{---}C_6H_2$ |
| D-69 | F | Cl | $2,4,6\text{-}Cl_3\text{---}C_6H_2$ |
| D-70 | F | F | $2,4,6\text{-}Cl_3\text{---}C_6H_2$ |
| D-71 | Cl | F | $2,4,6\text{-}F_3\text{---}C_6H_2$ |
| D-72 | F | Cl | $2,4,6\text{-}F_3\text{---}C_6H_2$ |
| D-73 | F | F | $2,4,6\text{-}F_3\text{---}C_6H_2$ |
| D-74 | Cl | F | $CH_2\text{---}C_6H_5$ |
| D-75 | F | Cl | $CH_2\text{---}C_6H_5$ |
| D-76 | F | F | $CH_2\text{---}C_6H_5$ |
| D-77 | Cl | F | $CH_2\text{---}(4\text{-}F\text{---}C_6H_4)$ |
| D-78 | F | Cl | $CH_2\text{---}(4\text{-}F\text{---}C_6H_4)$ |
| D-79 | F | F | $CH_2\text{---}(4\text{-}F\text{---}C_6H_4)$ |
| D-80 | Cl | F | $CH_2\text{---}(4\text{-}Cl\text{---}C_6H_4)$ |
| D-81 | F | Cl | $CH_2\text{---}(4\text{-}Cl\text{---}C_6H_4)$ |
| D-82 | F | F | $CH_2\text{---}(4\text{-}Cl\text{---}C_6H_4)$ |
| D-83 | Cl | F | $CH=CH\text{---}C_6H_5$ |
| D-84 | F | Cl | $CH=CH\text{---}C_6H_5$ |
| D-85 | F | F | $CH=CH\text{---}C_6H_5$ |
| D-86 | Cl | F | $CH=CH\text{---}(4\text{-}F\text{---}C_6H_4)$ |
| D-87 | F | Cl | $CH=CH\text{---}(4\text{-}F\text{---}C_6H_4)$ |
| D-88 | F | F | $CH=CH\text{---}(4\text{-}F\text{---}C_6H_4)$ |
| D-89 | Cl | F | $CH=CH\text{---}(4\text{-}Cl\text{---}C_6H_4)$ |

TABLE D-continued

Compounds D-1 to D-288 of formula XI:

| line | $X^1$ | $X^2$ | $R^1$ |
|---|---|---|---|
| D-90 | F | Cl | CH=CH—(4-Cl—$C_6H_4$) |
| D-91 | F | F | CH=CH—(4-Cl—$C_6H_4$) |
| D-92 | Cl | F | CH($CH_2CH_3$)$_2$ |
| D-93 | F | Cl | CH($CH_2CH_3$)$_2$ |
| D-94 | F | F | CH($CH_2CH_3$)$_2$ |
| D-95 | Cl | F | C($CH_3$)$_3$ |
| D-96 | F | Cl | C($CH_3$)$_3$ |
| D-97 | F | F | C($CH_3$)$_3$ |
| D-98 | Cl | F | $CH_2$CH($CH_3$)$_2$ |
| D-99 | F | Cl | $CH_2$CH($CH_3$)$_2$ |
| D-100 | F | F | $CH_2$CH($CH_3$)$_2$ |
| D-101 | Cl | F | $CH_2CH_2CH_2CH_2CH_3$ |
| D-102 | F | Cl | $CH_2CH_2CH_2CH_2CH_3$ |
| D-103 | F | F | $CH_2CH_2CH_2CH_2CH_3$ |
| D-104 | Cl | F | $CH_2CH_2CH_2CH_2CH_2CH_3$ |
| D-105 | F | Cl | $CH_2CH_2CH_2CH_2CH_2CH_3$ |
| D-106 | F | F | $CH_2CH_2CH_2CH_2CH_2CH_3$ |
| D-107 | Cl | F | CH=$CH_2$ |
| D-108 | F | Cl | CH=$CH_2$ |
| D-109 | F | F | CH=$CH_2$ |
| D-110 | Cl | F | CH=CH$CH_3$ |
| D-111 | F | Cl | CH=CH$CH_3$ |
| D-112 | F | F | CH=CH$CH_3$ |
| D-113 | Cl | F | $CH_2$CH=$CH_2$ |
| D-114 | F | Cl | $CH_2$CH=$CH_2$ |
| D-115 | F | F | $CH_2$CH=$CH_2$ |
| D-116 | Cl | F | C($CH_3$)=$CH_2$ |
| D-117 | F | Cl | C($CH_3$)=$CH_2$ |
| D-118 | F | F | C($CH_3$)=$CH_2$ |
| D-119 | Cl | F | CH=CH$CH_2CH_3$ |
| D-120 | F | Cl | CH=CH$CH_2CH_3$ |
| D-121 | F | F | CH=CH$CH_2CH_3$ |
| D-122 | Cl | F | $CH_2$CH=CH$CH_3$ |
| D-123 | F | Cl | $CH_2$CH=CH$CH_3$ |
| D-124 | F | F | $CH_2$CH=CH$CH_3$ |
| D-125 | Cl | F | $CH_2CH_2$CH=$CH_2$ |
| D-126 | F | Cl | $CH_2CH_2$CH=$CH_2$ |
| D-127 | F | F | $CH_2CH_2$CH=$CH_2$ |
| D-128 | Cl | F | CH(CH=$CH_2$)$_2$ |
| D-129 | F | Cl | CH(CH=$CH_2$)$_2$ |
| D-130 | F | F | CH(CH=$CH_2$)$_2$ |
| D-131 | Cl | F | CH=C($CH_3$)$_2$ |
| D-132 | F | Cl | CH=C($CH_3$)$_2$ |
| D-133 | F | F | CH=C($CH_3$)$_2$ |
| D-134 | Cl | F | CH=CH$CH_2CH_2CH_3$ |
| D-135 | F | Cl | CH=CH$CH_2CH_2CH_3$ |
| D-136 | F | F | CH=CH$CH_2CH_2CH_3$ |
| D-137 | Cl | F | CH=CH$CH_2CH_2CH_2CH_3$ |
| D-138 | F | Cl | CH=CH$CH_2CH_2CH_2CH$ |
| D-139 | F | F | CH=CH$CH_2CH_2CH_2CH$ |
| D-140 | Cl | F | CH=CHC($CH_3$)$_3$ |
| D-141 | F | Cl | CH=CHC($CH_3$)$_3$ |
| D-142 | F | F | CH=CHC($CH_3$)$_3$ |
| D-143 | Cl | F | C≡C$CH_2CH_3$ |
| D-144 | F | Cl | C≡C$CH_2CH_3$ |
| D-145 | F | F | C≡C$CH_2CH_3$ |
| D-146 | Cl | F | $CH_2$C≡C$CH_3$ |
| D-147 | F | Cl | $CH_2$C≡C$CH_3$ |
| D-148 | F | F | $CH_2$C≡C$CH_3$ |
| D-149 | Cl | F | $CH_2CH_2$C≡CH |
| D-150 | F | Cl | $CH_2CH_2$C≡CH |
| D-151 | F | F | $CH_2CH_2$C≡CH |
| D-152 | Cl | F | CH(C≡CH)$_2$ |
| D-153 | F | Cl | CH(C≡CH)$_2$ |
| D-154 | F | F | CH(C≡CH)$_2$ |
| D-155 | Cl | F | C≡C$CH_2CH_2CH_3$ |
| D-156 | F | Cl | C≡C$CH_2CH_2CH_3$ |
| D-157 | F | F | C≡C$CH_2CH_2CH_3$ |
| D-158 | Cl | F | C≡CCH($CH_3$)$_2$ |
| D-159 | F | Cl | C≡CCH($CH_3$)$_2$ |
| D-160 | F | F | C≡CCH($CH_3$)$_2$ |
| D-161 | Cl | F | C≡C$CH_2CH_2CH_2CH_3$ |
| D-162 | F | Cl | C≡C$CH_2CH_2CH_2CH_3$ |
| D-163 | F | F | C≡C$CH_2CH_2CH_2CH_3$ |
| D-164 | Cl | F | C≡CC($CH_3$)$_3$ |
| D-165 | F | Cl | C≡CC($CH_3$)$_3$ |
| D-166 | F | F | C≡CC($CH_3$)$_3$ |
| D-167 | Cl | F | 1-Cl-cyclopropyl |
| D-168 | F | Cl | 1-Cl-cyclopropyl |
| D-169 | F | F | 1-Cl-cyclopropyl |
| D-170 | Cl | F | 1-F-cyclopropyl |
| D-171 | F | Cl | 1-F-cyclopropyl |
| D-172 | F | F | 1-F-cyclopropyl |
| D-173 | Cl | F | $CH_2$C($CH_3$)=$CH_2$ |
| D-174 | F | Cl | $CH_2$C($CH_3$)=$CH_2$ |
| D-175 | F | F | $CH_2$C($CH_3$)=$CH_2$ |
| D-176 | Cl | F | CH($CH_3$)$CH_2CH_3$ |
| D-177 | F | Cl | CH($CH_3$)$CH_2CH_3$ |
| D-178 | F | F | CH($CH_3$)$CH_2CH_3$ |
| D-179 | Cl | F | $CH_2$C≡C$CH_2CH_3$ |
| D-180 | F | Cl | $CH_2$C≡C$CH_2CH_3$ |
| D-181 | F | F | $CH_2$C≡C$CH_2CH_3$ |
| D-182 | Cl | F | CH($CH_3$)$C_3H_5$ |
| D-183 | F | Cl | CH($CH_3$)$C_3H_5$ |
| D-184 | F | F | CH($CH_3$)$C_3H_5$ |
| D-185 | Cl | F | 1-$CH_3$-cyclopropyl |
| D-186 | F | Cl | 1-$CH_3$-cyclopropyl |
| D-187 | F | F | 1-$CH_3$-cyclopropyl |
| D-188 | Cl | F | 1-CN-cyclopropyl |
| D-189 | F | Cl | 1-CN-cyclopropyl |
| D-190 | F | F | 1-CN-cyclopropyl |
| D-191 | Cl | F | CH($CH_3$)CN |
| D-192 | F | Cl | CH($CH_3$)CN |
| D-193 | F | F | CH($CH_3$)CN |
| D-194 | Cl | F | 4-$OCH_3$—$C_6H_4$ |
| D-195 | F | Cl | 4-$OCH_3$—$C_6H_4$ |
| D-196 | F | F | 4-$OCH_3$—$C_6H_4$ |
| D-197 | Cl | F | 4-$CH_3$—$C_6H_4$ |
| D-198 | F | Cl | 4-$CH_3$—$C_6H_4$ |
| D-199 | F | F | 4-$CH_3$—$C_6H_4$ |
| D-200 | Cl | F | $CH_2$—(4-$CH_3$—$C_6H_4$) |
| D-201 | F | Cl | $CH_2$—(4-$CH_3$—$C_6H_4$) |
| D-202 | F | F | $CH_2$—(4-$CH_3$—$C_6H_4$) |
| D-203 | Cl | F | $CH_2$—(4-$OCH_3$—$C_6H_4$) |
| D-204 | F | Cl | $CH_2$—(4-$OCH_3$—$C_6H_4$) |
| D-205 | F | F | $CH_2$—(4-$OCH_3$—$C_6H_4$) |
| D-206 | Cl | F | $CH_2$—(2,4-$Cl_2$—$C_6H_3$) |
| D-207 | F | Cl | $CH_2$—(2,4-$Cl_2$—$C_6H_3$) |
| D-208 | F | F | $CH_2$—(2,4-$Cl_2$—$C_6H_3$) |
| D-209 | Cl | F | $CH_2$—(2,4-$F_2$—$C_6H_3$) |
| D-210 | F | Cl | $CH_2$—(2,4-$F_2$—$C_6H_3$) |
| D-211 | F | F | $CH_2$—(2,4-$F_2$—$C_6H_3$) |
| D-212 | Cl | F | $CH_2OCH_3$ |
| D-213 | F | F | $CH_2OCH_3$ |
| D-214 | Cl | Cl | $CH_2OCH_2CH_3$ |
| D-215 | Cl | F | $CH_2OCH_2CH_3$ |
| D-216 | F | Cl | $CH_2OCH_2CH_3$ |
| D-217 | F | F | $CH_2OCH_2CH_3$ |
| D-218 | Cl | Cl | CH($CH_3$)$OCH_3$ |
| D-219 | Cl | F | CH($CH_3$)$OCH_3$ |
| D-220 | F | Cl | CH($CH_3$)$OCH_3$ |
| D-221 | F | F | CH($CH_3$)$OCH_3$ |
| D-222 | Cl | Cl | CH($CH_3$)$OCH_2CH_3$ |
| D-223 | Cl | F | CH($CH_3$)$OCH_2CH_3$ |
| D-224 | F | Cl | CH($CH_3$)$OCH_2CH_3$ |
| D-225 | F | F | CH($CH_3$)$OCH_2CH_3$ |
| D-226 | Cl | Cl | $CH_2CH_2CF_3$ |
| D-227 | Cl | F | $CH_2CH_2CF_3$ |
| D-228 | F | Cl | $CH_2CH_2CF_3$ |
| D-229 | F | F | $CH_2CH_2CF_3$ |
| D-230 | Cl | Cl | $CH_2CH_2CH_2CF_3$ |
| D-231 | Cl | F | $CH_2CH_2CH_2CF_3$ |
| D-232 | F | Cl | $CH_2CH_2CH_2CF_3$ |
| D-233 | F | F | $CH_2CH_2CH_2CF_3$ |
| D-234 | Cl | Cl | CH=CH$CH_2OCH_3$ |
| D-235 | Cl | F | CH=CH$CH_2OCH_3$ |
| D-236 | F | Cl | CH=CH$CH_2OCH_3$ |
| D-237 | F | F | CH=CH$CH_2OCH_3$ |
| D-238 | Cl | Cl | $CH_2OCH_2CH_2CH_3$ |
| D-239 | Cl | F | $CH_2OCH_2CH_2CH_3$ |
| D-240 | F | Cl | $CH_2OCH_2CH_2CH_3$ |
| D-241 | F | F | $CH_2OCH_2CH_2CH_3$ |

TABLE D-continued

Compounds D-1 to D-288 of formula XI:

| line | $X^1$ | $X^2$ | $R^1$ |
|---|---|---|---|
| D-242 | Cl | Cl | CH$_2$CH$_2$CH$_2$CN |
| D-243 | Cl | F | CH$_2$CH$_2$CH$_2$CN |
| D-244 | F | Cl | CH$_2$CH$_2$CH$_2$CN |
| D-245 | F | F | CH$_2$CH$_2$CH$_2$CN |
| D-246 | Cl | Cl | CH$_2$—C$_6$H$_{11}$ |
| D-247 | Cl | F | CH$_2$—C$_6$H$_{11}$ |
| D-248 | F | Cl | CH$_2$—C$_6$H$_{11}$ |
| D-249 | F | F | CH$_2$—C$_6$H$_{11}$ |
| D-250 | Cl | Cl | CH$_2$—C$_5$H$_9$ |
| D-251 | Cl | F | CH$_2$—C$_5$H$_9$ |
| D-252 | F | Cl | CH$_2$—C$_5$H$_9$ |
| D-253 | F | F | CH$_2$—C$_5$H$_9$ |
| D-254 | Cl | Cl | CH=CCl$_2$ |
| D-255 | Cl | F | CH=CCl$_2$ |
| D-256 | F | Cl | CH=CCl$_2$ |
| D-257 | F | F | CH=CCl$_2$ |
| D-258 | Cl | Cl | CH(CH$_3$)CN |
| D-259 | Cl | F | CH(CH$_3$)CN |
| D-260 | F | F | CH(CH$_3$)CN |
| D-261 | Cl | Cl | CH=CHOCH$_3$ |
| D-262 | Cl | F | CH=CHOCH$_3$ |
| D-263 | F | Cl | CH=CHOCH$_3$ |
| D-264 | F | F | CH=CHOCH$_3$ |
| D-265 | Cl | Cl | C(CH$_3$)$_2$—C$_3$H$_5$ |
| D-266 | Cl | F | C(CH$_3$)$_2$—C$_3$H$_5$ |
| D-267 | F | Cl | C(CH$_3$)$_2$—C$_3$H$_5$ |
| D-268 | F | F | C(CH$_3$)$_2$—C$_3$H$_5$ |
| D-269 | Cl | Cl | CH$_2$C≡CCH(CH$_3$)$_2$ |
| D-270 | Cl | F | CH$_2$C≡CCH(CH$_3$)$_2$ |
| D-271 | F | Cl | CH$_2$C≡CCH(CH$_3$)$_2$ |
| D-272 | F | F | CH$_2$C≡CCH(CH$_3$)$_2$ |
| D-273 | Cl | Cl | CH$_2$C≡CC(CH$_3$)$_3$ |
| D-274 | Cl | F | CH$_2$C≡CC(CH$_3$)$_3$ |
| D-275 | F | Cl | CH$_2$C≡CC(CH$_3$)$_3$ |
| D-276 | F | F | CH$_2$C≡CC(CH$_3$)$_3$ |
| D-277 | Cl | Cl | CH$_2$C≡CCH$_2$OCH$_3$ |
| D-278 | Cl | F | CH$_2$C≡CCH$_2$OCH$_3$ |
| D-279 | F | Cl | CH$_2$C≡CCH$_2$OCH$_3$ |
| D-280 | F | F | CH$_2$C≡CCH$_2$OCH$_3$ |
| D-281 | Cl | Cl | CH$_2$CH$_2$OCH$_3$ |
| D-282 | Cl | F | CH$_2$CH$_2$OCH$_3$ |
| D-283 | F | Cl | CH$_2$CH$_2$OCH$_3$ |
| D-284 | F | F | CH$_2$CH$_2$OCH$_3$ |
| D-285 | Cl | Cl | CH$_2$CH(OCH$_3$)$_2$ |
| D-286 | Cl | F | CH$_2$CH(OCH$_3$)$_2$ |
| D-287 | F | Cl | CH$_2$CH(OCH$_3$)$_2$ |
| D-288 | F | F | CH$_2$CH(OCH$_3$)$_2$ |

A further embodiment of the present invention are novel compounds of formula XII:

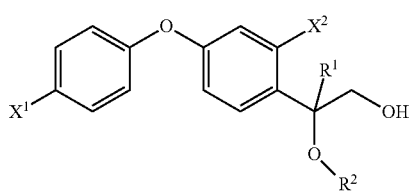

XII

Wherein the variables $X^1$, $X^2$, $R^1$ and $R^2$ are as defined and preferably defined for formula I herein. In specific embodiments of compounds XII according to the present invention, the substituents $X^1$, $X^2$, $R^1$ and $R^2$ are as defined in tables 1 to 84, tables 84a to 84x, tables 85 to 168, tables 168a to 168x, 169 to 252 and 252a to 252x, wherein the substituents are specific embodiments independently of each other or in any combination.

A further embodiment of the present invention are novel compounds of formula XIII:

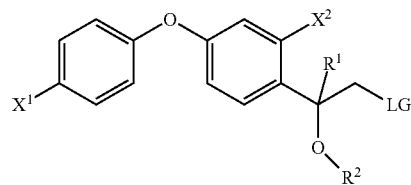

XIII

Wherein the variables $X^1$, $X^2$, $R^1$ and $R^2$ are as defined and preferably defined for formula I herein, wherein LG stands for a leaving group as defined above. In specific embodiments of compounds XIII according to the present invention, the substituents $X^1$, $X^2$, $R^1$ and $R^2$ are as defined in tables 1 to 84, tables 84a to 84x, tables 85 to 168, tables 168a to 168x, 169 to 252 and 252a to 252x, wherein the substituents are specific embodiments independently of each other or in any combination.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, prop-1-ynyl, prop-2-ynyl (propargyl), but-1-ynyl, but-2-ynyl, but-3-ynyl, 1-methyl-prop-2-ynyl. Likewise, the term "$C_2$-$C_6$-alkynyl" refers to a straight-chain or branched unsaturated hydrocarbon radical having 2 to 6 carbon atoms and at least one triple bond.

The term "$C_1$-$C_4$-halogenalkyl" refers to a straight-chained or branched alkyl group having 1 to 4 carbon atoms, wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-fluoromethyl-2-fluoroethyl, 1-(chloromethyl)-2-chloroethyl, 1-bromomethyl-2-bromoethyl, 4-fluorobutyl, 4-chlorobutyl, 4-bromobutyl or nonafluorobutyl, and the like.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_4$-alkoxy" refers to a straight-chain or branched alkyl group having 1 to 4 carbon atoms which is bonded via an oxygen, at any position in the alkyl group, e.g. methoxy, ethoxy, n-propoxy, 1-methylethoxy, butoxy, 1-methylpropoxy, 2-methylpropoxy or 1,1-dimethylethoxy.

The term "$C_1$-$C_4$-halogenalkoxy" refers to a $C_1$-$C_4$-alkoxy radical as defined above, wherein some or all of the hydrogen atoms in these groups may be replaced by halogen atoms as mentioned above, e.g., $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "phenyl-$C_1$-$C_4$-alkyl" refers to alkyl having 1 to 4 carbon atoms (as defined above), wherein one hydrogen atom of the alkyl radical is replaced by a phenyl radical. Likewise, the terms "phenyl-$C_2$-$C_4$-alkenyl" and "phenyl-$C_2$-$C_4$-alkynyl" refer to alkenyl and alkynyl, respectively, wherein one hydrogen atom of the aforementioned radicals is replaced by a phenyl radical.

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae such as I.A provided herein and to the intermediates such as compounds VIII, XI, XII and XIII, wherein the substituents (such as $X^1$, $X^2$, $R^1$, $R^2$, $R^a$ and $R^b$) have independently of each other or more preferably in combination the following meanings:

According to the invention, $X^1$ and $X^2$ are independently selected from halogen.

One embodiment relates to compounds I, wherein $X^1$ is F or Cl, in particular Cl.

Another embodiment relates to compounds I, wherein $X^2$ is F or Cl, in particular Cl.

According to the invention, $R^1$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl. The aliphatic moieties of $R^1$ may carry 1, 2, 3 or up to the maximum possible number of identical or different groups $R^a$ which independently of one another are selected from: halogen, CN, nitro, $C_1$-$C_4$-alkoxy and $C_1$-$C_4$-halogenalkoxy. The cycloalkyl and/or phenyl moieties of $R^1$ may carry 1, 2, 3, 4, 5 or up to the maximum number of identical or different groups $R^b$ which independently of one another are selected from halogen, CN, nitro, $C_1$-$C_4$-alkyl, $C_1$-$C_4$-alkoxy, $C_1$-$C_4$-halogenalkyl and $C_1$-$C_4$-halogenalkoxy.

According to one embodiment, $R^1$ is $C_1$-$C_6$-alkyl, in particular $C_1$-$C_4$-alkyl. According to specific embodiments, $R^1$ is methyl, ethyl, isopropyl, n-butyl or n-propyl. According to one embodiment, the alkyl is unsubstituted, according to a further embodiment, the alkyl carries 1, 2, 3, 4 or 5, in particular 1, 2 or 3, identical or different groups $R^a$ which independently of one another are selected from F, Cl, Br, CN, $C_1$-$C_2$-alkoxy and $C_1$-$C_2$-halogenalkoxy. According to a specific embodiment, $R^1$ is $C_1$-$C_2$-alkyl, substituted by 1, 2 or 3 halogen independently selected from Cl and F, such as for example $CF_3$. According to a further embodiment, $R^1$ is $C_1$-$C_6$-alkyl that is substituted by at least 2 F.

According to a further embodiment, $R^1$ is $C_2$-$C_6$-alkenyl, in particular $C_2$-$C_4$-alkenyl. According to one embodiment, the alkenyl is unsubstituted, according to a further embodiment, the alkenyl carries 1, 2, 3, 4 or 5, in particular 1, 2 or 3, identical or different groups $R^a$ which independently of one another are selected from F, Cl, Br, CN, $C_1$-$C_2$-alkoxy and $C_1$-$C_2$-halogenalkoxy.

According to a further embodiment, $R^1$ is $C_2$-$C_6$-alkynyl, in particular $C_2$-$C_4$-alkynyl. According to one embodiment, the alkynyl is unsubstituted, according to a further embodiment, the alkynyl carries 1, 2, 3, 4 or 5, in particular 1, 2 or 3, identical or different groups $R^a$ which independently of one another are selected from F, Cl, Br, CN, $C_1$-$C_2$-alkoxy and $C_1$-$C_2$-halogenalkoxy.

According to a further embodiment, $R^1$ is phenyl. According to one embodiment, the phenyl is unsubstituted, according to another embodiment, the phenyl carries 1, 2, 3, 4 or 5, in particular 1, 2 or 3, identical or different groups $R^b$ which independently of one another are selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy.

According to a further embodiment, $R^1$ is phenyl-$C_1$-$C_4$-alkyl, in particular phenyl-$C_1$-$C_2$-alkyl. A specific embodiment is benzyl. According to one embodiment, the phenyl is unsubstituted, according to another embodiment, the phenyl carries 1, 2, 3, 4 or 5, in particular 1, 2 or 3, identical or different groups $R^b$ which independently of one another are selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy. According to one embodiment, the alkyl is unsubstituted, according to a further embodiment, the alkyl carries 1, 2, 3, 4 or 5, in particular 1, 2 or 3, identical or different groups $R^a$ which independently of one another are selected from F, Cl, Br, CN, $C_1$-$C_2$-alkoxy and $C_1$-$C_2$-halogenalkoxy.

A further embodiment relates to compounds I, wherein $R^1$ is $C_1$-$C_4$-alkyl, allyl, $C_2$-$C_4$-alkynyl, cyclopropyl, cyclopropylmethyl, phenyl, benzyl, phenylethenyl or phenylethynyl, more preferably r $C_1$-$C_4$-alkyl, in particular methyl, ethyl, i-propyl, n-butyl or n-propyl.

A further embodiment relates to compounds I, wherein $R^1$ is $C_1$-$C_4$-alkyl, allyl, $C_2$-$C_4$-alkynyl, cyclopropyl, cyclopropylmethyl, phenyl, benzyl, phenylethenyl or phenylethynyl, wherein the aforementioned groups may be substituted by $R^a$ and/or $R^b$ as defined above, more preferably they carry 1, 2 or 3 halogen substituents, even more preferably $R^1$ is $C_1$-$C_2$-haloalkyl, in particular $R^1$ is $CF_3$.

According to a further embodiment, $R^1$ is $C_3$-$C_8$-cycloalkyl, in particular $C_3$-$C_6$-cycloalkyl. According to specific embodiments, $R^1$ is cyclopropyl, cyclopentyl or cyclohexyl. According to one embodiment, the cycloalkyl is unsubstituted, according to another embodiment, the cycloalkyl carries 1, 2, 3, 4 or 5, in particular 1, 2 or 3, identical or different groups $R^b$ which independently of one another are selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy. According to specific embodiments, $R^1$ is cyclopropyl, 1-Cl-cyclopropyl, 1-F-cyclopropyl, 1-$CH_3$-cyclopropyl or 1-CN-cyclopropyl.

According to a further embodiment, $R^1$ is $C_3$-$C_8$-cycloalkyl-$C_1$-$C_4$-alkyl, in particular $C_3$-$C_6$-cycloalkyl-$C_1$-$C_4$-alkyl. According to one embodiment, the cycloalkyl moiety is unsubstituted, according to another embodiment, the cycloalkyl moiety is substituted by 1, 2, 3, 4 or 5, in particular 1, 2 or 3, identical or different groups $R^b$ which independently of one another are selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy. According to one embodiment, the alkyl moiety is unsubstituted, according to another embodiment, the alkyl moiety is substituted by 1, 2, 3, 4 or 5, in particular 1, 2 or 3, identical or different groups $R^a$ which independently of one another are selected from F, Cl, Br, CN, $C_1$-$C_2$-alkoxy and $C_1$-$C_2$-halogenalkoxyl.

A further embodiment relates to compounds I, wherein $R^1$ is $C_3$-$C_8$-cycloalkyl or $C_3$-$C_8$-cycloalkyl-$C_1$-$C_4$-alkyl, more preferably selected from cyclopropyl, cyclopentyl, cyclohexyl and cyclopropylmethyl, wherein the aforementioned groups may be substituted by $R^a$ and/or $R^b$ as defined herein.

According to a further embodiment, $R^1$ is unsubstituted.

According to the invention, $R^2$ is $C_3$-$C_8$-cycloalkyl, phenyl, phenyl-$C_1$-$C_4$-alkyl, phenyl-$C_2$-$C_4$-alkenyl or phenyl-$C_2$-$C_4$-alkynyl; wherein the aliphatic moieties are unsubstituted or carry 1, 2, 3 or up to the maximum possible number of identical or different groups $R^a$ which independently of one another are selected from halogen, CN, nitro, $C_1$-$C_4$-alkoxy and $C_1$-$C_4$-halogenalkoxy, and wherein the cycloalkyl and/or phenyl moieties of $R^2$ may carry 1, 2, 3, 4, 5 or up to the maximum number of identical or different groups $R^b$ which independently of one another are selected from halogen, CN, nitro, $C_1$-$C_4$-alkyl, $C_1$-$C_4$-alkoxy, $C_1$-$C_4$-halogenalkyl and $C_1$-$C_4$-halogenalkoxy.

According to one embodiment, $R^2$ is $C_3$-$C_8$-cycloalkyl, in particular $C_3$-$C_6$-cycloalkyl. Specific embodiments relate to compounds, wherein $R^2$ is cyclopropyl. According to one embodiment, the cycloalkyl is unsubstituted, according to another embodiment, the cycloalkyl carries 1, 2, 3, 4, 5 or 6, in particular 1, 2, 3 or 4, $R^b$, wherein $R^b$ is selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy.

According to a further embodiment, $R^2$ is $C_3$-$C_8$-cycloalkyl-$C_1$-$C_4$-alkyl, in particular $C_3$-$C_6$-cycloalkyl-$C_1$-$C_4$-alkyl. Specific embodiments relate to compounds, wherein $R^2$ is cyclopropylmethyl. According to one embodiment, the cycloalkyl moiety is unsubstituted, according to another embodiment, the cycloalkyl moiety carries 1, 2, 3, 4, 5 or 6, in particular 1, 2, 3 or 4, $R^b$, wherein $R^b$ is selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy. According to a further embodiment, the alkyl moiety is unsubstituted, according to another embodiment, the alkyl moiety carries 1, 2, 3, 4, 5 or 6, in particular 1, 2, 3 or 4, $R^a$, wherein $R^a$ is selected from F, Cl, Br, CN, $C_1$-$C_2$-alkoxy and $C_1$-$C_2$-halogenalkoxy.

A further embodiment relates to compounds I, wherein $R^2$ is $C_3$-$C_6$-cycloalkyl or $C_3$-$C_6$-cycloalkyl-$C_1$-$C_4$-alkyl, more preferably selected from cyclopropyl, and cyclopropylmethyl, wherein the aforementioned groups may be substituted by $R^a$ and/or $R^b$ as defined above.

A further embodiment relates to compounds I, wherein $R^2$ is phenyl, wherein the aforementioned groups may be substituted by $R^b$ as defined above, more preferably they carry 1, 2 or 3 halogen substituents, in particular selected from Cl and F.

A further embodiment relates to compounds I, wherein $R^2$ is phenyl-$C_1$-$C_4$-alkyl, phenyl-$C_2$-$C_4$-alkenyl or phenyl-$C_2$-$C_4$-alkynyl, more preferably benzyl, phenylethenyl and phenylethynyl, in particular $R^2$ is benzyl, wherein the aforementioned groups may be substituted by $R^a$ and/or $R^b$ as defined above.

According to a further embodiment, $R^2$ is $C_3$-$C_8$-cycloalkyl-$C_1$-$C_4$-alkyl, in particular $C_3$-$C_6$-cycloalkyl-$C_1$-$C_2$-alkyl, or phenyl-$C_1$-$C_4$-alkyl, in particular phenyl-$C_1$-$C_2$-alkyl, that may be unsubstituted or substituted with $R^a$ and/or $R^b$ as defined herein.

A further embodiment relates to compounds I, wherein $R^2$ is unsubstituted.

According to a further embodiment, $R^a$, if present in $R^2$, is in each case independently selected from CN, nitro, $C_1$-$C_4$-alkoxy and $C_1$-$C_4$-halogenalkoxy and $R^b$, if present in $R^2$, is in each case independently selected from CN, nitro, $C_1$-$C_4$-alkyl, $C_1$-$C_4$-alkoxy, $C_1$-$C_4$-halogenalkyl and $C_1$-$C_4$-halogenalkoxy.

A further embodiment relates to compounds, wherein $X^1$ and $X^2$ are Cl and $R^2$ is unsubstituted benzyl, which compounds are of formula I.A:

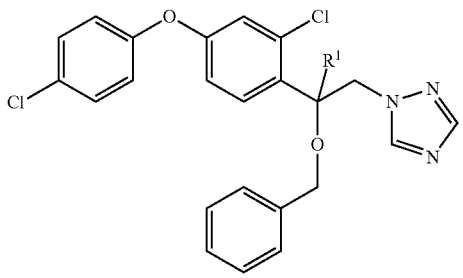

A further embodiment relates to compounds, wherein $X^1$ and $X^2$ are Cl and $R^2$ is cyclopropylmethyl, which compounds are of formula I.B:

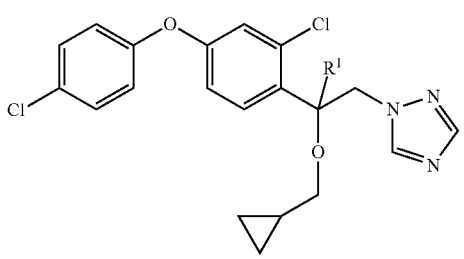

Particularly preferred embodiments of the invention relate to compounds I, wherein the combination of $X^1$, $X^2$ and $R^2$ (including $R^a$, $R^b$) is as defined in Table P below.

TABLE P

| line | $X^1$ | $X^2$ | $R^2$ |
| --- | --- | --- | --- |
| P-1 | Cl | Cl | $C_3H_5$ (cyclopropyl) |
| P-2 | Cl | F | $C_3H_5$ (cyclopropyl) |
| P-3 | F | Cl | $C_3H_5$ (cyclopropyl) |
| P-4 | F | F | $C_3H_5$ (cyclopropyl) |
| P-5 | Cl | Cl | $CH_2$—$C_3H_5$ |
| P-6 | Cl | F | $CH_2$—$C_3H_5$ |
| P-7 | F | Cl | $CH_2$—$C_3H_5$ |
| P-8 | F | F | $CH_2$—$C_3H_5$ |
| P-9 | Cl | Cl | $CH(CH_3)C_3H_5$ |
| P-10 | Cl | F | $CH(CH_3)C_3H_5$ |
| P-11 | F | Cl | $CH(CH_3)C_3H_5$ |
| P-12 | F | F | $CH(CH_3)C_3H_5$ |
| P-13 | Cl | Cl | 1-Cl—$C_3H_4$ |
| P-14 | Cl | F | 1-Cl—$C_3H_4$ |
| P-15 | F | Cl | 1-Cl—$C_3H_4$ |
| P-16 | F | F | 1-Cl—$C_3H_4$ |
| P-17 | Cl | Cl | $C_5H_9$ (cyclopentyl) |
| P-18 | Cl | F | $C_5H_9$ (cyclopentyl) |
| P-19 | F | Cl | $C_5H_9$ (cyclopentyl) |
| P-20 | F | F | $C_5H_9$ (cyclopentyl) |
| P-21 | Cl | Cl | $C_6H_{11}$ (cyclohexyl) |
| P-22 | Cl | F | $C_6H_{11}$ (cyclohexyl) |
| P-23 | F | Cl | $C_6H_{11}$ (cyclohexyl) |
| P-24 | F | F | $C_6H_{11}$ (cyclohexyl) |
| P-25 | Cl | Cl | $C_6H_5$ |
| P-26 | Cl | F | $C_6H_5$ |
| P-27 | F | Cl | $C_6H_5$ |
| P-28 | F | F | $C_6H_5$ |
| P-29 | Cl | Cl | 4-Cl—$C_6H_4$ |
| P-30 | Cl | F | 4-Cl—$C_6H_4$ |
| P-31 | F | Cl | 4-Cl—$C_6H_4$ |
| P-32 | F | F | 4-Cl—$C_6H_4$ |
| P-33 | Cl | Cl | —$CH_2$—$C_6H_5$ |
| P-34 | Cl | F | $CH_2$—$C_6H_5$ |
| P-35 | F | Cl | $CH_2$—$C_6H_5$ |
| P-36 | F | F | $CH_2$—$C_6H_5$ |
| P-37 | Cl | Cl | $CH_2$—(4-Cl—$C_6H_4$) |
| P-38 | Cl | F | $CH_2$—(4-Cl—$C_6H_4$) |
| P-39 | F | Cl | $CH_2$—(4-Cl—$C_6H_4$) |
| P-40 | F | F | $CH_2$—(4-Cl—$C_6H_4$) |
| P-41 | Cl | Cl | 2,4-$Cl_2$—$C_6H_3$ |
| P-42 | Cl | F | 2,4-$Cl_2$—$C_6H_3$ |
| P-43 | F | Cl | 2,4-$Cl_2$—$C_6H_3$ |
| P-44 | F | F | 2,4-$Cl_2$—$C_6H_3$ |
| P-45 | Cl | Cl | 2-F-4-Cl—$C_6H_3$ |
| P-46 | Cl | F | 2-F-4-Cl—$C_6H_3$ |
| P-47 | F | Cl | 2-F-4-Cl—$C_6H_3$ |
| P-48 | F | F | 2-F-4-Cl—$C_6H_3$ |
| P-49 | Cl | Cl | 2,4,6-$Cl_3$—$C_6H_2$ |
| P-50 | Cl | F | 2,4,6-$Cl_3$—$C_6H_2$ |
| P-51 | F | Cl | 2,4,6-$Cl_3$—$C_6H_2$ |
| P-52 | F | F | 2,4,6-$Cl_3$—$C_6H_2$ |
| P-53 | Cl | Cl | 2,4,6-$F_3$—$C_6H_2$ |
| P-54 | Cl | F | 2,4,6-$F_3$—$C_6H_2$ |
| P-55 | F | Cl | 2,4,6-$F_3$—$C_6H_2$ |
| P-56 | F | F | 2,4,6-$F_3$—$C_6H_2$ |
| P-57 | Cl | Cl | $CH_2$—(2,4,6-Cl—$C_6H_2$) |
| P-58 | Cl | F | $CH_2$—(2,4,6-Cl—$C_6H_2$) |
| P-59 | F | Cl | $CH_2$—(2,4,6-Cl—$C_6H_2$) |
| P-60 | F | F | $CH_2$—(2,4,6-Cl—$C_6H_2$) |
| P-61 | Cl | Cl | $CH_2$—(2,4,6-F—$C_6H_2$) |
| P-62 | Cl | F | $CH_2$—(2,4,6-F—$C_6H_2$) |
| P-63 | F | Cl | $CH_2$—(2,4,6-F—$C_6H_2$) |
| P-64 | F | F | $CH_2$—(2,4,6-F—$C_6H_2$) |
| P-65 | Cl | Cl | CH=CH—$C_6H_5$ |
| P-66 | Cl | F | CH=CH—$C_6H_5$ |
| P-67 | F | Cl | CH=CH—$C_6H_5$ |
| P-68 | F | F | CH=CH—$C_6H_5$ |
| P-69 | Cl | Cl | C≡C—$C_6H_5$ |
| P-70 | Cl | F | C≡C—$C_6H_5$ |
| P-71 | F | Cl | C≡C—$C_6H_5$ |
| P-72 | F | F | C≡C—$C_6H_5$ |
| P-73 | Cl | Cl | $CH_2$—C≡C—$C_6H_5$ |
| P-74 | Cl | F | $CH_2$—C≡C—$C_6H_5$ |
| P-75 | F | Cl | $CH_2$—C≡C—$C_6H_5$ |
| P-76 | F | F | $CH_2$—C≡C—$C_6H_5$ |
| P-77 | Cl | Cl | 1-CN—$C_3H_4$ |
| P-78 | Cl | F | 1-CN—$C_3H_4$ |
| P-79 | F | Cl | 1-CN—$C_3H_4$ |
| P-80 | F | F | 1-CN—$C_3H_4$ |
| P-81 | Cl | Cl | 1-F—$C_3H_4$ |
| P-82 | Cl | F | 1-F—$C_3H_4$ |
| P-83 | F | Cl | 1-F—$C_3H_4$ |
| P-84 | F | F | 1-F—$C_3H_4$ |
| P-85 | Cl | Cl | 1-$CH_3$—$C_3H_4$ |
| P-86 | Cl | F | 1-$CH_3$—$C_3H_4$ |
| P-87 | F | Cl | 1-$CH_3$—$C_3H_4$ |
| P-88 | F | F | 1-$CH_3$—$C_3H_4$ |
| P-89 | Cl | Cl | $CH_2$(4-$OCH_3$—$C_6H_4$) |
| P-90 | Cl | F | $CH_2$(4-$OCH_3$—$C_6H_4$) |
| P-91 | F | Cl | $CH_2$(4-$OCH_3$—$C_6H_4$) |
| P-92 | F | F | $CH_2$(4-$OCH_3$—$C_6H_4$) |
| P-93 | Cl | Cl | $CH_2$(4-$CH_3$—$C_6H_4$) |
| P-94 | Cl | F | $CH_2$(4-$CH_3$—$C_6H_4$) |
| P-95 | F | Cl | $CH_2$(4-$CH_3$—$C_6H_4$) |
| P-96 | F | F | $CH_2$(4-$CH_3$—$C_6H_4$) |
| P-97 | Cl | Cl | $C(CH_3)_2$—$C_3H_5$ |
| P-98 | Cl | F | $C(CH_3)_2$—$C_3H_5$ |
| P-99 | F | Cl | $C(CH_3)_2$—$C_3H_5$ |
| P-100 | F | F | $C(CH_3)_2$—$C_3H_5$ |
| P-101 | Cl | Cl | $CH_2$—$C_5H_9$ (cyclopentyl) |
| P-102 | Cl | F | $CH_2$—$C_5H_9$ (cyclopentyl) |
| P-103 | F | Cl | $CH_2$—$C_5H_9$ (cyclopentyl) |
| P-104 | F | F | $CH_2$—$C_5H_9$ (cyclopentyl) |
| P-105 | Cl | Cl | $CH_2$—$C_6H_{11}$ (cyclohexyl) |
| P-106 | Cl | F | $CH_2$—$C_6H_{11}$ (cyclohexyl) |
| P-107 | F | Cl | $CH_2$—$C_6H_{11}$ (cyclohexyl) |
| P-108 | F | F | $CH_2$—$C_6H_{11}$ (cyclohexyl) |

A skilled person will readily understand that the preferences given in connection with compounds I apply for e.g. formula VIII, $X^1$ and XII as defined above.

With respect to their use, particular preference is given to compounds I to 3240, 1a to 3240a and 1b to 3240b of formula I compiled in Tables 1 to 84, tables 84a to 84x, tables 85 to 168, tables 168a to 168x, 169 to 252 and 252a to 252x below. The groups mentioned in the Tables for a substituent are furthermore, independently of the combination wherein they are mentioned, a particularly preferred embodiment of the substituent in question.

Table 1: Compounds I to 30 of formula I, wherein $X^1$, $X^2$ and $R^2$ are defined as in line P-1 of table P and the meaning of $R^1$ for each individual compound corresponds in each case to one line of table A.

Table 2: Compounds 31 to 60 of formula I, wherein $X^1$, $X^2$ and $R^2$ are defined as in line P-2 of table P and the meaning of $R^1$ for each individual compound corresponds in each case to one line of table A.

Table 3: Compounds 61 to 90 of formula I, wherein $X^1$, $X^2$ and $R^2$ are defined as in line P-3 of table P and the meaning of $R^1$ for each individual compound corresponds in each case to one line of table A.

Table 4: Compounds 91 to 120 of formula I, wherein $X^1$, $X^2$ and $R^2$ are defined as in line P-4 of table P and the meaning of $R^1$ for each individual compound corresponds in each case to one line of table A.

Table 5: Compounds 121 to 150 of formula I, wherein $X^1$, $X^2$ and $R^2$ are defined as in line P-5 of table P and the meaning of $R^1$ for each individual compound corresponds in each case to one line of table A.

Table 6: Compounds 151 to 180 of formula I, wherein $X^1$, $X^2$ and $R^2$ are defined as in line P-6 of table P and the meaning of $R^1$ for each individual compound corresponds in each case to one line of table A.

Table 7: Compounds 181 to 210 of formula I, wherein $X^1$, $X^2$ and $R^2$ are defined as in line P-7 of table P and the meaning of $R^1$ for each individual compound corresponds in each case to one line of table A.

Table 8: Compounds 211 to 240 of formula I, wherein $X^1$, $X^2$ and $R^2$ are defined as in line P-8 of table P and the meaning of $R^1$ for each individual compound corresponds in each case to one line of table A.

Table 9: Compounds 241 to 270 of formula I, wherein $X^1$, $X^2$ and $R^2$ are defined as in line P-9 of table P and the meaning of $R^1$ for each individual compound corresponds in each case to one line of table A.

Table 10: Compounds 271 to 300 of formula I, wherein $X^1$, $X^2$ and $R^2$ are defined as in line P-10 of table P and the meaning of $R^1$ for each individual compound corresponds in each case to one line of table A.

Table 11: Compounds 301 to 330 of formula I, wherein $X^1$, $X^2$ and $R^2$ are defined as in line P-11 of table P and the meaning of $R^1$ for each individual compound corresponds in each case to one line of table A.

Table 12: Compounds 331 to 360 of formula I, wherein $X^1$, $X^2$ and $R^2$ are defined as in line P-12 of table P and the meaning of $R^1$ for each individual compound corresponds in each case to one line of table A.

Table 13: Compounds 361 to 390 of formula I, wherein $X^1$, $X^2$ and $R^2$ are defined as in line P-13 of table P and the meaning of $R^1$ for each individual compound corresponds in each case to one line of table A.

Table 14: Compounds 391 to 420 of formula I, wherein $X^1$, $X^2$ and $R^2$ are defined as in line P-14 of table P and the meaning of $R^1$ for each individual compound corresponds in each case to one line of table A.

Table 15: Compounds 421 to 450 of formula I, wherein $X^1$, $X^2$ and $R^2$ are defined as in line P-15 of table P and the meaning of $R^1$ for each individual compound corresponds in each case to one line of table A.

Table 16: Compounds 451 to 480 of formula I, wherein $X^1$, $X^2$ and $R^2$ are defined as in line P-16 of table P and the meaning of $R^1$ for each individual compound corresponds in each case to one line of table A.

Table 17: Compounds 481 to 510 of formula I, wherein $X^1$, $X^2$ and $R^2$ are defined as in line P-17 of table P and the meaning of $R^1$ for each individual compound corresponds in each case to one line of table A.

Table 18: Compounds 511 to 540 of formula I, wherein $X^1$, $X^2$ and $R^2$ are defined as in line P-18 of table P and the meaning of $R^1$ for each individual compound corresponds in each case to one line of table A.

Table 19: Compounds 541 to 570 of formula I, wherein $X^1$, $X^2$ and $R^2$ are defined as in line P-19 of table P and the meaning of $R^1$ for each individual compound corresponds in each case to one line of table A.

Table 20: Compounds 571 to 600 of formula I, wherein $X^1$, $X^2$ and $R^2$ are defined as in line P-20 of table P and the meaning of $R^1$ for each individual compound corresponds in each case to one line of table A.

Table 21: Compounds 601 to 630 of formula I, wherein $X^1$, $X^2$ and $R^2$ are defined as in line P-21 of table P and the meaning of $R^1$ for each individual compound corresponds in each case to one line of table A.

Table 22: Compounds 631 to 660 of formula I, wherein $X^1$, $X^2$ and $R^2$ are defined as in line P-22 of table P and the meaning of $R^1$ for each individual compound corresponds in each case to one line of table A.

Table 23: Compounds 661 to 690 of formula I, wherein $X^1$, $X^2$ and $R^2$ are defined as in line P-23 of table P and the meaning of $R^1$ for each individual compound corresponds in each case to one line of table A.

Table 24: Compounds 691 to 720 of formula I, wherein $X^1$, $X^2$ and $R^2$ are defined as in line P-24 of table P and the meaning of $R^1$ for each individual compound corresponds in each case to one line of table A.

Table 25: Compounds 721 to 750 of formula I, wherein $X^1$, $X^2$ and $R^2$ are defined as in line P-25 of table P and the meaning of $R^1$ for each individual compound corresponds in each case to one line of table A.

Table 26: Compounds 751 to 780 of formula I, wherein $X^1$, $X^2$ and $R^2$ are defined as in line P-26 of table P and the meaning of $R^1$ for each individual compound corresponds in each case to one line of table A.

Table 27: Compounds 781 to 810 of formula I, wherein $X^1$, $X^2$ and $R^2$ are defined as in line P-27 of table P and the meaning of $R^1$ for each individual compound corresponds in each case to one line of table A.

Table 28: Compounds 811 to 840 of formula I, wherein $X^1$, $X^2$ and $R^2$ are defined as in line P-28 of table P and the meaning of $R^1$ for each individual compound corresponds in each case to one line of table A.

Table 29: Compounds 841 to 870 of formula I, wherein $X^1$, $X^2$ and $R^2$ are defined as in line P-29 of table P and the meaning of $R^1$ for each individual compound corresponds in each case to one line of table A.

Table 30: Compounds 871 to 900 of formula I, wherein $X^1$, $X^2$ and $R^2$ are defined as in line P-30 of table P and the meaning of $R^1$ for each individual compound corresponds in each case to one line of table A.

Table 31: Compounds 901 to 930 of formula I, wherein $X^1$, $X^2$ and $R^2$ are defined as in line P-31 of table P and the meaning of $R^1$ for each individual compound corresponds in each case to one line of table A.

Table 32: Compounds 931 to 960 of formula I, wherein $X^1$, $X^2$ and $R^2$ are defined as in line P-32 of table P and the meaning of $R^1$ for each individual compound corresponds in each case to one line of table A.
Table 33: Compounds 961 to 990 of formula I, wherein $X^1$, $X^2$ and $R^2$ are defined as in line P-33 of table P and the meaning of $R^1$ for each individual compound corresponds in each case to one line of table A.
Table 34: Compounds 991 to 1020 of formula I, wherein $X^1$, $X^2$ and $R^2$ are defined as in line P-34 of table P and the meaning of $R^1$ for each individual compound corresponds in each case to one line of table A.
Table 35: Compounds 1021 to 1050 of formula I, wherein $X^1$, $X^2$ and $R^2$ are defined as in line P-35 of table P and the meaning of $R^1$ for each individual compound corresponds in each case to one line of table A.
Table 36: Compounds 1051 to 1080 of formula I, wherein $X^1$, $X^2$ and $R^2$ are defined as in line P-36 of table P and the meaning of $R^1$ for each individual compound corresponds in each case to one line of table A.
Table 37: Compounds 1081 to 1110 of formula I, wherein $X^1$, $X^2$ and $R^2$ are defined as in line P-37 of table P and the meaning of $R^1$ for each individual compound corresponds in each case to one line of table A.
Table 38: Compounds 1111 to 1140 of formula I, wherein $X^1$, $X^2$ and $R^2$ are defined as in line P-38 of table P and the meaning of $R^1$ for each individual compound corresponds in each case to one line of table A.
Table 39: Compounds 1141 to 1170 of formula I, wherein $X^1$, $X^2$ and $R^2$ are defined as in line P-39 of table P and the meaning of $R^1$ for each individual compound corresponds in each case to one line of table A.
Table 40: Compounds 1171 to 1200 of formula I, wherein $X^1$, $X^2$ and $R^2$ are defined as in line P-40 of table P and the meaning of $R^1$ for each individual compound corresponds in each case to one line of table A.
Table 41: Compounds 1201 to 1230 of formula I, wherein $X^1$, $X^2$ and $R^2$ are defined as in line P-41 of table P and the meaning of $R^1$ for each individual compound corresponds in each case to one line of table A.
Table 42: Compounds 1231 to 1260 of formula I, wherein $X^1$, $X^2$ and $R^2$ are defined as in line P-42 of table P and the meaning of $R^1$ for each individual compound corresponds in each case to one line of table A.
Table 43: Compounds 1261 to 1290 of formula I, wherein $X^1$, $X^2$ and $R^2$ are defined as in line P-43 of table P and the meaning of $R^1$ for each individual compound corresponds in each case to one line of table A.
Table 44: Compounds 1291 to 1320 of formula I, wherein $X^1$, $X^2$ and $R^2$ are defined as in line P-44 of table P and the meaning of $R^1$ for each individual compound corresponds in each case to one line of table A.
Table 45: Compounds 1321 to 1350 of formula I, wherein $X^1$, $X^2$ and $R^2$ are defined as in line P-45 of table P and the meaning of $R^1$ for each individual compound corresponds in each case to one line of table A.
Table 46: Compounds 1351 to 1380 of formula I, wherein $X^1$, $X^2$ and $R^2$ are defined as in line P-46 of table P and the meaning of $R^1$ for each individual compound corresponds in each case to one line of table A.
Table 47: Compounds 1381 to 1410 of formula I, wherein $X^1$, $X^2$ and $R^2$ are defined as in line P-47 of table P and the meaning of $R^1$ for each individual compound corresponds in each case to one line of table A.
Table 48: Compounds 1411 to 1440 of formula I, wherein $X^1$, $X^2$ and $R^2$ are defined as in line P-48 of table P and the meaning of $R^1$ for each individual compound corresponds in each case to one line of table A.
Table 49: Compounds 1441 to 1470 of formula I, wherein $X^1$, $X^2$ and $R^2$ are defined as in line P-49 of table P and the meaning of $R^1$ for each individual compound corresponds in each case to one line of table A.
Table 50: Compounds 1471 to 1500 of formula I, wherein $X^1$, $X^2$ and $R^2$ are defined as in line P-50 of table P and the meaning of $R^1$ for each individual compound corresponds in each case to one line of table A.
Table 51: Compounds 1501 to 1530 of formula I, wherein $X^1$, $X^2$ and $R^2$ are defined as in line P-51 of table P and the meaning of $R^1$ for each individual compound corresponds in each case to one line of table A.
Table 52: Compounds 1531 to 1560 of formula I, wherein $X^1$, $X^2$ and $R^2$ are defined as in line P-52 of table P and the meaning of $R^1$ for each individual compound corresponds in each case to one line of table A.
Table 53: Compounds 1561 to 1590 of formula I, wherein $X^1$, $X^2$ and $R^2$ are defined as in line P-53 of table P and the meaning of $R^1$ for each individual compound corresponds in each case to one line of table A.
Table 54: Compounds 1591 to 1620 of formula I, wherein $X^1$, $X^2$ and $R^2$ are defined as in line P-54 of table P and the meaning of $R^1$ for each individual compound corresponds in each case to one line of table A.
Table 55: Compounds 1621 to 1650 of formula I, wherein $X^1$, $X^2$ and $R^2$ are defined as in line P-55 of table P and the meaning of $R^1$ for each individual compound corresponds in each case to one line of table A.
Table 56: Compounds 1651 to 1680 of formula I, wherein $X^1$, $X^2$ and $R^2$ are defined as in line P-56 of table P and the meaning of $R^1$ for each individual compound corresponds in each case to one line of table A.
Table 57: Compounds 1681 to 1710 of formula I, wherein $X^1$, $X^2$ and $R^2$ are defined as in line P-57 of table P and the meaning of $R^1$ for each individual compound corresponds in each case to one line of table A.
Table 58: Compounds 1711 to 1740 of formula I, wherein $X^1$, $X^2$ and $R^2$ are defined as in line P-58 of table P and the meaning of $R^1$ for each individual compound corresponds in each case to one line of table A.
Table 59: Compounds 1741 to 1770 of formula I, wherein $X^1$, $X^2$ and $R^2$ are defined as in line P-59 of table P and the meaning of $R^1$ for each individual compound corresponds in each case to one line of table A.
Table 60: Compounds 1771 to 1800 of formula I, wherein $X^1$, $X^2$ and $R^2$ are defined as in line P-60 of table P and the meaning of $R^1$ for each individual compound corresponds in each case to one line of table A.
Table 61: Compounds 1801 to 1830 of formula I, wherein $X^1$, $X^2$ and $R^2$ are defined as in line P-61 of table P and the meaning of $R^1$ for each individual compound corresponds in each case to one line of table A.
Table 62: Compounds 1831 to 1860 of formula I, wherein $X^1$, $X^2$ and $R^2$ are defined as in line P-62 of table P and the meaning of $R^1$ for each individual compound corresponds in each case to one line of table A.
Table 63: Compounds 1861 to 1890 of formula I, wherein $X^1$, $X^2$ and $R^2$ are defined as in line P-63 of table P and the meaning of $R^1$ for each individual compound corresponds in each case to one line of table A.
Table 64: Compounds 1891 to 1920 of formula I, wherein $X^1$, $X^2$ and $R^2$ are defined as in line P-64 of table P and the meaning of $R^1$ for each individual compound corresponds in each case to one line of table A.

Table 65: Compounds 1921 to 1950 of formula I, wherein $X^1$, $X^2$ and $R^2$ are defined as in line P-65 of table P and the meaning of $R^1$ for each individual compound corresponds in each case to one line of table A.
Table 66: Compounds 1951 to 1980 of formula I, wherein $X^1$, $X^2$ and $R^2$ are defined as in line P-66 of table P and the meaning of $R^1$ for each individual compound corresponds in each case to one line of table A.
Table 67: Compounds 1981 to 2010 of formula I, wherein $X^1$, $X^2$ and $R^2$ are defined as in line P-67 of table P and the meaning of $R^1$ for each individual compound corresponds in each case to one line of table A.
Table 68: Compounds 2011 to 2040 of formula I, wherein $X^1$, $X^2$ and $R^2$ are defined as in line P-68 of table P and the meaning of $R^1$ for each individual compound corresponds in each case to one line of table A.
Table 69: Compounds 2041 to 2070 of formula I, wherein $X^1$, $X^2$ and $R^2$ are defined as in line P-69 of table P and the meaning of $R^1$ for each individual compound corresponds in each case to one line of table A.
Table 70: Compounds 2071 to 2100 of formula I, wherein $X^1$, $X^2$ and $R^2$ are defined as in line P-70 of table P and the meaning of $R^1$ for each individual compound corresponds in each case to one line of table A.
Table 71: Compounds 2101 to 2130 of formula I, wherein $X^1$, $X^2$ and $R^2$ are defined as in line P-71 of table P and the meaning of $R^1$ for each individual compound corresponds in each case to one line of table A.
Table 72: Compounds 2131 to 2160 of formula I, wherein $X^1$, $X^2$ and $R^2$ are defined as in line P-72 of table P and the meaning of $R^1$ for each individual compound corresponds in each case to one line of table A.
Table 73: Compounds 2161 to 2190 of formula I, wherein $X^1$, $X^2$ and $R^2$ are defined as in line P-73 of table P and the meaning of $R^1$ for each individual compound corresponds in each case to one line of table A.
Table 74: Compounds 2191 to 2220 of formula I, wherein $X^1$, $X^2$ and $R^2$ are defined as in line P-74 of table P and the meaning of $R^1$ for each individual compound corresponds in each case to one line of table A.
Table 75: Compounds 2221 to 2250 of formula I, wherein $X^1$, $X^2$ and $R^2$ are defined as in line P-75 of table P and the meaning of $R^1$ for each individual compound corresponds in each case to one line of table A.
Table 76: Compounds 2251 to 2280 of formula I, wherein $X^1$, $X^2$ and $R^2$ are defined as in line P-76 of table P and the meaning of $R^1$ for each individual compound corresponds in each case to one line of table A.
Table 77: Compounds 2281 to 2310 of formula I, wherein $X^1$, $X^2$ and $R^2$ are defined as in line P-77 of table P and the meaning of $R^1$ for each individual compound corresponds in each case to one line of table A.
Table 78: Compounds 2311 to 2340 of formula I, wherein $X^1$, $X^2$ and $R^2$ are defined as in line P-78 of table P and the meaning of $R^1$ for each individual compound corresponds in each case to one line of table A.
Table 79: Compounds 2341 to 2370 of formula I, wherein $X^1$, $X^2$ and $R^2$ are defined as in line P-79 of table P and the meaning of $R^1$ for each individual compound corresponds in each case to one line of table A.
Table 80: Compounds 2371 to 2400 of formula I, wherein $X^1$, $X^2$ and $R^2$ are defined as in line P-80 of table P and the meaning of $R^1$ for each individual compound corresponds in each case to one line of table A.
Table 81: Compounds 2401 to 2430 of formula I, wherein $X^1$, $X^2$ and $R^2$ are defined as in line P-81 of table P and the meaning of $R^1$ for each individual compound corresponds in each case to one line of table A.
Table 82: Compounds 2431 to 2460 of formula I, wherein $X^1$, $X^2$ and $R^2$ are defined as in line P-82 of table P and the meaning of $R^1$ for each individual compound corresponds in each case to one line of table A.
Table 83: Compounds 2461 to 2490 of formula I, wherein $X^1$, $X^2$ and $R^2$ are defined as in line P-83 of table P and the meaning of $R^1$ for each individual compound corresponds in each case to one line of table A.
Table 84: Compounds 2491 to 2520 of formula I, wherein $X^1$, $X^2$ and $R^2$ are defined as in line P-84 of table P and the meaning of $R^1$ for each individual compound corresponds in each case to one line of table A.
Table 84a: Compounds 2521 to 2550 of formula I, wherein $X^1$, $X^2$ and $R^2$ are defined as in line P-85 of table P and the meaning of $R^1$ for each individual compound corresponds in each case to one line of table A.
Table 84b: Compounds 2551 to 2580 of formula I, wherein $X^1$, $X^2$ and $R^2$ are defined as in line P-86 of table P and the meaning of $R^1$ for each individual compound corresponds in each case to one line of table A.
Table 84c: Compounds 2581 to 2610 of formula I, wherein $X^1$, $X^2$ and $R^2$ are defined as in line P-87 of table P and the meaning of $R^1$ for each individual compound corresponds in each case to one line of table A.
Table 84d: Compounds 2611 to 2640 of formula I, wherein $X^1$, $X^2$ and $R^2$ are defined as in line P-88 of table P and the meaning of $R^1$ for each individual compound corresponds in each case to one line of table A.
Table 84e: Compounds 2641 to 2670 of formula I, wherein $X^1$, $X^2$ and $R^2$ are defined as in line P-89 of table P and the meaning of $R^1$ for each individual compound corresponds in each case to one line of table A.
Table 84f: Compounds 2671 to 2700 of formula I, wherein $X^1$, $X^2$ and $R^2$ are defined as in line P-90 of table P and the meaning of $R^1$ for each individual compound corresponds in each case to one line of table A.
Table 84g: Compounds 2701 to 2730 of formula I, wherein $X^1$, $X^2$ and $R^2$ are defined as in line P-91 of table P and the meaning of $R^1$ for each individual compound corresponds in each case to one line of table A.
Table 84h: Compounds 2731 to 2760 of formula I, wherein $X^1$, $X^2$ and $R^2$ are defined as in line P-92 of table P and the meaning of $R^1$ for each individual compound corresponds in each case to one line of table A.
Table 84i: Compounds 2761 to 2790 of formula I, wherein $X^1$, $X^2$ and $R^2$ are defined as in line P-93 of table P and the meaning of $R^1$ for each individual compound corresponds in each case to one line of table A.
Table 84j: Compounds 2791 to 2820 of formula I, wherein $X^1$, $X^2$ and $R^2$ are defined as in line P-94 of table P and the meaning of $R^1$ for each individual compound corresponds in each case to one line of table A.
Table 84k: Compounds 2821 to 2850 of formula I, wherein $X^1$, $X^2$ and $R^2$ are defined as in line P-95 of table P and the meaning of $R^1$ for each individual compound corresponds in each case to one line of table A.
Table 84l: Compounds 2851 to 2880 of formula I, wherein $X^1$, $X^2$ and $R^2$ are defined as in line P-96 of table P and the meaning of $R^1$ for each individual compound corresponds in each case to one line of table A.
Table 84m: Compounds 2881 to 2910 of formula I, wherein $X^1$, $X^2$ and $R^2$ are defined as in line P-97 of table P and the meaning of $R^1$ for each individual compound corresponds in each case to one line of table A.

Table 84n: Compounds 2911 to 2940 of formula I, wherein $X^1$, $X^2$ and $R^2$ are defined as in line P-98 of table P and the meaning of $R^1$ for each individual compound corresponds in each case to one line of table A.

Table 84o: Compounds 2941 to 2970 of formula I, wherein $X^1$, $X^2$ and $R^2$ are defined as in line P-99 of table P and the meaning of $R^1$ for each individual compound corresponds in each case to one line of table A.

Table 84p: Compounds 2971 to 3000 of formula I, wherein $X^1$, $X^2$ and $R^2$ are defined as in line P-100 of table P and the meaning of $R^1$ for each individual compound corresponds in each case to one line of table A.

Table 84q: Compounds 3001 to 3030 of formula I, wherein $X^1$, $X^2$ and $R^2$ are defined as in line P-101 of table P and the meaning of $R^1$ for each individual compound corresponds in each case to one line of table A.

Table 84r: Compounds 3031 to 3060 of formula I, wherein $X^1$, $X^2$ and $R^2$ are defined as in line P-102 of table P and the meaning of $R^1$ for each individual compound corresponds in each case to one line of table A.

Table 84s: Compounds 3061 to 3090 of formula I, wherein $X^1$, $X^2$ and $R^2$ are defined as in line P-103 of table P and the meaning of $R^1$ for each individual compound corresponds in each case to one line of table A.

Table 84t: Compounds 3091 to 3120 of formula I, wherein $X^1$, $X^2$ and $R^2$ are defined as in line P-104 of table P and the meaning of $R^1$ for each individual compound corresponds in each case to one line of table A.

Table 84u: Compounds 3121 to 3150 of formula I, wherein $X^1$, $X^2$ and $R^2$ are defined as in line P-105 of table P and the meaning of $R^1$ for each individual compound corresponds in each case to one line of table A.

Table 84v: Compounds 3151 to 3180 of formula I, wherein $X^1$, $X^2$ and $R^2$ are defined as in line P-106 of table P and the meaning of $R^1$ for each individual compound corresponds in each case to one line of table A.

Table 84w: Compounds 3181 to 3210 of formula I, wherein $X^1$, $X^2$ and $R^2$ are defined as in line P-107 of table P and the meaning of $R^1$ for each individual compound corresponds in each case to one line of table A.

Table 84x: Compounds 3211 to 3240 of formula I, wherein $X^1$, $X^2$ and $R^2$ are defined as in line P-108 of table P and the meaning of $R^1$ for each individual compound corresponds in each case to one line of table A.

Table 85: Compounds 1a to 30a of formula I, wherein $X^1$, $X^2$ and $R^2$ are defined as in line P-1 of table P and the meaning of $R^1$ for each individual compound corresponds in each case to one line of table A1.

Table 86: Compounds 31a to 60a of formula I, wherein $X^1$, $X^2$ and $R^2$ are defined as in line P-2 of table P and the meaning of $R^1$ for each individual compound corresponds in each case to one line of table A1.

Table 87: Compounds 61a to 90a of formula I, wherein $X^1$, $X^2$ and $R^2$ are defined as in line P-3 of table P and the meaning of $R^1$ for each individual compound corresponds in each case to one line of table A1.

Table 88: Compounds 91a to 120a of formula I, wherein $X^1$, $X^2$ and $R^2$ are defined as in line P-4 of table P and the meaning of $R^1$ for each individual compound corresponds in each case to one line of table A1.

Table 89: Compounds 121a to 150a of formula I, wherein $X^1$, $X^2$ and $R^2$ are defined as in line P-5 of table P and the meaning of $R^1$ for each individual compound corresponds in each case to one line of table A1.

Table 90: Compounds 151a to 180a of formula I, wherein $X^1$, $X^2$ and $R^2$ are defined as in line P-6 of table P and the meaning of $R^1$ for each individual compound corresponds in each case to one line of table A1.

Table 91: Compounds 181a to 210a of formula I, wherein $X^1$, $X^2$ and $R^2$ are defined as in line P-7 of table P and the meaning of $R^1$ for each individual compound corresponds in each case to one line of table A1.

Table 92: Compounds 211a to 240a of formula I, wherein $X^1$, $X^2$ and $R^2$ are defined as in line P-8 of table P and the meaning of $R^1$ for each individual compound corresponds in each case to one line of table A1.

Table 93: Compounds 241a to 270a of formula I, wherein $X^1$, $X^2$ and $R^2$ are defined as in line P-9 of table P and the meaning of $R^1$ for each individual compound corresponds in each case to one line of table A1.

Table 94: Compounds 271a to 300a of formula I, wherein $X^1$, $X^2$ and $R^2$ are defined as in line P-10 of table P and the meaning of $R^1$ for each individual compound corresponds in each case to one line of table A1.

Table 95: Compounds 301a to 330a of formula I, wherein $X^1$, $X^2$ and $R^2$ are defined as in line P-11 of table P and the meaning of $R^1$ for each individual compound corresponds in each case to one line of table A1.

Table 96: Compounds 331a to 360a of formula I, wherein $X^1$, $X^2$ and $R^2$ are defined as in line P-12 of table P and the meaning of $R^1$ for each individual compound corresponds in each case to one line of table A1.

Table 97: Compounds 361a to 390a of formula I, wherein $X^1$, $X^2$ and $R^2$ are defined as in line P-13 of table P and the meaning of $R^1$ for each individual compound corresponds in each case to one line of table A1.

Table 98: Compounds 391a to 420a of formula I, wherein $X^1$, $X^2$ and $R^2$ are defined as in line P-14 of table P and the meaning of $R^1$ for each individual compound corresponds in each case to one line of table A1.

Table 99: Compounds 421a to 450a of formula I, wherein $X^1$, $X^2$ and $R^2$ are defined as in line P-15 of table P and the meaning of $R^1$ for each individual compound corresponds in each case to one line of table A1.

Table 100: Compounds 451a to 480a of formula I, wherein $X^1$, $X^2$ and $R^2$ are defined as in line P-16 of table P and the meaning of $R^1$ for each individual compound corresponds in each case to one line of table A1.

Table 101: Compounds 481a to 510a of formula I, wherein $X^1$, $X^2$ and $R^2$ are defined as in line P-17 of table P and the meaning of $R^1$ for each individual compound corresponds in each case to one line of table A1.

Table 102: Compounds 511a to 540a of formula I, wherein $X^1$, $X^2$ and $R^2$ are defined as in line P-18 of table P and the meaning of $R^1$ for each individual compound corresponds in each case to one line of table A1.

Table 103: Compounds 541a to 570a of formula I, wherein $X^1$, $X^2$ and $R^2$ are defined as in line P-19 of table P and the meaning of $R^1$ for each individual compound corresponds in each case to one line of table A1.

Table 104: Compounds 571a to 600a of formula I, wherein $X^1$, $X^2$ and $R^2$ are defined as in line P-20 of table P and the meaning of $R^1$ for each individual compound corresponds in each case to one line of table A1.

Table 105: Compounds 601a to 630a of formula I, wherein $X^1$, $X^2$ and $R^2$ are defined as in line P-21 of table P and the meaning of $R^1$ for each individual compound corresponds in each case to one line of table A1.

Table 106: Compounds 631a to 660a of formula I, wherein $X^1$, $X^2$ and $R^2$ are defined as in line P-22 of table P and the meaning of $R^1$ for each individual compound corresponds in each case to one line of table A1.

Table 107: Compounds 661a to 690a of formula I, wherein $X^1$, $X^2$ and $R^2$ are defined as in line P-23 of table P and the meaning of $R^1$ for each individual compound corresponds in each case to one line of table A1.

Table 108: Compounds 691a to 720a of formula I, wherein $X^1$, $X^2$ and $R^2$ are defined as in line P-24 of table P and the meaning of $R^1$ for each individual compound corresponds in each case to one line of table A1.

Table 109: Compounds 721a to 750a of formula I, wherein $X^1$, $X^2$ and $R^2$ are defined as in line P-25 of table P and the meaning of $R^1$ for each individual compound corresponds in each case to one line of table A1.

Table 110: Compounds 751a to 780a of formula I, wherein $X^1$, $X^2$ and $R^2$ are defined as in line P-26 of table P and the meaning of $R^1$ for each individual compound corresponds in each case to one line of table A1.

Table 111: Compounds 781a to 810a of formula I, wherein $X^1$, $X^2$ and $R^2$ are defined as in line P-27 of table P and the meaning of $R^1$ for each individual compound corresponds in each case to one line of table A1.

Table 112: Compounds 811a to 840a of formula I, wherein $X^1$, $X^2$ and $R^2$ are defined as in line P-28 of table P and the meaning of $R^1$ for each individual compound corresponds in each case to one line of table A1.

Table 113: Compounds 841a to 870a of formula I, wherein $X^1$, $X^2$ and $R^2$ are defined as in line P-29 of table P and the meaning of $R^1$ for each individual compound corresponds in each case to one line of table A1.

Table 114: Compounds 871a to 900a of formula I, wherein $X^1$, $X^2$ and $R^2$ are defined as in line P-30 of table P and the meaning of $R^1$ for each individual compound corresponds in each case to one line of table A1.

Table 115: Compounds 901a to 930a of formula I, wherein $X^1$, $X^2$ and $R^2$ are defined as in line P-31 of table P and the meaning of $R^1$ for each individual compound corresponds in each case to one line of table A1.

Table 116: Compounds 931a to 960a of formula I, wherein $X^1$, $X^2$ and $R^2$ are defined as in line P-32 of table P and the meaning of $R^1$ for each individual compound corresponds in each case to one line of table A1.

Table 117: Compounds 961a to 990a of formula I, wherein $X^1$, $X^2$ and $R^2$ are defined as in line P-33 of table P and the meaning of $R^1$ for each individual compound corresponds in each case to one line of table A1.

Table 118: Compounds 991a to 1020a of formula I, wherein $X^1$, $X^2$ and $R^2$ are defined as in line P-34 of table P and the meaning of $R^1$ for each individual compound corresponds in each case to one line of table A1.

Table 119: Compounds 1021a to 1050a of formula I, wherein $X^1$, $X^2$ and $R^2$ are defined as in line P-35 of table P and the meaning of $R^1$ for each individual compound corresponds in each case to one line of table A1.

Table 120: Compounds 1051a to 1080a of formula I, wherein $X^1$, $X^2$ and $R^2$ are defined as in line P-36 of table P and the meaning of $R^1$ for each individual compound corresponds in each case to one line of table A1.

Table 121: Compounds 1081a to 1110a of formula I, wherein $X^1$, $X^2$ and $R^2$ are defined as in line P-37 of table P and the meaning of $R^1$ for each individual compound corresponds in each case to one line of table A1.

Table 122: Compounds 1111a to 1140a of formula I, wherein $X^1$, $X^2$ and $R^2$ are defined as in line P-38 of table P and the meaning of $R^1$ for each individual compound corresponds in each case to one line of table A1.

Table 123: Compounds 1141a to 1170a of formula I, wherein $X^1$, $X^2$ and $R^2$ are defined as in line P-39 of table P and the meaning of $R^1$ for each individual compound corresponds in each case to one line of table A1.

Table 124: Compounds 1171a to 1200a of formula I, wherein $X^1$, $X^2$ and $R^2$ are defined as in line P-40 of table P and the meaning of $R^1$ for each individual compound corresponds in each case to one line of table A1.

Table 125: Compounds 1201a to 1230a of formula I, wherein $X^1$, $X^2$ and $R^2$ are defined as in line P-41 of table P and the meaning of $R^1$ for each individual compound corresponds in each case to one line of table A1.

Table 126: Compounds 1231a to 1260a of formula I, wherein $X^1$, $X^2$ and $R^2$ are defined as in line P-42 of table P and the meaning of $R^1$ for each individual compound corresponds in each case to one line of table A1.

Table 127: Compounds 1261a to 1290a of formula I, wherein $X^1$, $X^2$ and $R^2$ are defined as in line P-43 of table P and the meaning of $R^1$ for each individual compound corresponds in each case to one line of table A1.

Table 128: Compounds 1291a to 1320a of formula I, wherein $X^1$, $X^2$ and $R^2$ are defined as in line P-44 of table P and the meaning of $R^1$ for each individual compound corresponds in each case to one line of table A1.

Table 129: Compounds 1321a to 1350a of formula I, wherein $X^1$, $X^2$ and $R^2$ are defined as in line P-45 of table P and the meaning of $R^1$ for each individual compound corresponds in each case to one line of table A1.

Table 130: Compounds 1351a to 1380a of formula I, wherein $X^1$, $X^2$ and $R^2$ are defined as in line P-46 of table P and the meaning of $R^1$ for each individual compound corresponds in each case to one line of table A1.

Table 131: Compounds 1381a to 1410a of formula I, wherein $X^1$, $X^2$ and $R^2$ are defined as in line P-47 of table P and the meaning of $R^1$ for each individual compound corresponds in each case to one line of table A1.

Table 132: Compounds 1411a to 1440a of formula I, wherein $X^1$, $X^2$ and $R^2$ are defined as in line P-48 of table P and the meaning of $R^1$ for each individual compound corresponds in each case to one line of table A1.

Table 133: Compounds 1441a to 1470a of formula I, wherein $X^1$, $X^2$ and $R^2$ are defined as in line P-49 of table P and the meaning of $R^1$ for each individual compound corresponds in each case to one line of table A1.

Table 134: Compounds 1471a to 1500a of formula I, wherein $X^1$, $X^2$ and $R^2$ are defined as in line P-50 of table P and the meaning of $R^1$ for each individual compound corresponds in each case to one line of table A1.

Table 135: Compounds 1501a to 1530a of formula I, wherein $X^1$, $X^2$ and $R^2$ are defined as in line P-51 of table P and the meaning of $R^1$ for each individual compound corresponds in each case to one line of table A1.

Table 136: Compounds 1531a to 1560a of formula I, wherein $X^1$, $X^2$ and $R^2$ are defined as in line P-52 of table P and the meaning of $R^1$ for each individual compound corresponds in each case to one line of table A1.

Table 137: Compounds 1561a to 1590a of formula I, wherein $X^1$, $X^2$ and $R^2$ are defined as in line P-53 of table P and the meaning of $R^1$ for each individual compound corresponds in each case to one line of table A1.

Table 138: Compounds 1591a to 1620a of formula I, wherein $X^1$, $X^2$ and $R^2$ are defined as in line P-54 of table P and the meaning of $R^1$ for each individual compound corresponds in each case to one line of table A1.

Table 139: Compounds 1621a to 1650a of formula I, wherein $X^1$, $X^2$ and $R^2$ are defined as in line P-55 of table P and the meaning of $R^1$ for each individual compound corresponds in each case to one line of table A1.

Table 140: Compounds 1651a to 1680a of formula I, wherein $X^1$, $X^2$ and $R^2$ are defined as in line P-56 of table P and the meaning of $R^1$ for each individual compound corresponds in each case to one line of table A1.

Table 141: Compounds 1681a to 1710 of formula I, wherein $X^1$, $X^2$ and $R^2$ are defined as in line P-57 of table P and the meaning of $R^1$ for each individual compound corresponds in each case to one line of table A1.

Table 142: Compounds 1711a to 1740a of formula I, wherein $X^1$, $X^2$ and $R^2$ are defined as in line P-58 of table P and the meaning of $R^1$ for each individual compound corresponds in each case to one line of table A1.

Table 143: Compounds 1741a to 1770a of formula I, wherein $X^1$, $X^2$ and $R^2$ are defined as in line P-59 of table P and the meaning of $R^1$ for each individual compound corresponds in each case to one line of table A1.

Table 144: Compounds 1771a to 1800a of formula I, wherein $X^1$, $X^2$ and $R^2$ are defined as in line P-60 of table P and the meaning of $R^1$ for each individual compound corresponds in each case to one line of table A1.

Table 145: Compounds 1801a to 1830a of formula I, wherein $X^1$, $X^2$ and $R^2$ are defined as in line P-61 of table P and the meaning of $R^1$ for each individual compound corresponds in each case to one line of table A1.

Table 146: Compounds 1831a to 1860a of formula I, wherein $X^1$, $X^2$ and $R^2$ are defined as in line P-62 of table P and the meaning of $R^1$ for each individual compound corresponds in each case to one line of table A1.

Table 147: Compounds 1861a to 1890a of formula I, wherein $X^1$, $X^2$ and $R^2$ are defined as in line P-63 of table P and the meaning of $R^1$ for each individual compound corresponds in each case to one line of table A1.

Table 148: Compounds 1891a to 1920a of formula I, wherein $X^1$, $X^2$ and $R^2$ are defined as in line P-64 of table P and the meaning of $R^1$ for each individual compound corresponds in each case to one line of table A1.

Table 149: Compounds 1921a to 1950a of formula I, wherein $X^1$, $X^2$ and $R^2$ are defined as in line P-65 of table P and the meaning of $R^1$ for each individual compound corresponds in each case to one line of table A1.

Table 150: Compounds 1951a to 1980a of formula I, wherein $X^1$, $X^2$ and $R^2$ are defined as in line P-66 of table P and the meaning of $R^1$ for each individual compound corresponds in each case to one line of table A1.

Table 151: Compounds 1981a to 2010a of formula I, wherein $X^1$, $X^2$ and $R^2$ are defined as in line P-67 of table P and the meaning of $R^1$ for each individual compound corresponds in each case to one line of table A1.

Table 152: Compounds 2011a to 2040a of formula I, wherein $X^1$, $X^2$ and $R^2$ are defined as in line P-68 of table P and the meaning of $R^1$ for each individual compound corresponds in each case to one line of table A1.

Table 153: Compounds 2041a to 2070a of formula I, wherein $X^1$, $X^2$ and $R^2$ are defined as in line P-69 of table P and the meaning of $R^1$ for each individual compound corresponds in each case to one line of table A1.

Table 154: Compounds 2071a to 2100a of formula I, wherein $X^1$, $X^2$ and $R^2$ are defined as in line P-70 of table P and the meaning of $R^1$ for each individual compound corresponds in each case to one line of table A1.

Table 155: Compounds 2101a to 2130a of formula I, wherein $X^1$, $X^2$ and $R^2$ are defined as in line P-71 of table P and the meaning of $R^1$ for each individual compound corresponds in each case to one line of table A1.

Table 156: Compounds 2131a to 2160a of formula I, wherein $X^1$, $X^2$ and $R^2$ are defined as in line P-72 of table P and the meaning of $R^1$ for each individual compound corresponds in each case to one line of table A1.

Table 157: Compounds 2161a to 2190a of formula I, wherein $X^1$, $X^2$ and $R^2$ are defined as in line P-73 of table P and the meaning of $R^1$ for each individual compound corresponds in each case to one line of table A1.

Table 158: Compounds 2191a to 2220a of formula I, wherein $X^1$, $X^2$ and $R^2$ are defined as in line P-74 of table P and the meaning of $R^1$ for each individual compound corresponds in each case to one line of table A1.

Table 159: Compounds 2221a to 2250a of formula I, wherein $X^1$, $X^2$ and $R^2$ are defined as in line P-75 of table P and the meaning of $R^1$ for each individual compound corresponds in each case to one line of table A1.

Table 160: Compounds 2251a to 2280a of formula I, wherein $X^1$, $X^2$ and $R^2$ are defined as in line P-76 of table P and the meaning of $R^1$ for each individual compound corresponds in each case to one line of table A1.

Table 161: Compounds 2281a to 2310a of formula I, wherein $X^1$, $X^2$ and $R^2$ are defined as in line P-77 of table P and the meaning of $R^1$ for each individual compound corresponds in each case to one line of table A1.

Table 162: Compounds 2311a to 2340a of formula I, wherein $X^1$, $X^2$ and $R^2$ are defined as in line P-78 of table P and the meaning of $R^1$ for each individual compound corresponds in each case to one line of table A1.

Table 163: Compounds 2341a to 2370a of formula I, wherein $X^1$, $X^2$ and $R^2$ are defined as in line P-79 of table P and the meaning of $R^1$ for each individual compound corresponds in each case to one line of table A1.

Table 164: Compounds 2371a to 2400a of formula I, wherein $X^1$, $X^2$ and $R^2$ are defined as in line P-80 of table P and the meaning of $R^1$ for each individual compound corresponds in each case to one line of table A1.

Table 165: Compounds 2401a to 2430a of formula I, wherein $X^1$, $X^2$ and $R^2$ are defined as in line P-81 of table P and the meaning of $R^1$ for each individual compound corresponds in each case to one line of table A1.

Table 166: Compounds 2431a to 2460a of formula I, wherein $X^1$, $X^2$ and $R^2$ are defined as in line P-82 of table P and the meaning of $R^1$ for each individual compound corresponds in each case to one line of table A1.

Table 167: Compounds 2461a to 2490a of formula I, wherein $X^1$, $X^2$ and $R^2$ are defined as in line P-83 of table P and the meaning of $R^1$ for each individual compound corresponds in each case to one line of table A1.

Table 168: Compounds 2491a to 2520a of formula I, wherein $X^1$, $X^2$ and $R^2$ are defined as in line P-84 of table P and the meaning of $R^1$ for each individual compound corresponds in each case to one line of table A1.

Table 168a: Compounds 2521a to 2550a of formula I, wherein $X^1$, $X^2$ and $R^2$ are defined as in line P-85 of table P and the meaning of $R^1$ for each individual compound corresponds in each case to one line of table A1.

Table 168b: Compounds 2551a to 2580a of formula I, wherein $X^1$, $X^2$ and $R^2$ are defined as in line P-86 of table P and the meaning of $R^1$ for each individual compound corresponds in each case to one line of table A1.

Table 168c: Compounds 2581a to 2610a of formula I, wherein $X^1$, $X^2$ and $R^2$ are defined as in line P-87 of table P and the meaning of $R^1$ for each individual compound corresponds in each case to one line of table A1.

Table 168d: Compounds 2611a to 2640a of formula I, wherein $X^1$, $X^2$ and $R^2$ are defined as in line P-88 of table P and the meaning of $R^1$ for each individual compound corresponds in each case to one line of table A1.

Table 168e: Compounds 2641a to 2670a of formula I, wherein $X^1$, $X^2$ and $R^2$ are defined as in line P-89 of table P and the meaning of $R^1$ for each individual compound corresponds in each case to one line of table A1.

Table 168f: Compounds 2671a to 2700a of formula I, wherein $X^1$, $X^2$ and $R^2$ are defined as in line P-90 of table P and the meaning of $R^1$ for each individual compound corresponds in each case to one line of table A1.

Table 168g: Compounds 2701a to 2730a of formula I, wherein $X^1$, $X^2$ and $R^2$ are defined as in line P-91 of table P and the meaning of $R^1$ for each individual compound corresponds in each case to one line of table A1.

Table 168h: Compounds 2731a to 2760a of formula I, wherein $X^1$, $X^2$ and $R^2$ are defined as in line P-92 of table P and the meaning of $R^1$ for each individual compound corresponds in each case to one line of table A1.

Table 168i: Compounds 2761a to 2790a of formula I, wherein $X^1$, $X^2$ and $R^2$ are defined as in line P-93 of table P and the meaning of $R^1$ for each individual compound corresponds in each case to one line of table A1.

Table 168j: Compounds 2791a to 2820a of formula I, wherein $X^1$, $X^2$ and $R^2$ are defined as in line P-94 of table P and the meaning of $R^1$ for each individual compound corresponds in each case to one line of table A1.

Table 168k: Compounds 2821a to 2850a of formula I, wherein $X^1$, $X^2$ and $R^2$ are defined as in line P-95 of table P and the meaning of $R^1$ for each individual compound corresponds in each case to one line of table A1.

Table 168l: Compounds 2851a to 2880a of formula I, wherein $X^1$, $X^2$ and $R^2$ are defined as in line P-96 of table P and the meaning of $R^1$ for each individual compound corresponds in each case to one line of table A1.

Table 168m: Compounds 2881a to 2910a of formula I, wherein $X^1$, $X^2$ and $R^2$ are defined as in line P-97 of table P and the meaning of $R^1$ for each individual compound corresponds in each case to one line of table A1.

Table 168n: Compounds 2911a to 2940a of formula I, wherein $X^1$, $X^2$ and $R^2$ are defined as in line P-98 of table P and the meaning of $R^1$ for each individual compound corresponds in each case to one line of table A1.

Table 168o: Compounds 2941a to 2970a of formula I, wherein $X^1$, $X^2$ and $R^2$ are defined as in line P-99 of table P and the meaning of $R^1$ for each individual compound corresponds in each case to one line of table A1.

Table 168p: Compounds 2971a to 3000a of formula I, wherein $X^1$, $X^2$ and $R^2$ are defined as in line P-100 of table P and the meaning of $R^1$ for each individual compound corresponds in each case to one line of table A1.

Table 168q: Compounds 3001a to 3030a of formula I, wherein $X^1$, $X^2$ and $R^2$ are defined as in line P-101 of table P and the meaning of $R^1$ for each individual compound corresponds in each case to one line of table A1.

Table 168r: Compounds 3031a to 3060a of formula I, wherein $X^1$, $X^2$ and $R^2$ are defined as in line P-102 of table P and the meaning of $R^1$ for each individual compound corresponds in each case to one line of table A1.

Table 168s: Compounds 3061a to 3090a of formula I, wherein $X^1$, $X^2$ and $R^2$ are defined as in line P-103 of table P and the meaning of $R^1$ for each individual compound corresponds in each case to one line of table A1.

Table 168t: Compounds 3091a to 3120a of formula I, wherein $X^1$, $X^2$ and $R^2$ are defined as in line P-104 of table P and the meaning of $R^1$ for each individual compound corresponds in each case to one line of table A1.

Table 168u: Compounds 3121a to 3150a of formula I, wherein $X^1$, $X^2$ and $R^2$ are defined as in line P-105 of table P and the meaning of $R^1$ for each individual compound corresponds in each case to one line of table A1.

Table 168v: Compounds 3151a to 3180a of formula I, wherein $X^1$, $X^2$ and $R^2$ are defined as in line P-106 of table P and the meaning of $R^1$ for each individual compound corresponds in each case to one line of table A1.

Table 168w: Compounds 3181a to 3210a of formula I, wherein $X^1$, $X^2$ and $R^2$ are defined as in line P-107 of table P and the meaning of $R^1$ for each individual compound corresponds in each case to one line of table A1.

Table 168x: Compounds 3211a to 3240a of formula I, wherein $X^1$, $X^2$ and $R^2$ are defined as in line P-108 of table P and the meaning of $R^1$ for each individual compound corresponds in each case to one line of table A1.

Table 169: Compounds 1b to 30b of formula I, wherein $X^1$, $X^2$ and $R^2$ are defined as in line P-1 of table P and the meaning of $R^1$ for each individual compound corresponds in each case to one line of table A2.

Table 170: Compounds 31b to 60b of formula I, wherein $X^1$, $X^2$ and $R^2$ are defined as in line P-2 of table P and the meaning of $R^1$ for each individual compound corresponds in each case to one line of table A2.

Table 171: Compounds 61b to 90b of formula I, wherein $X^1$, $X^2$ and $R^2$ are defined as in line P-3 of table P and the meaning of $R^1$ for each individual compound corresponds in each case to one line of table A2.

Table 172: Compounds 91b to 120b of formula I, wherein $X^1$, $X^2$ and $R^2$ are defined as in line P-4 of table P and the meaning of $R^1$ for each individual compound corresponds in each case to one line of table A2.

Table 173: Compounds 121b to 150b of formula I, wherein $X^1$, $X^2$ and $R^2$ are defined as in line P-5 of table P and the meaning of $R^1$ for each individual compound corresponds in each case to one line of table A2.

Table 174: Compounds 151b to 180b of formula I, wherein $X^1$, $X^2$ and $R^2$ are defined as in line P-6 of table P and the meaning of $R^1$ for each individual compound corresponds in each case to one line of table A2.

Table 175: Compounds 181b to 210b of formula I, wherein $X^1$, $X^2$ and $R^2$ are defined as in line P-7 of table P and the meaning of $R^1$ for each individual compound corresponds in each case to one line of table A2.

Table 176: Compounds 211b to 240b of formula I, wherein $X^1$, $X^2$ and $R^2$ are defined as in line P-8 of table P and the meaning of $R^1$ for each individual compound corresponds in each case to one line of table A2.

Table 177: Compounds 241b to 270b of formula I, wherein $X^1$, $X^2$ and $R^2$ are defined as in line P-9 of table P and the meaning of $R^1$ for each individual compound corresponds in each case to one line of table A2.

Table 178: Compounds 271b to 300b of formula I, wherein $X^1$, $X^2$ and $R^2$ are defined as in line P-10 of table P and the meaning of $R^1$ for each individual compound corresponds in each case to one line of table A2.

Table 179: Compounds 301b to 330b of formula I, wherein $X^1$, $X^2$ and $R^2$ are defined as in line P-11 of table P and the meaning of $R^1$ for each individual compound corresponds in each case to one line of table A2.

Table 180: Compounds 331b to 360b of formula I, wherein $X^1$, $X^2$ and $R^2$ are defined as in line P-12 of table P and the meaning of $R^1$ for each individual compound corresponds in each case to one line of table A2.

Table 181: Compounds 361b to 390b of formula I, wherein $X^1$, $X^2$ and $R^2$ are defined as in line P-13 of table P and the meaning of $R^1$ for each individual compound corresponds in each case to one line of table A2.

Table 182: Compounds 391b to 420b of formula I, wherein $X^1$, $X^2$ and $R^2$ are defined as in line P-14 of table P and the meaning of $R^1$ for each individual compound corresponds in each case to one line of table A2.

Table 183: Compounds 421b to 450b of formula I, wherein $X^1$, $X^2$ and $R^2$ are defined as in line P-15 of table P and the meaning of $R^1$ for each individual compound corresponds in each case to one line of table A2.

Table 184: Compounds 451b to 480b of formula I, wherein $X^1$, $X^2$ and $R^2$ are defined as in line P-16 of table P and the meaning of $R^1$ for each individual compound corresponds in each case to one line of table A2.

Table 185: Compounds 481b to 510b of formula I, wherein $X^1$, $X^2$ and $R^2$ are defined as in line P-17 of table P and the meaning of $R^1$ for each individual compound corresponds in each case to one line of table A2.

Table 186: Compounds 511b to 540b of formula I, wherein $X^1$, $X^2$ and $R^2$ are defined as in line P-18 of table P and the meaning of $R^1$ for each individual compound corresponds in each case to one line of table A2.

Table 187: Compounds 541b to 570b of formula I, wherein $X^1$, $X^2$ and $R^2$ are defined as in line P-19 of table P and the meaning of $R^1$ for each individual compound corresponds in each case to one line of table A2.

Table 188: Compounds 571b to 600b of formula I, wherein $X^1$, $X^2$ and $R^2$ are defined as in line P-20 of table P and the meaning of $R^1$ for each individual compound corresponds in each case to one line of table A2.

Table 189: Compounds 601b to 630b of formula I, wherein $X^1$, $X^2$ and $R^2$ are defined as in line P-21 of table P and the meaning of $R^1$ for each individual compound corresponds in each case to one line of table A2.

Table 190: Compounds 631b to 660b of formula I, wherein $X^1$, $X^2$ and $R^2$ are defined as in line P-22 of table P and the meaning of $R^1$ for each individual compound corresponds in each case to one line of table A2.

Table 191: Compounds 661b to 690b of formula I, wherein $X^1$, $X^2$ and $R^2$ are defined as in line P-23 of table P and the meaning of $R^1$ for each individual compound corresponds in each case to one line of table A2.

Table 192: Compounds 691b to 720b of formula I, wherein $X^1$, $X^2$ and $R^2$ are defined as in line P-24 of table P and the meaning of $R^1$ for each individual compound corresponds in each case to one line of table A2.

Table 193: Compounds 721b to 750b of formula I, wherein $X^1$, $X^2$ and $R^2$ are defined as in line P-25 of table P and the meaning of $R^1$ for each individual compound corresponds in each case to one line of table A2.

Table 194: Compounds 751b to 780b of formula I, wherein $X^1$, $X^2$ and $R^2$ are defined as in line P-26 of table P and the meaning of $R^1$ for each individual compound corresponds in each case to one line of table A2.

Table 195: Compounds 781b to 810b of formula I, wherein $X^1$, $X^2$ and $R^2$ are defined as in line P-27 of table P and the meaning of $R^1$ for each individual compound corresponds in each case to one line of table A2.

Table 196: Compounds 811b to 840b of formula I, wherein $X^1$, $X^2$ and $R^2$ are defined as in line P-28 of table P and the meaning of $R^1$ for each individual compound corresponds in each case to one line of table A2.

Table 197: Compounds 841b to 870b of formula I, wherein $X^1$, $X^2$ and $R^2$ are defined as in line P-29 of table P and the meaning of $R^1$ for each individual compound corresponds in each case to one line of table A2.

Table 198: Compounds 871b to 900b of formula I, wherein $X^1$, $X^2$ and $R^2$ are defined as in line P-30 of table P and the meaning of $R^1$ for each individual compound corresponds in each case to one line of table A2.

Table 199: Compounds 901b to 930b of formula I, wherein $X^1$, $X^2$ and $R^2$ are defined as in line P-31 of table P and the meaning of $R^1$ for each individual compound corresponds in each case to one line of table A2.

Table 200: Compounds 931b to 960b of formula I, wherein $X^1$, $X^2$ and $R^2$ are defined as in line P-32 of table P and the meaning of $R^1$ for each individual compound corresponds in each case to one line of table A2.

Table 201: Compounds 961b to 990b of formula I, wherein $X^1$, $X^2$ and $R^2$ are defined as in line P-33 of table P and the meaning of $R^1$ for each individual compound corresponds in each case to one line of table A2.

Table 202: Compounds 991b to 1020b of formula I, wherein $X^1$, $X^2$ and $R^2$ are defined as in line P-34 of table P and the meaning of $R^1$ for each individual compound corresponds in each case to one line of table A2.

Table 203: Compounds 1021b to 1050b of formula I, wherein $X^1$, $X^2$ and $R^2$ are defined as in line P-35 of table P and the meaning of $R^1$ for each individual compound corresponds in each case to one line of table A2.

Table 204: Compounds 1051b to 1080b of formula I, wherein $X^1$, $X^2$ and $R^2$ are defined as in line P-36 of table P and the meaning of $R^1$ for each individual compound corresponds in each case to one line of table A2.

Table 205: Compounds 1081b to 1110b of formula I, wherein $X^1$, $X^2$ and $R^2$ are defined as in line P-37 of table P and the meaning of $R^1$ for each individual compound corresponds in each case to one line of table A2.

Table 206: Compounds 1111b to 1140b of formula I, wherein $X^1$, $X^2$ and $R^2$ are defined as in line P-38 of table P and the meaning of $R^1$ for each individual compound corresponds in each case to one line of table A2.

Table 207: Compounds 1141b to 1170b of formula I, wherein $X^1$, $X^2$ and $R^2$ are defined as in line P-39 of table P and the meaning of $R^1$ for each individual compound corresponds in each case to one line of table A2.

Table 208: Compounds 1171b to 1200b of formula I, wherein $X^1$, $X^2$ and $R^2$ are defined as in line P-40 of table P and the meaning of $R^1$ for each individual compound corresponds in each case to one line of table A2.

Table 209: Compounds 1201b to 1230b of formula I, wherein $X^1$, $X^2$ and $R^2$ are defined as in line P-41 of table P and the meaning of $R^1$ for each individual compound corresponds in each case to one line of table A2.

Table 210: Compounds 1231b to 1260b of formula I, wherein $X^1$, $X^2$ and $R^2$ are defined as in line P-42 of table P and the meaning of $R^1$ for each individual compound corresponds in each case to one line of table A2.

Table 211: Compounds 1261b to 1290b of formula I, wherein $X^1$, $X^2$ and $R^2$ are defined as in line P-43 of table P and the meaning of $R^1$ for each individual compound corresponds in each case to one line of table A2.

Table 212: Compounds 1291b to 1320b of formula I, wherein $X^1$, $X^2$ and $R^2$ are defined as in line P-44 of table P and the meaning of $R^1$ for each individual compound corresponds in each case to one line of table A2.

Table 213: Compounds 1321b to 1350b of formula I, wherein $X^1$, $X^2$ and $R^2$ are defined as in line P-45 of table P and the meaning of $R^1$ for each individual compound corresponds in each case to one line of table A2.

Table 214: Compounds 1351b to 1380b of formula I, wherein $X^1$, $X^2$ and $R^2$ are defined as in line P-46 of table P and the meaning of $R^1$ for each individual compound corresponds in each case to one line of table A2.

Table 215: Compounds 1381b to 1410b of formula I, wherein $X^1$, $X^2$ and $R^2$ are defined as in line P-47 of table P and the meaning of $R^1$ for each individual compound corresponds in each case to one line of table A2.

Table 216: Compounds 1411b to 1440b of formula I, wherein $X^1$, $X^2$ and $R^2$ are defined as in line P-48 of table P and the meaning of $R^1$ for each individual compound corresponds in each case to one line of table A2.

Table 217: Compounds 1441b to 1470b of formula I, wherein $X^1$, $X^2$ and $R^2$ are defined as in line P-49 of table P and the meaning of $R^1$ for each individual compound corresponds in each case to one line of table A2.

Table 218: Compounds 1471b to 1500b of formula I, wherein $X^1$, $X^2$ and $R^2$ are defined as in line P-50 of table P and the meaning of $R^1$ for each individual compound corresponds in each case to one line of table A2.

Table 219: Compounds 1501b to 1530b of formula I, wherein $X^1$, $X^2$ and $R^2$ are defined as in line P-51 of table P and the meaning of $R^1$ for each individual compound corresponds in each case to one line of table A2.

Table 220: Compounds 1531b to 1560b of formula I, wherein $X^1$, $X^2$ and $R^2$ are defined as in line P-52 of table P and the meaning of $R^1$ for each individual compound corresponds in each case to one line of table A2.

Table 221: Compounds 1561b to 1590b of formula I, wherein $X^1$, $X^2$ and $R^2$ are defined as in line P-53 of table P and the meaning of $R^1$ for each individual compound corresponds in each case to one line of table A2.

Table 222: Compounds 1591b to 1620b of formula I, wherein $X^1$, $X^2$ and $R^2$ are defined as in line P-54 of table P and the meaning of $R^1$ for each individual compound corresponds in each case to one line of table A2.

Table 223: Compounds 1621b to 1650b of formula I, wherein $X^1$, $X^2$ and $R^2$ are defined as in line P-55 of table P and the meaning of $R^1$ for each individual compound corresponds in each case to one line of table A2.

Table 224: Compounds 1651b to 1680b of formula I, wherein $X^1$, $X^2$ and $R^2$ are defined as in line P-56 of table P and the meaning of $R^1$ for each individual compound corresponds in each case to one line of table A2.

Table 225: Compounds 1681b to 1710b of formula I, wherein $X^1$, $X^2$ and $R^2$ are defined as in line P-57 of table P and the meaning of $R^1$ for each individual compound corresponds in each case to one line of table A2.

Table 226: Compounds 1711b to 1740b of formula I, wherein $X^1$, $X^2$ and $R^2$ are defined as in line P-58 of table P and the meaning of $R^1$ for each individual compound corresponds in each case to one line of table A2.

Table 227: Compounds 1741b to 1770b of formula I, wherein $X^1$, $X^2$ and $R^2$ are defined as in line P-59 of table P and the meaning of $R^1$ for each individual compound corresponds in each case to one line of table A2.

Table 228: Compounds 1771b to 1800b of formula I, wherein $X^1$, $X^2$ and $R^2$ are defined as in line P-60 of table P and the meaning of $R^1$ for each individual compound corresponds in each case to one line of table A2.

Table 229: Compounds 1801b to 1830b of formula I, wherein $X^1$, $X^2$ and $R^2$ are defined as in line P-61 of table P and the meaning of $R^1$ for each individual compound corresponds in each case to one line of table A2.

Table 230: Compounds 1831b to 1860b of formula I, wherein $X^1$, $X^2$ and $R^2$ are defined as in line P-62 of table P and the meaning of $R^1$ for each individual compound corresponds in each case to one line of table A2.

Table 231: Compounds 1861b to 1890b of formula I, wherein $X^1$, $X^2$ and $R^2$ are defined as in line P-63 of table P and the meaning of $R^1$ for each individual compound corresponds in each case to one line of table A2.

Table 232: Compounds 1891b to 1920b of formula I, wherein $X^1$, $X^2$ and $R^2$ are defined as in line P-64 of table P and the meaning of $R^1$ for each individual compound corresponds in each case to one line of table A2.

Table 233: Compounds 1921b to 1950b of formula I, wherein $X^1$, $X^2$ and $R^2$ are defined as in line P-65 of table P and the meaning of $R^1$ for each individual compound corresponds in each case to one line of table A2.

Table 234: Compounds 1951b to 1980b of formula I, wherein $X^1$, $X^2$ and $R^2$ are defined as in line P-66 of table P and the meaning of $R^1$ for each individual compound corresponds in each case to one line of table A2.

Table 235: Compounds 1981b to 2010b of formula I, wherein $X^1$, $X^2$ and $R^2$ are defined as in line P-67 of table P and the meaning of $R^1$ for each individual compound corresponds in each case to one line of table A2.

Table 236: Compounds 2011b to 2040b of formula I, wherein $X^1$, $X^2$ and $R^2$ are defined as in line P-68 of table P and the meaning of $R^1$ for each individual compound corresponds in each case to one line of table A2.

Table 237: Compounds 2041b to 2070b of formula I, wherein $X^1$, $X^2$ and $R^2$ are defined as in line P-69 of table P and the meaning of $R^1$ for each individual compound corresponds in each case to one line of table A2.

Table 238: Compounds 2071b to 2100b of formula I, wherein $X^1$, $X^2$ and $R^2$ are defined as in line P-70 of table P and the meaning of $R^1$ for each individual compound corresponds in each case to one line of table A2.

Table 239: Compounds 2101b to 2130b of formula I, wherein $X^1$, $X^2$ and $R^2$ are defined as in line P-71 of table P and the meaning of $R^1$ for each individual compound corresponds in each case to one line of table A2.

Table 240: Compounds 2131b to 2160b of formula I, wherein $X^1$, $X^2$ and $R^2$ are defined as in line P-72 of table P and the meaning of $R^1$ for each individual compound corresponds in each case to one line of table A2.

Table 241: Compounds 2161b to 2190b of formula I, wherein $X^1$, $X^2$ and $R^2$ are defined as in line P-73 of table P and the meaning of $R^1$ for each individual compound corresponds in each case to one line of table A2.

Table 242: Compounds 2191b to 2220b of formula I, wherein $X^1$, $X^2$ and $R^2$ are defined as in line P-74 of table P and the meaning of $R^1$ for each individual compound corresponds in each case to one line of table A2.

Table 243: Compounds 2221b to 2250b of formula I, wherein $X^1$, $X^2$ and $R^2$ are defined as in line P-75 of table P and the meaning of $R^1$ for each individual compound corresponds in each case to one line of table A2.

Table 244: Compounds 2251b to 2280b of formula I, wherein $X^1$, $X^2$ and $R^2$ are defined as in line P-76 of table P and the meaning of $R^1$ for each individual compound corresponds in each case to one line of table A2.

Table 245: Compounds 2281b to 2310b of formula I, wherein $X^1$, $X^2$ and $R^2$ are defined as in line P-77 of table P and the meaning of $R^1$ for each individual compound corresponds in each case to one line of table A2.

Table 246: Compounds 2311b to 2340b of formula I, wherein $X^1$, $X^2$ and $R^2$ are defined as in line P-78 of table P and the meaning of $R^1$ for each individual compound corresponds in each case to one line of table A2.

Table 247: Compounds 2341b to 2370b of formula I, wherein $X^1$, $X^2$ and $R^2$ are defined as in line P-79 of table P and the meaning of $R^1$ for each individual compound corresponds in each case to one line of table A2.

Table 248: Compounds 2371b to 2400b of formula I, wherein $X^1$, $X^2$ and $R^2$ are defined as in line P-80 of table P and the meaning of $R^1$ for each individual compound corresponds in each case to one line of table A2.

Table 249: Compounds 2401b to 2430b of formula I, wherein $X^1$, $X^2$ and $R^2$ are defined as in line P-81 of table P and the meaning of $R^1$ for each individual compound corresponds in each case to one line of table A2.

Table 250: Compounds 2431b to 2460b of formula I, wherein $X^1$, $X^2$ and $R^2$ are defined as in line P-82 of table P and the meaning of $R^1$ for each individual compound corresponds in each case to one line of table A2.

Table 251: Compounds 2461b to 2490b of formula I, wherein $X^1$, $X^2$ and $R^2$ are defined as in line P-83 of table P and the meaning of $R^1$ for each individual compound corresponds in each case to one line of table A2.

Table 252: Compounds 2491b to 2520b of formula I, wherein $X^1$, $X^2$ and $R^2$ are defined as in line P-84 of table P and the meaning of $R^1$ for each individual compound corresponds in each case to one line of table A2.

Table 252a: Compounds 2521b to 2550b of formula I, wherein $X^1$, $X^2$ and $R^2$ are defined as in line P-85 of table P and the meaning of $R^1$ for each individual compound corresponds in each case to one line of table A2.

Table 252b: Compounds 2551b to 2580b of formula I, wherein $X^1$, $X^2$ and $R^2$ are defined as in line P-86 of table P and the meaning of $R^1$ for each individual compound corresponds in each case to one line of table A2.

Table 252c: Compounds 2581b to 2610b of formula I, wherein $X^1$, $X^2$ and $R^2$ are defined as in line P-87 of table P and the meaning of $R^1$ for each individual compound corresponds in each case to one line of table A2.

Table 252d: Compounds 2611b to 2640b of formula I, wherein $X^1$, $X^2$ and $R^2$ are defined as in line P-88 of table P and the meaning of $R^1$ for each individual compound corresponds in each case to one line of table A2.

Table 252e: Compounds 2641b to 2670b of formula I, wherein $X^1$, $X^2$ and $R^2$ are defined as in line P-89 of table P and the meaning of $R^1$ for each individual compound corresponds in each case to one line of table A2.

Table 252f: Compounds 2671b to 2700b of formula I, wherein $X^1$, $X^2$ and $R^2$ are defined as in line P-90 of table P and the meaning of $R^1$ for each individual compound corresponds in each case to one line of table A2.

Table 252g: Compounds 2701b to 2730b of formula I, wherein $X^1$, $X^2$ and $R^2$ are defined as in line P-91 of table P and the meaning of $R^1$ for each individual compound corresponds in each case to one line of table A2.

Table 252h: Compounds 2731b to 2760b of formula I, wherein $X^1$, $X^2$ and $R^2$ are defined as in line P-92 of table P and the meaning of $R^1$ for each individual compound corresponds in each case to one line of table A2.

Table 252i: Compounds 2761b to 2790b of formula I, wherein $X^1$, $X^2$ and $R^2$ are defined as in line P-93 of table P and the meaning of $R^1$ for each individual compound corresponds in each case to one line of table A2.

Table 252j: Compounds 2791b to 2820b of formula I, wherein $X^1$, $X^2$ and $R^2$ are defined as in line P-94 of table P and the meaning of $R^1$ for each individual compound corresponds in each case to one line of table A2.

Table 252k: Compounds 2821b to 2850b of formula I, wherein $X^1$, $X^2$ and $R^2$ are defined as in line P-95 of table P and the meaning of $R^1$ for each individual compound corresponds in each case to one line of table A2.

Table 252l: Compounds 2851b to 2880b of formula I, wherein $X^1$, $X^2$ and $R^2$ are defined as in line P-96 of table P and the meaning of $R^1$ for each individual compound corresponds in each case to one line of table A2.

Table 252m: Compounds 2881b to 2910b of formula I, wherein $X^1$, $X^2$ and $R^2$ are defined as in line P-97 of table P and the meaning of $R^1$ for each individual compound corresponds in each case to one line of table A2.

Table 252n: Compounds 2911b to 2940b of formula I, wherein $X^1$, $X^2$ and $R^2$ are defined as in line P-98 of table P and the meaning of $R^1$ for each individual compound corresponds in each case to one line of table A2.

Table 252o: Compounds 2941b to 2970b of formula I, wherein $X^1$, $X^2$ and $R^2$ are defined as in line P-99 of table P and the meaning of $R^1$ for each individual compound corresponds in each case to one line of table A2.

Table 252p: Compounds 2971b to 3000b of formula I, wherein $X^1$, $X^2$ and $R^2$ are defined as in line P-100 of table P and the meaning of $R^1$ for each individual compound corresponds in each case to one line of table A2.

Table 252q: Compounds 3001b to 3030b of formula I, wherein $X^1$, $X^2$ and $R^2$ are defined as in line P-101 of table P and the meaning of $R^1$ for each individual compound corresponds in each case to one line of table A2.

Table 252r: Compounds 3031b to 3060b of formula I, wherein $X^1$, $X^2$ and $R^2$ are defined as in line P-102 of table P and the meaning of $R^1$ for each individual compound corresponds in each case to one line of table A2.

Table 252s: Compounds 3061b to 3090b of formula I, wherein $X^1$, $X^2$ and $R^2$ are defined as in line P-103 of table P and the meaning of $R^1$ for each individual compound corresponds in each case to one line of table A2.

Table 252t: Compounds 3091b to 3120b of formula I, wherein $X^1$, $X^2$ and $R^2$ are defined as in line P-104 of table P and the meaning of $R^1$ for each individual compound corresponds in each case to one line of table A2.

Table 252u: Compounds 3121b to 3150b of formula I, wherein $X^1$, $X^2$ and $R^2$ are defined as in line P-105 of table P and the meaning of $R^1$ for each individual compound corresponds in each case to one line of table A2.

Table 252v: Compounds 3151b to 3180b of formula I, wherein $X^1$, $X^2$ and $R^2$ are defined as in line P-106 of table P and the meaning of $R^1$ for each individual compound corresponds in each case to one line of table A2.

Table 252w: Compounds 3181b to 3210b of formula I, wherein $X^1$, $X^2$ and $R^2$ are defined as in line P-107 of table P and the meaning of $R^1$ for each individual compound corresponds in each case to one line of table A2.

Table 252x: Compounds 3211b to 3240b of formula I, wherein $X^1$, $X^2$ and $R^2$ are defined as in line P-108 of table P and the meaning of $R^1$ for each individual compound corresponds in each case to one line of table A2.

TABLE A

| line | $R^1$ |
| --- | --- |
| A-1 | H |
| A-2 | $CH_3$ |
| A-3 | $CH_2CH_3$ |
| A-4 | $CH_2CH_2CH_3$ |
| A-5 | $CH(CH_3)_2$ |
| A-6 | $C_3H_5$ (cyclopropyl) |
| A-7 | $C_6H_5$ |
| A-8 | $CH_2-C_6H_5$ |
| A-9 | $CF_3$ |
| A-10 | $CHF_2$ |
| A-11 | $CH_2-CN$ |
| A-12 | $CH_2CH_2-CN$ |

TABLE A-continued

| line | $R^1$ |
|---|---|
| A-13 | C≡CH |
| A-14 | C≡CCH₃ |
| A-15 | C₅H₉ (cyclopentyl) |
| A-16 | C₆H₁₁ (cyclohexyl) |
| A-17 | CH₂CH₂CH₂CH₃ |
| A-18 | CH₂—C₃H₅ |
| A-19 | CH₂C≡CH |
| A-20 | 4-F—C₆H₄ |
| A-21 | 4-Cl—C₆H₄ |
| A-22 | 2,4-Cl₂—C₆H₃ |
| A-23 | 2,4,6-Cl₃—C₆H₂ |
| A-24 | 2,4,6-F₃—C₆H₂ |
| A-25 | CH₂—C₆H₅ |
| A-26 | CH₂-(4-F—C₆H₄) |
| A-27 | CH₂-(4-Cl—C₆H₄) |
| A-28 | CH=CH—C₆H₅ |
| A-29 | CH=CH-(4-F—C₆H₄) |
| A-30 | CH=CH-(4-Cl—C₆H₄) |

TABLE A1

| line | $R^1$ |
|---|---|
| A1-1 | CH(CH₂CH₃)₂ |
| A1-2 | C(CH₃)₂ |
| A1-3 | CH₂CH(CH₃)₂ |
| A1-4 | CH₂CH₂CH₂CH₂CH₃ |
| A1-5 | CH(CH₃)—CH(CH₃)₂ |
| A1-6 | CH=CH₂ |
| A1-7 | CH=CHCH₃ |
| A1-8 | CH₂CH=CH₂ |
| A1-9 | C(CH₃)=CH₂ |
| A1-10 | CH=CHCH₂CH₃ |
| A1-11 | CH₂CH=CHCH₃ |
| A1-12 | CH₂CH₂CH=CH₂ |
| A1-13 | CH(CH=CH₂)₂ |
| A1-14 | CH=C(CH₃)₂ |
| A1-15 | CH=CHCH₂CH₂CH₃ |
| A1-16 | CH=CHCH₂CH₂CH₂CH₃ |
| A1-17 | CH=CHC(CH₃)₂ |
| A1-18 | C≡CCH₂CH₃ |
| A1-19 | CH₂C≡CCH₃ |
| A1-20 | CH₂CH₂C≡CH |
| A1-21 | CH(C≡CH)₂ |
| A1-22 | C≡CCH₂CH₂CH₃ |
| A1-23 | C≡CCH(CH₃)₂ |
| A1-24 | C≡CCH₂CH₂CH₂CH₃ |
| A1-25 | C≡CC(CH₃)₃ |
| A1-26 | 1-Cl-cyclopropyl |
| A1-27 | 1-F-cyclopropyl |
| A1-28 | CH₂C(CH₃)=CH₂ |
| A1-29 | CH(CH₃)CH₂CH₃ |
| A1-30 | CH₂C≡CCH₂CH₃ |

TABLE A2

| line | $R^1$ |
|---|---|
| A2-1 | CH(CH₃)C₃H₅ |
| A2-2 | 1-CH₃-cyclopropyl |
| A2-3 | 1-CN-cyclopropyl |
| A2-4 | CH(CH₃)CN |
| A2-5 | 4-OCH₃—C₆H₄ |
| A2-6 | 4-CH₃—C₆H₄ |
| A2-7 | CH₂-(4-CH₃—C₆H₄) |
| A2-8 | CH₂-(4-OCH₃—C₆H₄) |
| A2-9 | CH₂-(2,4-Cl₂—C₆H₃) |
| A2-10 | CH₂-(2,4-F₂—C₆H₃) |
| A2-11 | CH₂OCH₃ |
| A2-12 | CH₂OCH₂CH₃ |
| A2-13 | CH(CH₃)OCH₃ |
| A2-14 | CH(CH₃)OCH₂CH₃ |
| A2-15 | CH₂CH₂CF₃ |

TABLE A2-continued

| line | $R^1$ |
|---|---|
| A2-16 | CH₂CH₂CH₂CF₃ |
| A2-17 | CH=CHCH₂OCH₃ |
| A2-18 | CH₂OCH₂CH₂CH₃ |
| A2-19 | CH₂CH₂CH₂CN |
| A2-20 | CH₂—C₆H₁₁ |
| A2-21 | CH₂—C₅H₉ |
| A2-22 | CH=CCl₂ |
| A2-23 | CH(CH₃)CN |
| A2-24 | CH=CHOCH₃ |
| A2-25 | C(CH₃)₂—C₃H₅ |
| A2-26 | CH₂—C=C—CH(CH₃)₂ |
| A2-27 | CH₂C≡CC(CH₃)₃ |
| A2-28 | CH₂C≡CCH₂OCH₃ |
| A2-29 | CH₂CH₂OCH₃ |
| A2-30 | CH₂CH(OCH₃)₂ |

The compounds I and VIII and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and VIII and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and VIII, respectively and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and VIII, respectively and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or Express-Sun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds I and VIII, respectively, and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporiodes*); *Corticium* spp., e.g. *C. sasakii* blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyre*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticilliodes* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bedwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphda* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e.g. *P. olyzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctoma* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cereags* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotima* spp. (stem rot or white mold) on vegetables and field crops, such as rape, sunflowers (e.g. *S. sclerotiorum*) and soybeans (e.g. *S. rolfsii* or *S. sclerotiorum*); *Septona* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaena* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Ventura* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and VIII, respectively, and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Scierophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecdomyces* spp. and Zygomycetes such as *Mucor* spp., and in addition in the protection of stored products and harvest the following yeast fungi are worthy of note: *Candida* spp. and *Saccharomyces cerevisae*.

The compounds I and VIII, respectively, and compositions thereof, respectively, may be used for improving the health of a plant. The invention also relates to a method for improving plant health by treating a plant, its propagation material and/or the locus where the plant is growing or is to grow with an effective amount of compounds I and VIII, respectively, and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I and VIII, respectively, can be present in different crystal modifications whose biological activity may differ. They are likewise subject matter of the present invention.

The compounds I and VIII, respectively, are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I and VIII, respectively, as such or a composition comprising at least one compound I and VIII, respectively, prophylactically either at or before planting or transplanting.

The invention also relates to agrochemical compositions comprising an auxiliary and at least one compound I and VIII, respectively, according to the invention.

An agrochemical composition comprises a fungicidally effective amount of a compound I or VIII, respectively. The term "effective amount" denotes an amount of the composition or of the compounds I or VIII, respectively, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I or VIII, respectively, used.

The compounds I or VIII, respectively, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-soluble concentrates (SL, LS)

10-60 wt % of a compound I or VIII, respectively, and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of a compound I or VIII, respectively, and 1-10 wt % dispersant (e.g. polyvinylpyrrolidone) are dissolved in organic solvent (e.g. cyclohexanone) ad 100 wt %. Dilution with water gives a dispersion.

iii) Emulsifiable concentrates (EC)

15-70 wt % of a compound I or VIII, respectively, and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I or VIII, respectively, and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I or VIII, respectively, are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of a compound I or VIII, respectively, are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)

50-80 wt % of a compound I or VIII, respectively, are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I or VIII, respectively, are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I or VIII, respectively, are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I or VIII, respectively, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly (meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % of a compound I or VIII, respectively, are ground finely and mixed intimately with solid carrier (e.g. finely divided kaolin) ad 100 wt %.

x) Granules (GR, FG)

0.5-30 wt % of a compound I or VIII, respectively, is ground finely and associated with solid carrier (e.g. silicate) ad 100 wt %. Granulation is achieved by extrusion, spray-drying or fluidized bed.

xi) Ultra-low volume liquids (UL)

1-50 wt % of a compound I or VIII, respectively, are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I or VIII, respectively, and compositions thereof, respectively, on to plant propagation material, especially seeds include dressing, coating, pelleting, dusting, soaking and in-furrow application methods of the propagation material. Preferably, compound I or VIII, respectively, or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or VIII, respectively, or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I or VIII, respectively, can be used, is intended to illustrate the possible combinations but does not limit them:

A) Respiration inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl) phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl] amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl) amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex II (e.g. carboxamides): benodanil, bixafen, boscalid, carboxin, fenfuram, fluopyram, flutolanil, fluxapyroxad, furametpyr, isopyrazam, mepronil, oxylcarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide; 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluorometh-yl)-1,5-dimethyl-N-(1,1,3-trimethylindan-4-yl)pyrazole-4-carboxamide, 3-(difluoro-methyl)-1,5-dimethyl-N-(1,1,3-trimethylindan-4-yl)pyrazole-4-carboxamide, 1,3,5-tri-methyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, [rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic acid synthesis inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy) pyrimidin-4-amine;

D) Inhibitors of cell division and cytoskeleton tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1, 2,4]triazolo[1,5-a]pyrimidine other cell division inhibitors: diethofencarb, ethaboxam, pencycuron, fluopicolide, zoxamide, metrafenone, pyriofenone;

E) Inhibitors of amino acid and protein synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloridehydrate, mildiomycin, streptomycin, oxytetracyclin, polyoxine, validamycin A;

F) Signal transduction inhibitors
MAP/histidine kinase inhibitors: fluoroimid, iprodione, procymidone, vinclozolin, fenpiclonil, fludioxonil;
G protein inhibitors: quinoxyfen;

G) Lipid and membrane synthesis inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acids: propamocarb, propamocarb-hydrochlorid;
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;

H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatineacetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)tetraone;

I) Cell wall synthesis inhibitors
inhibitors of glucan synthesis: validamycin, polyoxin B;
melanin synthesis inhibitors: pyroquilon, tricyclazole, carpropamid, dicyclomet, fenoxanil;

J) Plant defence inducers
acibenzolar-S-methyl, probenazole, isotianil, tiadinil, prohexadione-calcium; phosphonates: fosetyl, fosetyl-aluminum, phosphorous acid and its salts;

K) Unknown mode of action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl form amidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazol-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazol-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxyacetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxyacetamide;

L) Antifungal biocontrol agents, plant bioactivators: *Ampelomyces quisqualie* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amylolique-faciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. Endothia parasitica from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER®

WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. vinde* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chlorophenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1 H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound I or VIII, respectively, (component 1) and at least one further active substance useful for plant protection, e.g. selected from the groups A) to O) (component 2), in particular one further fungicide, e.g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I or VIII, respectively, and at least one fungicide from groups A) to L), as described above, is more efficient than combating those fungi with individual compounds I or VIII, respectively, or individual fungicides from groups A) to L). By applying compounds I or VIII, respectively, together with at least one active substance from groups A) to O) a synergistic effect can be obtained, i.e. more then simple addition of the individual effects is obtained (synergistic mixtures).

This can be obtained by applying the compounds I or VIII, respectively, and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I or VIII, respectively, (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I or VIII, respectively, (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I or VIII, respectively, (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I or VIII, respectively, (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I or VIII, respectively, (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I or VIII, respectively, (component 1) and at least one active substance selected from group E) (component 2) and particularly selected from cyprodinil, mepanipyrim, pyrimethanil.

Preference is also given to mixtures comprising a compound I or VIII, respectively, (component 1) and at least one active substance selected from group F) (component 2) and particularly selected from iprodione, fludioxonil, vinclozolin, quinoxyfen.

Preference is also given to mixtures comprising a compound I or VIII, respectively, (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I or VIII, respectively, (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I or VIII, respectively, (component 1) and at least one active substance selected from group I) (component 2) and particularly selected from carpropamid and fenoxanil.

Preference is also given to mixtures comprising a compound I or VIII, respectively, (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to mixtures comprising a compound I or VIII, respectively, (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide.

Preference is also given to mixtures comprising a compound I or VIII, respectively, (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I or VIII, respectively, (component 1) and one further active substance (component 2), which further active substance is selected from the column "Component 2" of the lines B-1 to B-372 of Table B.

A further embodiment relates to the compositions B-1 to B-372 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
|---|---|---|
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |
| B-30 | one individualized compound I | Fluxapyroxad |
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |
| B-45 | one individualized compound I | Thifluzamide |

TABLE B-continued

Composition comprising one indiviualized compound I and one further active substance from groups A) to O)

| Mixture | Component 1 | Component 2 |
|---|---|---|
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | Dimethomorph |
| B-52 | one individualized compound I | Flumorph |
| B-53 | one individualized compound I | Pyrimorph |
| B-54 | one individualized compound I | Flumetover |
| B-55 | one individualized compound I | Fluopicolide |
| B-56 | one individualized compound I | Fluopyram |
| B-57 | one individualized compound I | Zoxamide |
| B-58 | one individualized compound I | Carpropamid |
| B-59 | one individualized compound I | Diclocymet |
| B-60 | one individualized compound I | Mandipropamid |
| B-61 | one individualized compound I | Oxytetracyclin |
| B-62 | one individualized compound I | Silthiofam |
| B-63 | one individualized compound I | N-(6-methoxy-pyridin-3-yl) cyclopropanecarboxylic acid amide |
| B-64 | one individualized compound I | Azaconazole |
| B-65 | one individualized compound I | Bitertanol |
| B-66 | one individualized compound I | Bromuconazole |
| B-67 | one individualized compound I | Cyproconazole |
| B-68 | one individualized compound I | Difenoconazole |
| B-69 | one individualized compound I | Diniconazole |
| B-70 | one individualized compound I | Diniconazole-M |
| B-71 | one individualized compound I | Epoxiconazole |
| B-72 | one individualized compound I | Fenbuconazole |
| B-73 | one individualized compound I | Fluquinconazole |
| B-74 | one individualized compound I | Flusilazole |
| B-75 | one individualized compound I | Flutriafol |
| B-76 | one individualized compound I | Hexaconazol |
| B-77 | one individualized compound I | Imibenconazole |
| B-78 | one individualized compound I | Ipconazole |
| B-79 | one individualized compound I | Metconazole |
| B-80 | one individualized compound I | Myclobutanil |
| B-81 | one individualized compound I | Oxpoconazol |
| B-82 | one individualized compound I | Paclobutrazol |
| B-83 | one individualized compound I | Penconazole |
| B-84 | one individualized compound I | Propiconazole |
| B-85 | one individualized compound I | Prothioconazole |
| B-86 | one individualized compound I | Simeconazole |
| B-87 | one individualized compound I | Tebuconazole |
| B-88 | one individualized compound I | Tetraconazole |
| B-89 | one individualized compound I | Triadimefon |
| B-90 | one individualized compound I | Triadimenol |
| B-91 | one individualized compound I | Triticonazole |
| B-92 | one individualized compound I | Uniconazole |
| B-93 | one individualized compound I | Cyazofamid |
| B-94 | one individualized compound I | Imazalil |
| B-95 | one individualized compound I | Imazalil-sulfate |
| B-96 | one individualized compound I | Pefurazoate |
| B-97 | one individualized compound I | Prochloraz |
| B-98 | one individualized compound I | Triflumizole |
| B-99 | one individualized compound I | Benomyl |
| B-100 | one individualized compound I | Carbendazim |
| B-101 | one individualized compound I | Fuberidazole |
| B-102 | one individualized compound I | Thiabendazole |
| B-103 | one individualized compound I | Ethaboxam |
| B-104 | one individualized compound I | Etridiazole |
| B-105 | one individualized compound I | Hymexazole |
| B-106 | one individualized compound I | 2-(4-Chloro-phenyl)-N-[4-(3,4-dimethoxy-phenyl)-isoxazol-5-yl]-2-prop-2-yn-yloxy-acetamide |
| B-107 | one individualized compound I | Fluazinam |
| B-108 | one individualized compound I | Pyrifenox |

TABLE B-continued

Composition comprising one indiviualized compound I and one further active substance from groups A) to O)

| Mixture | Component 1 | Component 2 |
|---|---|---|
| B-109 | one individualized compound I | 3-[5-(4-Chloro-phenyl)-2,3-dimethyl-isoxazolidin-3-yl]-pyridine (Pyrisoxazole) |
| B-110 | one individualized compound I | 3-[5-(4-Methyl-phenyl)-2,3-dimethyl-isoxazolidin-3-yl]-pyridine |
| B-111 | one individualized compound I | Bupirimate |
| B-112 | one individualized compound I | Cyprodinil |
| B-113 | one individualized compound I | 5-Fluorocytosine |
| B-114 | one individualized compound I | 5-Fluoro-2-(p-tolylmethoxy)pyrimidin-4-amine |
| B-115 | one individualized compound I | 5-Fluoro-2-(4-fluorophenylmethoxy)-pyrimidin-4-amine |
| B-116 | one individualized compound I | Diflumetorim |
| B-117 | one individualized compound I | (5,8-Difluoroquinazolin-4-yl)-{2-[2-fluoro-4-(4-trifluoromethylpyridin-2-yloxy)-phenyl]-ethyl}-amine |
| B-118 | one individualized compound I | Fenarimol |
| B-119 | one individualized compound I | Ferimzone |
| B-120 | one individualized compound I | Mepanipyrim |
| B-121 | one individualized compound I | Nitrapyrin |
| B-122 | one individualized compound I | Nuarimol |
| B-123 | one individualized compound I | Pyrimethanil |
| B-124 | one individualized compound I | Triforine |
| B-125 | one individualized compound I | Fenpiclonil |
| B-126 | one individualized compound I | Fludioxonil |
| B-127 | one individualized compound I | Aldimorph |
| B-128 | one individualized compound I | Dodemorph |
| B-129 | one individualized compound I | Dodemorph-acetate |
| B-130 | one individualized compound I | Fenpropimorph |
| B-131 | one individualized compound I | Tridemorph |
| B-132 | one individualized compound I | Fenpropidin |
| B-133 | one individualized compound I | Fluoroimid |
| B-134 | one individualized compound I | Iprodione |
| B-135 | one individualized compound I | Procymidone |
| B-136 | one individualized compound I | Vinclozolin |
| B-137 | one individualized compound I | Famoxadone |
| B-138 | one individualized compound I | Fenamidone |
| B-139 | one individualized compound I | Flutianil |
| B-140 | one individualized compound I | Octhilinone |
| B-141 | one individualized compound I | Probenazole |
| B-142 | one individualized compound I | Fenpyrazamine |
| B-143 | one individualized compound I | Acibenzolar-S-methyl |
| B-144 | one individualized compound I | Ametoctradin |
| B-145 | one individualized compound I | Amisulbrom |
| B-146 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| B-147 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| B-148 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| B-149 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |
| B-150 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methyl-propanoate |
| B-151 | one individualized compound I | Anilazin |
| B-152 | one individualized compound I | Blasticidin-S |
| B-153 | one individualized compound I | Captafol |
| B-154 | one individualized compound I | Captan |
| B-155 | one individualized compound I | Chinomethionat |
| B-156 | one individualized compound I | Dazomet |
| B-157 | one individualized compound I | Debacarb |
| B-158 | one individualized compound I | Diclomezine |
| B-159 | one individualized compound I | Difenzoquat, |
| B-160 | one individualized compound I | Difenzoquat-methylsulfate |
| B-161 | one individualized compound I | Fenoxanil |

TABLE B-continued

Composition comprising one indiviualized compound I and one further active substance from groups A) to O)

| Mixture | Component 1 | Component 2 |
|---|---|---|
| B-162 | one individualized compound I | Folpet |
| B-163 | one individualized compound I | Oxolinsaure |
| B-164 | one individualized compound I | Piperalin |
| B-165 | one individualized compound I | Proquinazid |
| B-166 | one individualized compound I | Pyroquilon |
| B-167 | one individualized compound I | Quinoxyfen |
| B-168 | one individualized compound I | Triazoxid |
| B-169 | one individualized compound I | Tricyclazole |
| B-170 | one individualized compound I | 2-Butoxy-6-iodo-3-propyl-chromen-4-one |
| B-171 | one individualized compound I | 5-Chloro-1-(4,6-dimethoxy-pyrimidin-2-yl)-2-methyl-1H-benzoimidazole |
| B-172 | one individualized compound I | 5-Chloro-7-(4-methyl-piperidin-1-yl)-6-(2,4,6-trifluoro-phenyl)-[1,2,4]triazolo[1,5-a]pyrimidine |
| B-173 | one individualized compound I | Ferbam |
| B-174 | one individualized compound I | Mancozeb |
| B-175 | one individualized compound I | Maneb |
| B-176 | one individualized compound I | Metam |
| B-177 | one individualized compound I | Methasulphocarb |
| B-178 | one individualized compound I | Metiram |
| B-179 | one individualized compound I | Propineb |
| B-180 | one individualized compound I | Thiram |
| B-181 | one individualized compound I | Zineb |
| B-182 | one individualized compound I | Ziram |
| B-183 | one individualized compound I | Diethofencarb |
| B-184 | one individualized compound I | Benthiavalicarb |
| B-185 | one individualized compound I | Iprovalicarb |
| B-186 | one individualized compound I | Propamocarb |
| B-187 | one individualized compound I | Propamocarb hydrochlorid |
| B-188 | one individualized compound I | Valifenalate |
| B-189 | one individualized compound I | N-(1-(1-(4-cyanophenyl)ethanesulfonyl)-but-2-yl) carbamic acid-(4-fluoro-phenyl) ester |
| B-190 | one individualized compound I | Dodine |
| B-191 | one individualized compound I | Dodine free base |
| B-192 | one individualized compound I | Guazatine |
| B-193 | one individualized compound I | Guazatine-acetate |
| B-194 | one individualized compound I | Iminoctadine |
| B-195 | one individualized compound I | Iminoctadine-triacetate |
| B-196 | one individualized compound I | Iminoctadine-tris(albesilate) |
| B-197 | one individualized compound I | Kasugamycin |
| B-198 | one individualized compound I | Kasugamycin-hydrochloride-hydrate |
| B-199 | one individualized compound I | Polyoxine |
| B-200 | one individualized compound I | Streptomycin |
| B-201 | one individualized compound I | Validamycin A |
| B-202 | one individualized compound I | Binapacryl |
| B-203 | one individualized compound I | Dicloran |
| B-204 | one individualized compound I | Dinobuton |
| B-205 | one individualized compound I | Dinocap |
| B-206 | one individualized compound I | Nitrothal-isopropyl |
| B-207 | one individualized compound I | Tecnazen |
| B-208 | one individualized compound I | Fentin salts |
| B-209 | one individualized compound I | Dithianon |
| B-210 | one individualized compound I | Isoprothiolane |
| B-211 | one individualized compound I | Edifenphos |
| B-212 | one individualized compound I | Fosetyl, Fosetyl-aluminium |
| B-213 | one individualized compound I | Iprobenfos |
| B-214 | one individualized compound I | Phosphorous acid ($H_3PO_3$) and derivatives |
| B-215 | one individualized compound I | Pyrazophos |
| B-216 | one individualized compound I | Tolclofos-methyl |
| B-217 | one individualized compound I | Chlorothalonil |
| B-218 | one individualized compound I | Dichlofluanid |
| B-219 | one individualized compound I | Dichlorophen |
| B-220 | one individualized compound I | Flusulfamide |
| B-221 | one individualized compound I | Hexachlorbenzene |
| B-222 | one individualized compound I | Pencycuron |
| B-223 | one individualized compound I | Pentachlorophenol and salts |
| B-224 | one individualized compound I | Phthalide |
| B-225 | one individualized compound I | Quintozene |
| B-226 | one individualized compound I | Thiophanate Methyl |
| B-227 | one individualized compound I | Tolylfluanid |
| B-228 | one individualized compound I | N-(4-chloro-2-nitro-phenyl)-N-ethyl-4-methyl-benzenesulfonamide |
| B-229 | one individualized compound I | Bordeaux mixture |

TABLE B-continued

Composition comprising one indiviualized compound I and one further active substance from groups A) to O)

| Mixture | Component 1 | Component 2 |
|---|---|---|
| B-230 | one individualized compound I | Copper acetate |
| B-231 | one individualized compound I | Copper hydroxide |
| B-232 | one individualized compound I | Copper oxychloride |
| B-233 | one individualized compound I | basic Copper sulfate |
| B-234 | one individualized compound I | Sulfur |
| B-235 | one individualized compound I | Biphenyl |
| B-236 | one individualized compound I | Bronopol |
| B-237 | one individualized compound I | Cyflufenamid |
| B-238 | one individualized compound I | Cymoxanil |
| B-239 | one individualized compound I | Diphenylamin |
| B-240 | one individualized compound I | Metrafenone |
| B-241 | one individualized compound I | Pyriofenone |
| B-242 | one individualized compound I | Mildiomycin |
| B-243 | one individualized compound I | Oxin-copper |
| B-244 | one individualized compound I | Prohexadione calcium |
| B-245 | one individualized compound I | Spiroxamine |
| B-246 | one individualized compound I | Tebufloquin |
| B-247 | one individualized compound I | Tolylfluanid |
| B-248 | one individualized compound I | N-(Cyclopropylmethoxyimino-(6-difluoromethoxy-2,3-difluoro-phenyl)-methyl)-2-phenyl acetamide |
| B-249 | one individualized compound I | N'-(4-(4-chloro-3-trifluoromethyl-phenoxy)-2,5-dimethyl-phenyl)-N-ethyl-N-methyl formamidine |
| B-250 | one individualized compound I | N'-(4-(4-fluoro-3-trifluoromethyl-phenoxy)-2,5-dimethyl-phenyl)-N-ethyl-N-methyl formamidine |
| B-251 | one individualized compound I | N'-(2-methyl-5-trifluoromethyl-4-(3-tri-methylsilanyl-propoxy)-phenyl)-N-ethyl-N-methyl formamidine |
| B-252 | one individualized compound I | N'-(5-difluoromethyl-2-methyl-4-(3-tri-methylsilanyl-propoxy)-phenyl)-N-ethyl-N-methyl formamidine |
| B-253 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-254 | one individualized compound I | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-255 | one individualized compound I | 1-[4-[4-[5-(2,6-difluorophenyl)-4,5-di-hydro-3-isoxazolyl]-2-thiazolyl]-1-piperidinyl]-2-[5-methyl-3-(trifluoro-methyl)-1H-pyrazol-1-yl]ethanone |
| B-256 | one individualized compound I | Methoxy-acetic acid 6-tert-butyl-8-fluoro-2,3-dimethyl-quinolin-4-yl ester |
| B-257 | one individualized compound I | N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thiazolecarboxamide |
| B-258 | one individualized compound I | *Bacillus subtilis* NRRL No. B-21661 |
| B-259 | one individualized compound I | *Bacillus pumilus* NRRL No. B-30087 |
| B-260 | one individualized compound I | *Ulocladium oudemansii* |
| B-261 | one individualized compound I | Carbaryl |
| B-262 | one individualized compound I | Carbofuran |
| B-263 | one individualized compound I | Carbosulfan |
| B-264 | one individualized compound I | Methomylthiodicarb |
| B-265 | one individualized compound I | Bifenthrin |
| B-266 | one individualized compound I | Cyfluthrin |
| B-267 | one individualized compound I | Cypermethrin |
| B-268 | one individualized compound I | alpha-Cypermethrin |
| B-269 | one individualized compound I | zeta-Cypermethrin |
| B-270 | one individualized compound I | Deltamethrin |
| B-271 | one individualized compound I | Esfenvalerate |
| B-272 | one individualized compound I | Lambda-cyhalothrin |
| B-273 | one individualized compound I | Permethrin |
| B-274 | one individualized compound I | Tefluthrin |
| B-275 | one individualized compound I | Diflubenzuron |
| B-276 | one individualized compound I | Flufenoxuron |
| B-277 | one individualized compound I | Lufenuron |
| B-278 | one individualized compound I | Teflubenzuron |
| B-279 | one individualized compound I | Spirotetramate |

TABLE B-continued

Composition comprising one indiviualized compound I and one further active substance from groups A) to O)

| Mixture | Component 1 | Component 2 |
|---|---|---|
| B-280 | one individualized compound I | Clothianidin |
| B-281 | one individualized compound I | Dinotefuran |
| B-282 | one individualized compound I | Imidacloprid |
| B-283 | one individualized compound I | Thiamethoxam |
| B-284 | one individualized compound I | Flupyradifurone |
| B-285 | one individualized compound I | Acetamiprid |
| B-286 | one individualized compound I | Thiacloprid |
| B-287 | one individualized compound I | Endosulfan |
| B-288 | one individualized compound I | Fipronil |
| B-289 | one individualized compound I | Abamectin |
| B-290 | one individualized compound I | Emamectin |
| B-291 | one individualized compound I | Spinosad |
| B-292 | one individualized compound I | Spinetoram |
| B-293 | one individualized compound I | Hydramethylnon |
| B-294 | one individualized compound I | Chlorfenapyr |
| B-295 | one individualized compound I | Fenbutatin oxide |
| B-296 | one individualized compound I | Indoxacarb |
| B-297 | one individualized compound I | Metaflumizone |
| B-298 | one individualized compound I | Flonicamid |
| B-299 | one individualized compound I | Lubendiamide |
| B-300 | one individualized compound I | Chlorantraniliprole |
| B-301 | one individualized compound I | Cyazypyr (HGW86) |
| B-302 | one individualized compound I | Cyflumetofen |
| B-303 | one individualized compound I | Acetochlor |
| B-304 | one individualized compound I | Dimethenamid |
| B-305 | one individualized compound I | metolachlor |
| B-306 | one individualized compound I | Metazachlor |
| B-307 | one individualized compound I | Glyphosate |
| B-308 | one individualized compound I | Glufosinate |
| B-309 | one individualized compound I | Sulfosate |
| B-310 | one individualized compound I | Clodinafop |
| B-311 | one individualized compound I | Fenoxaprop |
| B-312 | one individualized compound I | Fluazifop |
| B-313 | one individualized compound I | Haloxyfop |
| B-314 | one individualized compound I | Paraquat |
| B-315 | one individualized compound I | Phenmedipham |
| B-316 | one individualized compound I | Clethodim |
| B-317 | one individualized compound I | Cycloxydim |
| B-318 | one individualized compound I | Profoxydim |
| B-319 | one individualized compound I | Sethoxydim |
| B-320 | one individualized compound I | Tepraloxydim |
| B-321 | one individualized compound I | Pendimethalin |
| B-322 | one individualized compound I | Prodiamine |
| B-323 | one individualized compound I | Trifluralin |
| B-324 | one individualized compound I | Acifluorfen |
| B-325 | one individualized compound I | Bromoxynil |
| B-326 | one individualized compound I | Imazamethabenz |
| B-327 | one individualized compound I | Imazamox |
| B-328 | one individualized compound I | Imazapic |
| B-329 | one individualized compound I | Imazapyr |
| B-330 | one individualized compound I | Imazaquin |
| B-331 | one individualized compound I | Imazethapyr |
| B-332 | one individualized compound I | 2,4-Dichlorophenoxyacetic acid (2,4-D) |
| B-333 | one individualized compound I | Chloridazon |
| B-334 | one individualized compound I | Clopyralid |
| B-335 | one individualized compound I | Fluroxypyr |
| B-336 | one individualized compound I | Picloram |
| B-337 | one individualized compound I | Picolinafen |
| B-338 | one individualized compound I | Bensulfuron |
| B-339 | one individualized compound I | Chlorimuron-ethyl |
| B-340 | one individualized compound I | Cyclosulfamuron |
| B-341 | one individualized compound I | Iodosulfuron |
| B-342 | one individualized compound I | Mesosulfuron |
| B-343 | one individualized compound I | Metsulfuron-methyl |
| B-344 | one individualized compound I | Nicosulfuron |
| B-345 | one individualized compound I | Rimsulfuron |
| B-346 | one individualized compound I | Triflusulfuron |
| B-347 | one individualized compound I | Atrazine |
| B-348 | one individualized compound I | Hexazinone |
| B-349 | one individualized compound I | Diuron |
| B-350 | one individualized compound I | Florasulam |
| B-351 | one individualized compound I | Pyroxasulfone |
| B-352 | one individualized compound I | Bentazone |
| B-353 | one individualized compound I | Cinidon-ethyl |
| B-354 | one individualized compound I | Cinmethylin |

TABLE B-continued

Composition comprising one indiviualized compound I and one further active substance from groups A) to O)

| Mixture | Component 1 | Component 2 |
|---|---|---|
| B-355 | one individualized compound I | Dicamba |
| B-356 | one individualized compound I | Diflufenzopyr |
| B-357 | one individualized compound I | Quinclorac |
| B-358 | one individualized compound I | Quinmerac |
| B-359 | one individualized compound I | Mesotrione |
| B-360 | one individualized compound I | Saflufenacil |
| B-361 | one individualized compound I | Topramezone |
| B-362 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-363 | one individualized compound I | [rel-(2S;3R)-3-(2-chlorophenyl)-2-(2,4-difluorophenyl)-oxiranylmethyl]-5-thiocyanato-1H-[1,2,4]triazole, |
| B-364 | one individualized compound I | 2-[rel-(2S;3R)-3-(2-chlorophenyl)-2-(2,4-difluorophenyl)-oxiranylmethyl]-2H-[1,2,4]triazole-3-thiol |
| B-365 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone |
| B-366 | one individualized compound I | 2,6-dimethyl-1H,5H-[1,4]dithiino[2,3-c:5,6-c']dipyrrole-1,3,5,7(2H,6H)-tetraone |
| B-367 | one individualized compound I | 3-(difluoromethyl)-1-methyl-N-(1,1,3-trimethylindan-4-yl)pyrazole-4-carboxamide |
| B-368 | one individualized compound I | 3-(trifluoromethyl)-1-methyl-N-(1,1,3-trimethylindan-4-yl)pyrazole-4-carboxamide |
| B-369 | one individualized compound I | 1,3-dimethyl-N-(1,1,3-trimethylindan-4-yl)pyrazole-4-carboxamide |
| B-370 | one individualized compound I | 3-(trifluorometh-yl)-1,5-dimethyl-N-(1,1,3-trimethylindan-4-yl)pyrazole-4-carboxamide |
| B-371 | one individualized compound I | 3-(difluoro-methyl)-1,5-dimethyl-N-(1,1,3-trimethylindan-4-yl)pyrazole-4-carboxamide |
| B-372 | one individualized compound I | 1,3,5-tri-methyl-N-(1,1,3-trimethylindan-4-yl)pyrazole-4-carboxamide |

A further embodiment relates to the compositions B2-1 to B2-372 listed in Table B2, where a row of Table B2 corresponds in each case to a fungicidal composition comprising one of the in the present specification individualized compounds of formula VIII (component 1) and the respective further active substance from groups A) to O) (component 2) stated in the row in question. Preferably, the compositions described comprise the active substances in synergistically effective amounts.

Table B2:

Composition comprising one individualized compound VIII and one further active substance from groups A) to O). This table corresponds to table B, wherein in the first column the number/name of the individualized mixture is named "B2- . . . " instead of "B- . . . " and in the second column, it says in each line "one individualized compound VIII" instead of "one individualized compound I".

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657).

The mixtures of active substances can be prepared as compositions comprising besides the active ingredients at least one inert ingredient by usual means, e.g. by the means given for the compositions of compounds I and VIII, respectively.

Concerning usual ingredients of such compositions reference is made to the explanations given for the compositions containing compounds I and VIII, respectively.

The mixtures of active substances according to the present invention are suitable as fungicides, as are the compounds of formula I and VIII, respectively. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I and VIII, respectively, respectively.

I. SYNTHESIS EXAMPLES

With due modification of the starting compounds, the procedures shown in the synthesis examples below were used to obtain further compounds I. The resulting compounds, together with physical data, are listed in Table I below.

Example 1

Synthesis of 1-[2-benzyloxy-2-[2-chloro-4-(4-chlorophenoxy)phenyl]propyl]-1,2,4-triazole (compound 1-1)

Step 1:
1-[2-chloro-4-(4-chlorophenoxy)phenyl]ethanone

A mixture of 4-chlorophenol (186 g), 2-chloro-4-fluoroacetophenone (250 g) and potassium carbonate (238 g) in DMF (960 mL) was heated to reflux for 48 h. After cooling to room temperature, the reaction mixture was partitioned between MTBE and water and the aqueous phase was extracted twice with MTBE. The combined organic phases were consecutively washed with 10% LiCl solution, dil. NaOH solution and water and dried. The solvent was evaporated under reduced pressure and the crude material was crystallized from diisopropyl ether.

Step 2: 2-[2-chloro-4-(4-chlorophenoxy)phenyl]-2-methyloxirane

DMSO (150 mL) was added dropwise to a mixture of sodium hydride (22 g) in THF (600 mL). After completion of the addition a solution of trimethylsulfonium iodide (171 g) in DMSO (300 mL) was added slowly at 5° C. whereupon a solution of 1-[2-chloro-4-(4-chlorophenoxy)phenyl]ethanone (107 g) in DMSO (300 mL) was added carefully. The mixture was stirred for 1 h at room temperature and dil. NH4Cl solution was added. The mixture was extracted with MTBE (3×) and the combined organic phases were washed with water, dried and evaporated to obtain the desired compound that was used without further purification.

Step 3: 2-[2-chloro-4-(4-chlorophenoxy)phenyl]-1-(1,2,4-triazol-1-yl)propan-2-ol A mixture of 2-[2-chloro-4-(4-chlorophenoxy)phenyl]-2-methyloxirane (109 g), 1,2,4-triazole (27 g) and sodium hydroxide (16 g) in NMP (1 L) was heated to 110° C. for 1 h. The reaction mixture was then partitioned between MTBE and aq. NaHCO$_3$ solution and the aq. phase was extracted twice with MTBE. The combined organic phases were washed with water (2×), dried and evaporated. The crude product was crystallized from diisopropyl ether.

Step 4: 1-[2-benzyloxy-2-[2-chloro-4-(4-chlorophenoxy)phenyl]propyl]-1,2,4-triazole Sodium hydride (0.04 g) was added to a solution of 2-[2-chloro-4-(4-chlorophenoxy)phenyl]-1-(1,2,4-triazol-1-yl)propan-2-ol (0.5 g) in THF (15 mL). After 30 min benzylbromide (0.27 g) was added and the mixture was stirred for 18 h at reflux. Brine was added and the mixture was extracted with dichloro methane (3×). The combined organic phases were dried, filtered through a silica plug and evaporated. The crude product was purified by column chromatography to yield 0.43 g of the desired compound.

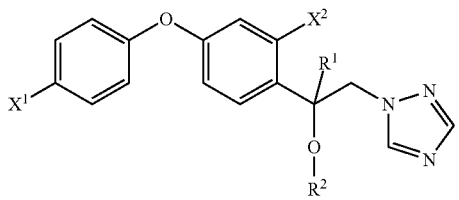

The compounds I listed in Table I have been prepared in an analogous manner.

TABLE I

| ex.-no. | $X^1$ | $X^2$ | $R^1$ | $R^2$ | HPLC* $R_t$ (min) |
|---|---|---|---|---|---|
| I-1 | Cl | Cl | CH$_3$ | CH$_2$C$_6$H$_5$ | 1.40 |
| I-2 | Cl | Cl | C$_2$H$_5$ | CH$_2$C$_6$H$_5$ | 1.45 |
| I-3 | Cl | Cl | cyclopropyl | CH$_2$C$_6$H$_5$ | 1.45 |
| I-4 | Cl | Cl | CH$_3$ | CH$_2$C$_3$H$_5$ | 1.37 |
| I-5 | Cl | Cl | C$_2$H$_5$ | CH$_2$C$_3$H$_5$ | 1.41 |
| I-6 | Cl | Cl | cyclopropyl | CH$_2$C$_3$H$_5$ | 1.42 |
| I-7 | Cl | Cl | C≡CH | CH$_2$C$_6$H$_5$ | 1.38 |
| I-8 | Cl | Cl | CHFC$_2$H$_5$ | CH$_2$C$_6$H$_5$ | 1.49 |

*HPLC methode Data: Mobile Phase: A: Water + 0.1% TFA, B: acetonitrile; Gradient: 5% B to 100% B in 1.5 min; Temperature: 60° C.; MS method; ESI positive; mass area (m/z): 10-700; Flow; 0.8 ml/min to 1.0 ml/min in 1.5 min; Column: Kinetex XB C18 1.7μ 50 × 2.1 mm; Aparatus: Shimadzu Nexera LC-30 LCMS-2020

II. EXAMPLES OF THE ACTION AGAINST HARMFUL FUNGI

A) Green House

The spray solutions were prepared in several steps:
The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

G1. Preventative Control of Brown Rust on Wheat Caused by *Puccinia recondita* (Puccrt P1)

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area. In this test, the plants which had been treated with 300 ppm of the active substance from examples I-1, I-4, I-5 and I-6, respectively, showed an infection of less than or equal to 10% whereas the untreated plants were 80% infected.

G2. Preventative Fungicidal Control of Early Blight on Tomatoes (*Alternaria solani*) (Alteso P1)

Young seedlings of tomato plants were grown in pots. These plants were sprayed to run-off with an aqueous suspension, containing the concentration of active ingredient or mixture mentioned in the table below. The next day, the treated plants were inoculated with an aqueous suspension of *Alternaria solani*. Then the trial plants were immediately transferred to a humid chamber. After 5 days at 18 to 20° C. and a relative humidity close to 100%, the extent of fungal attack on the leaves was visually assessed as % diseased leaf area. In this test, the plants which had been treated with 300 ppm of the active substance from examples I-1, I-4, I-5 and I-6, respectively, showed an infection of less than or equal to 10% whereas the untreated plants were 90% infected.

G3. Preventative Control of Leaf Blotch on Wheat Caused by *Septoria tritici* (Septtr P7)

Leaves of pot-grown wheat seedling were sprayed to run-off with an aqueous suspension of the active compound or their mixture, prepared as described. The plants were allowed to air-dry. Seven days later the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

G4. Protective Control of Soy Bean Rust on Soy Beans Caused by *Phakopsora pachyrhizi* (Phakpa P2)

Leaves of pot-grown soy bean seedlings were sprayed to run-off with an aqueous suspension, containing the concentration of active ingredient or their mixture as described below. The plants were allowed to air-dry. The trial plants were cultivated for 2 days in a greenhouse chamber at 23-27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24° C. for 24 h. The trial plants were cultivated for fourteen days in a greenhouse chamber at 23-27° C. and a relative humidity between 60 and 80%. The extent of fungal attack on the leaves was visually assessed as % diseased leaf area.

B) Microtest

The active compounds were formulated separately as a stock solution having a concentration of 10000 ppm in dimethyl sulfoxide.

M1. Activity Against Wheat Leaf Spots Caused by *Leptosphaeria nodorum* (Leptno)

The stock solutions were mixed according to the ratio, pipetted onto a micro titer plate (MTP) and diluted with water to the stated concentrations. A spore suspension of *Leptosphaeria nodorum* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. Compounds I-1, I-2, I-3, I-4, I-5 and I-6 showed a growth of 8% or less at 32 ppm.

M2. Activity Against Leaf Blotch on Wheat Caused by *Septoria tritici*(Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. Compounds I-1, I-2, I-3, I-4, I-5 and I-6 showed a growth of 14% or less at 32 ppm.

Comparison

| Structure | Disease (%) at 16 ppm Septtr P7 | Growth (%) at 0.00012 ppm Septtr | Disease (%) at 63 ppm Phakpa P2 |
|---|---|---|---|
| prior art compound 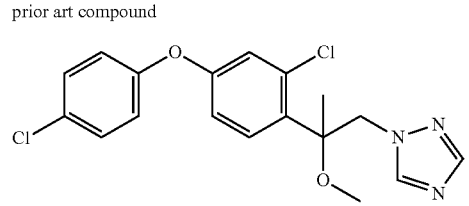 [SMILES: COC(C)(Cn1cncn1)c1ccc(Oc2ccc(Cl)cc2)cc1Cl] | 80 | 63 | |
| inventive compound I-1, table I | | 23 | |
| inventive compound I-4, table I | 60 | | |
| prior art compound 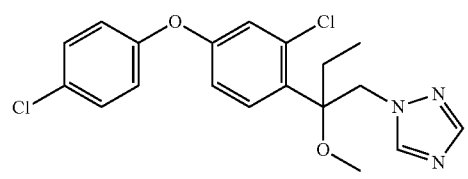 | | | 60 |
| inventive compound I-2, table I | | | 20 |
| inventive compound I-5, table I | | | 3 |
| Untreated control | 90 | — | 90 |

The invention claimed is:

1. A compound of formula I

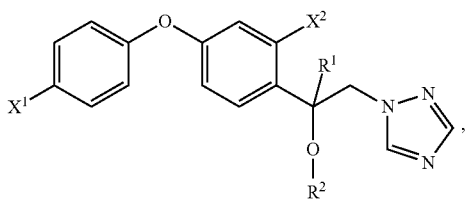

wherein:

$X^1$, $X^2$ independently of each other are selected from halogen;

$R^1$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;

$R^2$ is $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;

wherein the aliphatic moieties of $R^1$ and/or $R^2$ may carry 1, 2, 3 or up to the maximum possible number of identical or different groups $R^a$ which independently of one another are selected from the group consisting of halogen, CN, nitro, $C_1$-$C_4$-alkoxy and $C_1$-$C_4$-halogenalkoxy;

wherein the cycloalkyl and/or phenyl moieties of $R^1$ and/or $R^2$ may carry 1, 2, 3, 4, 5 or up to the maximum number of identical or different groups $R^b$ which independently of one another are selected from:

$R^b$ is selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy;

or an N-oxide or an agriculturally acceptable salt thereof.

2. The compound of claim 1, wherein $X^1$ is Cl.

3. The compound of claim 1, wherein $X^2$ is Cl.

4. The compound of claim 1, wherein $R^1$ is $C_1$-$C_4$-alkyl.

5. The compound of claim 1, wherein $R^1$ is unsubstituted.

6. The compound of claim 1, wherein $R^2$ is $C_3$-$C_8$-cycloalkyl-$C_1$-$C_4$-alkyl or phenyl-$C_1$-$C_4$-alkyl, that are unsubstituted or substituted by $R^a$ and/or $R^b$.

7. The compound of claim 1, wherein $R^2$ is unsubstituted.

8. The compound of claim 1, wherein $X^1$ and $X^2$ are Cl, $R^2$ is $CH_2C_6H_5$ and $R^1$ is $CH_3$, $C_2H_5$, cyclopropyl, C≡CH or $CHFC_2H_5$, and compounds, wherein $X^1$ and $X^2$ are Cl, $R^2$ is $CH_2C_3H_5$ and $R^1$ is $CH_3$, $C_2H_5$ or cyclopropyl.

9. A process for preparing the compound of claim 1, comprising reacting a compound of formula IIIa

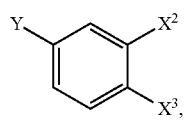

wherein Y is F or Cl and $X^3$ is I or Br, with a halo-phenole of formula II

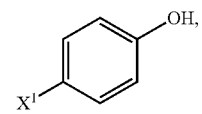

under basic conditions;

reacting the resulting compound of formula IVa

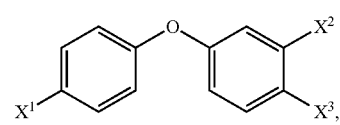

with isopropylmagnesium bromide followed by a reaction with acetyl chloride;

halogenating the resulting compound of formula V

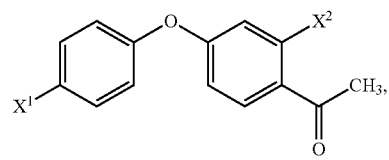

reacting the resulting compound of formula VI

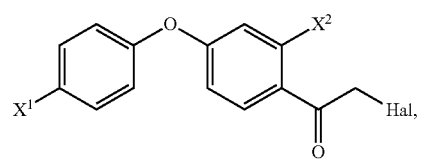

wherein Hal stands for halogen, under basic conditions with 1H-1,2,4-triazole;

reacting the resulting compound of formula VII

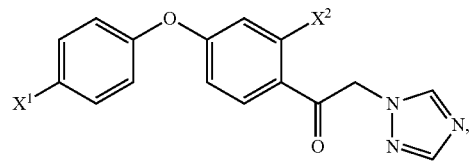

with $R^1$-M, wherein M is MgBr, MgCl, Li or Na, and reacting the resulting compound of VIII

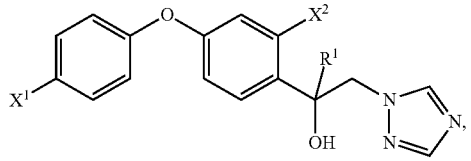

under basic conditions with $R^2$-LG, wherein LG is a nucleophilically replaceable leaving group, to obtain the compound of formula I.

10. A process for preparing the compound of claim 1, comprising reacting a compound of formula IIIa

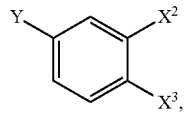

wherein Y is F or Cl and $X^3$ is I or Br, with isopropylmagnesium halide followed by a reaction with a compound of formula IX $R^1$—COCl,
converting the resulting compound of formula X

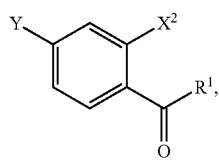

wherein Y is F or Cl;
under basic conditions with a halo-phenole of formula II

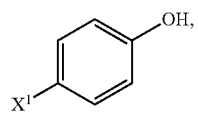

reacting the resulting compound of formula Va

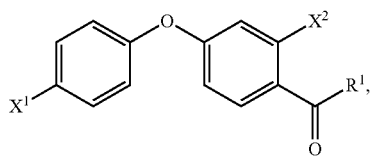

with trimethylsulf(ox)onium halide;
reacting the resulting compound of formula XI

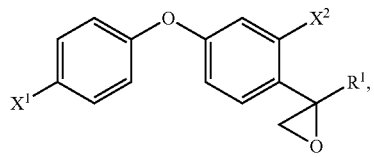

under basic conditions with 1H-1,2,4-triazole;
and reacting the resulting compound of formula VIII

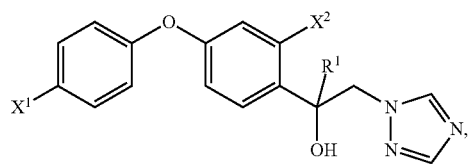

under basic conditions with $R^2$-LG, wherein LG is a nucleophilically replaceable leaving group, to obtain the compound of formula I.

11. A process for preparing the compound of claim 1, comprising reacting a compound of formula XI

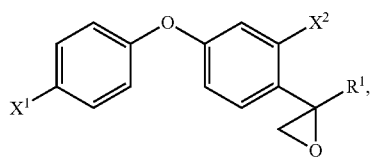

under acidic conditions with $R^2$—OH;
reacting the resulting compound of formula XII

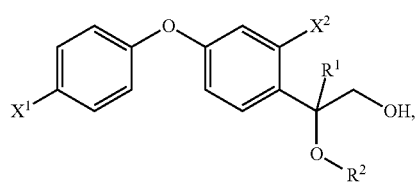

with a halogenating agent or sulfonating agent;
and reacting the resulting compound of formula XIII

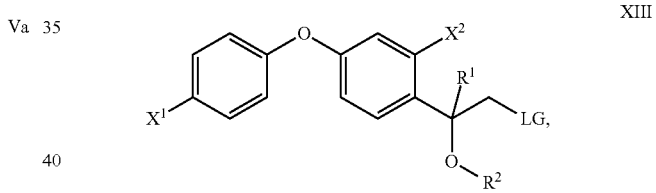

wherein LG is a nucleophilically replaceable leaving group with 1H-1,2,4-triazole, to obtain compounds I.

12. An agrochemical composition comprising an auxiliary and at least one compound of claim 1, an N-oxide or an agriculturally acceptable salt thereof.

13. A seed coated with at least one compound of claim 1 in an amount of from 0.1 g to 10 kg per 100 kg of seed.

14. A method for controlling phytopathogenic harmful fungi, which comprises treating the fungi, their habitat or the plants to be protected against fungal attack, the soil or seeds with a compound of claim 1.

15. The method of claim 14, wherein $X^1$ is Cl.

16. The method of claim 14, wherein $X^2$ is Cl.

17. The method of claim 14, wherein $R^1$ is $C_1$-$C_4$-alkyl.

18. The method of claim 14, wherein $R^1$ is unsubstituted.

19. The method of claim 14, wherein $R^2$ is $C_3$-$C_8$-cycloalkyl-$C_1$-$C_4$-alkyl or phenyl-$C_1$-$C_4$-alkyl, that are unsubstituted or substituted by $R^a$ and/or $R^b$.

20. The method of claim 14, wherein $R^2$ is unsubstituted.

* * * * *